United States Patent
Kitazawa et al.

Patent Number: 5,387,603
Date of Patent: Feb. 7, 1995

[54] 1,5,7-TRISUBSTITUTED INDOLINE COMPOUNDS AND SALTS THEREOF

[75] Inventors: Makio Kitazawa; Masaaki Ban; Kosuke Okazaki; Motoyasu Ozawa; Toshikazu Yazaki; Ryoichi Yamagishi, all of Nagano, Japan

[73] Assignee: Kissei Pharmaceutical Co., Ltd., Nagano, Japan

[21] Appl. No.: 159,624

[22] Filed: Dec. 1, 1993

[30] Foreign Application Priority Data

Dec. 2, 1992 [JP] Japan .................. 4-356197

[51] Int. Cl.⁶ .................. A61K 31/40; C07D 209/14
[52] U.S. Cl. .................. 514/415; 514/339; 514/414; 548/465; 548/491; 546/273
[58] Field of Search .................. 514/339, 414, 415; 548/491, 465; 546/273

[56] References Cited

U.S. PATENT DOCUMENTS 4,521,606  6/1985  Asselin et al. .................. 548/503
4,638,070  1/1987  Lambelin et al. .................. 549/23

FOREIGN PATENT DOCUMENTS 077657  1/1968  Canada .................. 548/491
2512817  3/1983  France .................. 548/491

*Primary Examiner*—Mary C. Lee
*Assistant Examiner*—Jacqueline Haley
*Attorney, Agent, or Firm*—Sughrue, Mion, Zinn, Macpeak & Seas

[57] ABSTRACT

Indoline compounds represented by the formula:

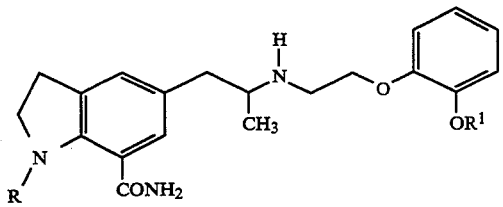

wherein R represents a saturated or unsaturated aliphatic acyl group which may have one or more halogen atoms, a hydroxy group, a lower alkoxy group, a carboxy group, a lower alkoxycarbonyl group, a cycloalkyl group or an aryl group as substituents; a hydroxyalkyl group; an aliphatic acyloxyalkyl group; a lower alkyl group having a lower alkoxy group, a carboxy group, a lower alkoxycarbonyl group, an aryl substituted lower alkoxycarbonyl group, a carbamoyl group, a mono- or dialkyl substituted carbamoyl group or a cyano group as substituents; an aromatic acyl group which may have one or more halogen atoms as substituents; a furoyl group or a pyridylcarbonyl group; $R^1$ represents a lower alkyl group which may have one or more halogen atoms or an aryl group as substituents; and pharmaceutically acceptable salts thereof, exhibit a selective suppressive action on urethral contractions, and thus are useful as therapeutic agents for the treatment of dysuria with less hypotension including postural hypotension.

15 Claims, No Drawings

1,5,7-TRISUBSTITUTED INDOLINE COMPOUNDS AND SALTS THEREOF

BACKGROUND OF THE INVENTION

1. Field of the Invention

The present invention relates to novel indoline compounds. More particular, the present invention relates to indoline compounds which exhibit a selective suppressive action on urethral contractions and thus are useful as therapeutic agents for the treatment of dysuria with less hypotension including postural hypotension.

2. Description of the Prior Art

As therapeutic agents for the treatment of dysuria, agents having a suppressive action on urethral contractions, such as Prazosin hydrochloride (Japanese Patent No.595,489) and Tamsulosin (Japanese Patent No.1,030,986) have been employed. However, they have adverse actions inducing hypotension including postural hypotension, and have to be carefully employed for patients, especially aging, suffering from dysuria.

Thus, for the treatment of dysuria, it has long been desired to develop a therapeutic agent having a selective suppressive action on urethral contractions with less hypotension including postural hypotension.

As compounds being close to indoline compounds of the present invention, certain compounds are disclosed in U.S. Pat. Nos. 4,521,606 and 4,638,070 as useful therapeutic agents for the treatment of hypertension. However, the indoline compounds of the present invention were in no way disclosed in any literature and it has not been reported indoline compounds including the compounds of the present invention to have a suppressive activity for urethral contractions in any literature and to be useful as therapeutic agents for the treatment of dysuria.

The indoline compounds of the present invention specifically suppress urethral contractions, thus they are useful as therapeutic agents for the treatment of dysuria with less hypotension including postural hypotension.

SUMMARY OF THE INVENTION

An object of the present invention is to provide novel indoline compounds which exhibit a selective suppressive action on urethral contractions with less hypotension including postural hypotension.

Another object of the present invention is to provide pharmaceutical compositions containing the indoline compound as an active ingredient.

A further object of the present invention is to provide a method for the treatment of dysuria comprising the indoline compound as an active ingredient.

Other objects, features and advantages of the present invention will be apparent from the following description of the invention.

DETAILED DESCRIPTION OF THE INVENTION

The present invention provides indoline compounds represented by the formula:

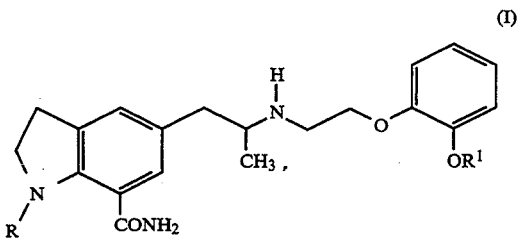

(I)

wherein R represents a saturated or unsaturated aliphatic acyl group which may have one or more halogen atoms, a hydroxy group, a lower alkoxy group, a carboxy group, a lower alkoxycarbonyl group, a cycloalkyl group or an aryl group as substituents; a hydroxyalkyl group; an aliphatic acyloxyalkyl group; a lower alkyl group having a lower alkoxy group, a carboxy group, a lower alkoxycarbonyl group, an aryl substituted lower alkoxycarbonyl group, a carbamoyl group, a mono- or dialkyl substituted carbamoyl group or a cyano group as substituents; an aromatic acyl group which may have one or more halogen atoms as substituents; a furoyl group or a pyridylcarbonyl group; $R^1$ represents a lower alkyl group which may have one or more halogen atoms or an aryl group as substituents; and pharmaceutically acceptable salts thereof, and which exhibit a selective suppressive action on urethral contraction, and thus are useful as therapeutic agents with less a postural hypotension and affecting a blood pressure for the treatment of dysuria.

The term "a lower alkyl" as used herein means a straight- or branched-chain alkyl radical having 1 to 6 carbon atoms.

The term "a hydroxyalkyl" as used herein means a straight- or branched-chain hydroxyalkyl radical having 2 to 6 carbon atoms and with proviso that said hydroxy group does not exist at α-position.

The term "a lower alkoxy" as used herein means a straight- or branched-chain alkoxy radical having 1 to 6 carbon atoms.

The term "a cycloalkyl" as used herein means a 5 to 7-membered cyclic alkyl radical.

The term "an aryl" as used herein means an aromatic hydrocarbon radical such as a phenyl radical, a naphthyl radical and the like.

The term "an aromatic acyl" as used herein means an arylcarbonyl radical wherein an aryl has the same meaning as mentioned above.

The term "an aliphatic acyl" as used herein means a straight- or branched-chain saturated or unsaturated alkylcarbonyl radical having 2 to 7 carbon atoms.

The term "an aliphatic acyloxyalkyl" as used herein means a straight- or branched-chain alkyl group having 2 to 6 carbon atoms and having a straight- or branched-chain saturated or unsaturated alkylcarbonyloxy group which does not exist at α-position.

The term "a furoyl" as used herein means a 2-furoyl radical or a 3-furoyl radical.

The term "a pyridylcarbonyl" as used herein means a 2-pyridylcarbonyl radical, a 3-pyridylcarbonyl radical or a 4-pyridylcarbonyl radical.

The term "a halogen atom" as used herein means a fluorine atom, a chlorine atom, a bromine atom or an iodine atom.

The indoline compounds represented by the formula (I) of the present invention can be prepared as follows.

That is, the indoline compounds of the present invention can be prepared by a reaction of a compound represented by the formula:

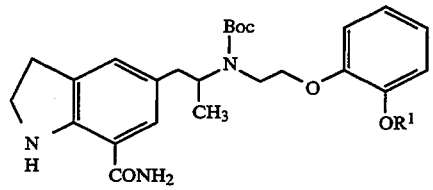
(II)

wherein Boc represents a tert-butoxycarbonyl group; R¹ has the same meaning as mentioned above, with a carboxylic acid compound or a reactive functional derivative thereof represented by the formula:

R²—OH  (III)

wherein R² represents an aliphatic acyl group which may have one or more halogen atoms, a hydroxy group protected by a protective group such as a tert-butyldimethylsilyl group and a benzyl group, a lower alkoxy group, a lower alkoxycarbonyl group, a cycloalkyl group or an aryl group as substituents; an aromatic acyl group which may have one or more halogen atoms as substituents; a furoyl group or a pyridylcarbonyl group; in the absence or the presence of a condensing agent such as N,N'-dicyclohexylcarbodiimide, 1,1'-carbonyldiimidazole, phosphorous oxychloride and phosphorous trichloride, or with an alkylating compound represented by the formula;

R³—A  (IV)

wherein R³ represents an alkyl group having a hydroxy group protected by a protective group such as a tert-butyldimethylsilyl group and a benzyl group; an aliphatic acyloxyalkyl group; a lower alkyl group having a lower alkoxy group, a lower alkoxycarbonyl group, an aryl substituted lower alkoxycarbonyl group, a carbamoyl group, a mono- or dialkyl substituted carbamoyl group or a cyano group as substituents; A represents a halogen atom, a 4-nitrobenzenesulfonyloxy group or a methanesulfonyloxy group, and, if desired, removing the OH-protective group in a usual manner, and, if desired, O-acylating the obtained hydroxy compound with an aliphatic carboxylic acid or a reactive functional derivative thereof in the absence or the presence of the condensing agent, and then, removing the Boc-group in a usual manner, and, if desired, hydrolyzing the obtained compound.

In the above process, a reactive functional derivative includes an acyl halide, an acid anhydride, an activated mixed acid anhydride, an activated ester, an activated amide and the like.

The compounds represented by the formula (II) used as the materials in the process stated above can be prepared according to the following process 1.

Process 1

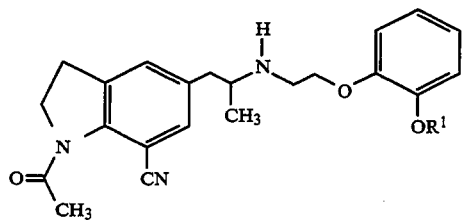
(V)

(wherein R¹ has the same meaning as mentioned above)

1) Step A
2) Step B
3) Step C

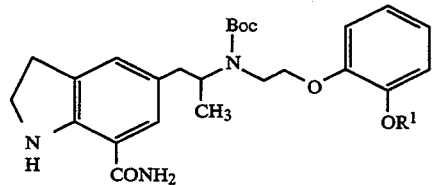
(II)

(wherein R¹ and Boc have the same meanings as mentioned above)

Step A; N-protective reaction with a Boc-derivatizing reagent.

Step B; deacetylating reaction under an alkaline condition.

Step C; converting reaction of the cyano group into the carbamoyl group with hydrogen peroxide in the presence of alkali metal hydroxide.

The compounds represented by the formula (II) can be also prepared according to the following process 2.

Process 2

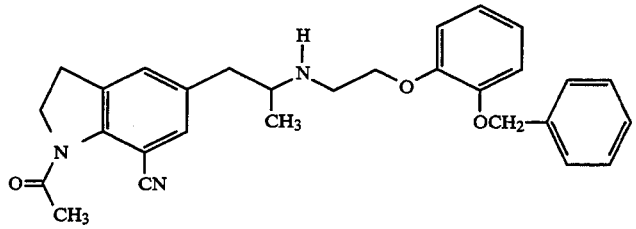
(VI)

Step A

Process 2

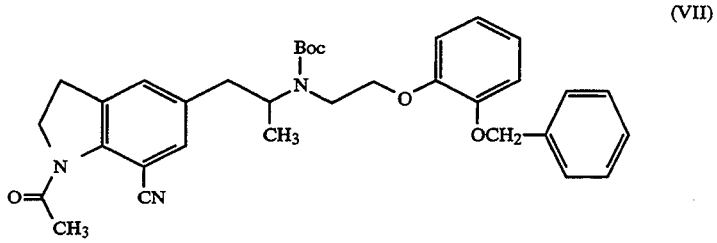
(VII)

(wherein Boc represents a tert-butoxy-carbonyl group)

↓ Catalytic hydrogenolysis

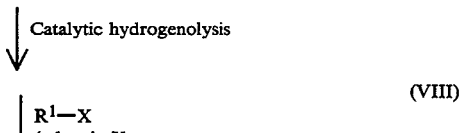
(VIII)

R¹—X
(wherein X represents a halogen atom;
R¹ has the same meaning as mentioned above)

↓
1) Step B
2) Step C
↓

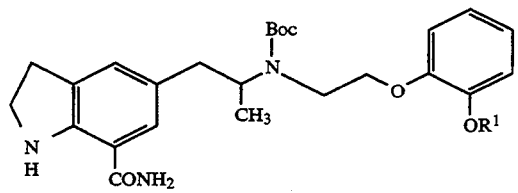
(II)

(wherein R¹ and Boc have the same meanings as mentioned above)

Of the compounds represented by the formula (I) of the present invention, compounds represented by the formula:

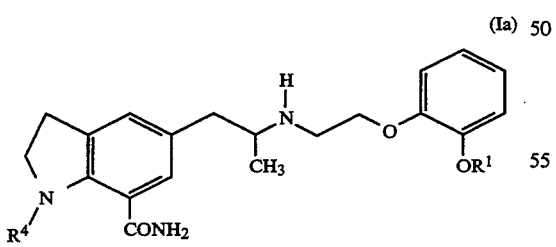
(Ia)

wherein R⁴ represents an aliphatic acyl group which may have one or more halogen atoms, a hydroxy group, a lower alkoxy group, a carboxy group, a lower alkoxycarbonyl group, a cycloalkyl group or an aryl group as substituents; an aromatic acyl group which may have one or more halogen atoms as substituents; a furoyl group or a pyridylcarbonyl group; R¹ has the same meaning as mentioned above, can be also prepared by treating a compound represented by the formula:

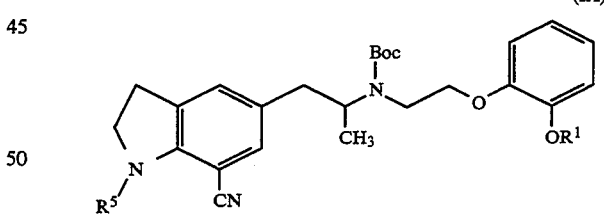
(IX)

wherein R⁵ represents an aliphatic acyl group which may have one or more halogen atoms, a hydroxy group protected by the protective group, a lower alkoxy group, a lower alkoxycarbonyl group, a cycloalkyl group or an aryl group as substituents; an aromatic acyl group which may have one or more halogen atoms as substituents; a furoyl group or a pyridylcarbonyl group; R¹ and Boc have the same meanings as mentioned above, with a concentrated hydrochloric acid, and, if desired, removing the OH-protective group in a usual manner, and, if desired, hydrolyzing the obtained compound.

The compounds represented by the formula (IX) used as the materials in the process stated above can be prepared by the following process 3.

Process 3

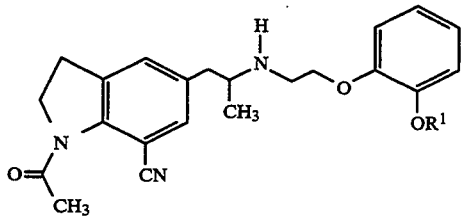

(wherein R¹ has the same meaning as mentioned above)

1) Step A
2) Step B

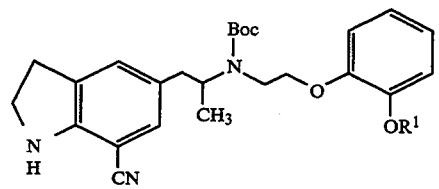

(wherein R¹ and Boc have the same meanings as mentioned above)

R⁵—X
(wherein R⁵ and X have the same meanings as mentioned above)

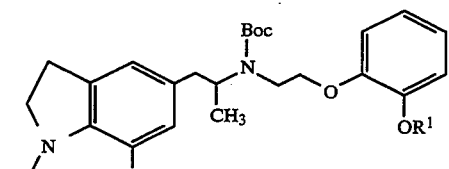

(wherein R¹, R⁵ and Boc have the same meanings as mentioned above)

Of the indoline compounds represented by the formula (I) of the present invention, compounds represented by the formula:

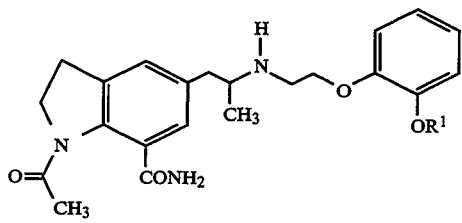

wherein R¹ has the same meaning as mentioned above, can be also prepared by treating a compound represented by the formula:

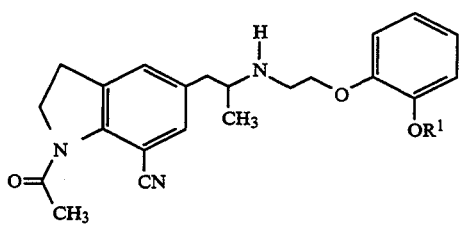

wherein R¹ has the same meaning as mentioned above, with a concentrated hydrochloric acid.

Of the compounds represented by the formula (I) of the present invention, compounds represented by the formula:

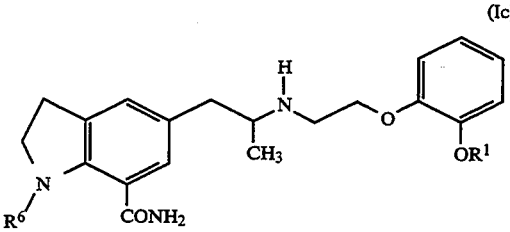

wherein $R^6$ represents a hydroxyalkyl group; an aliphatic acyloxyalkyl group or a lower alkyl group having a lower alkoxy group, a carboxy group, a lower alkoxycarbonyl group, an aryl substituted lower alkoxycarbonyl group, a carbamoyl group or a mono- or dialkyl substituted carbamoyl group as substituents; $R^1$ has the same meaning as mentioned above, can be also prepared by treating a compound represented by the formula:

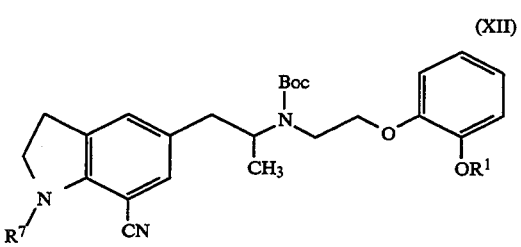

wherein $R^7$ represents a hydroxyalkyl group protected by the protective group; an aliphatic acyloxyalkyl group or a lower alkyl group having a lower alkoxy group, a lower alkoxycarbonyl group, an aryl substituted lower alkoxycarbonyl group, a carbamoyl group or a mono- or dialkyl substituted carbamoyl group as substituents; $R^1$ and Boc have the same meanings as mentioned above, with hydrogen peroxide in the presence of alkali metal hydroxide, and, if desired, removing the OH-protective group, and, if desired, hydrolyzing the obtained compound, and, if desired, benzylating or acylating the obtained compound with a benzylating agent or an aliphatic carboxylic acid or a reactive functional derivative thereof, and then, removing the Boc-group in a usual manner.

The compounds represented by the formula (XII) used as the materials in the process stated above can be prepared by the following process 4.

Process 4

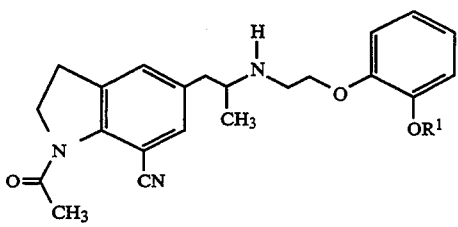 (V)

(wherein R¹ has the same meaning as mentioned above)

1) Step A
2) Step B

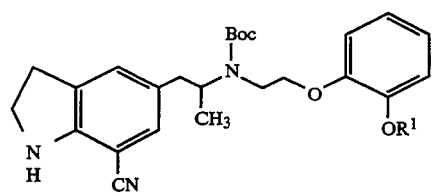 (X)

(wherein R¹ and Boc have the same meanings as mentioned above)

R⁷—X (XIII)
(wherein R⁷ and X have the same meanings as mentioned above)

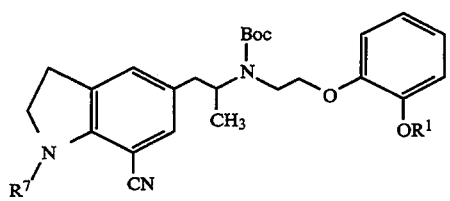 (XII)

(wherein R¹, R⁷ and Boc have the same meanings as mentioned above)

Of the indoline compounds represented by the formula (I) of the present invention, compounds represented by the formula:

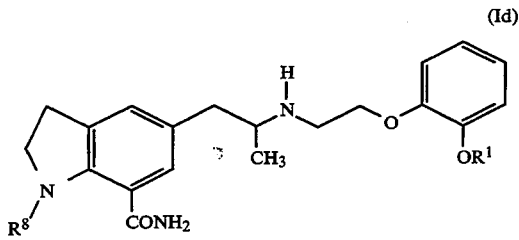 (Id)

wherein $R^8$ represents a saturated aliphatic acyl group which may have a hydroxy group, a lower alkoxy group, a carboxy group, a lower alkoxycarbonyl group, a cycloalkyl group or an aryl group as substituents; a hydroxyalkyl group; an aliphatic acyloxyalkyl group; a lower alkyl group having a lower alkoxy group, a carboxy group, a lower alkoxycarbonyl group, a benzyloxycarbonyl group, a carbamoyl group, a mono- or dialkyl substituted carbamoyl group or a cyano group as substituents; an aromatic acyl group; a furoyl group or a pyridylcarbonyl group; can be prepared by alkylating a compound represented by the formula:

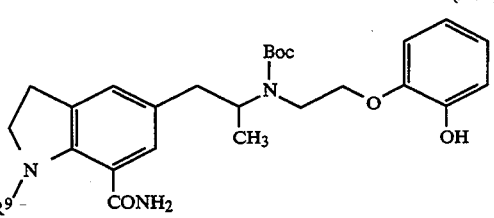 (XIV)

wherein $R^9$ represents a saturated aliphatic acyl group which may have a hydroxy group protected by the protective group, a lower alkoxy group, a lower alkoxycarbonyl group, a cycloalkyl group or an aryl group as substituents; a hydroxyalkyl group protected by the protective group; an aliphatic acyloxyalkyl group; a lower alkyl group having a lower alkoxy group, a lower alkoxycarbonyl group, a carbamoyl group, a mono- or dialkyl substituted carbamoyl group or a cyano group as substituents; an aromatic acyl group; a furoyl group or a pyridylcarbonyl group; Boc has the same meaning as mentioned above, with an alkylhalide compound represented by the formula:

$R^1$—X (VIII)

wherein $R^1$ and X have the same meanings as mentioned above, and, if desired, removing the OH-protective group in a usual manner, and, if desired, hydrolyzing the obtained compound, and, if desired, benzylating or acylating the obtained compound with a benzylating agent or an aliphatic carboxylic acid or a reactive functional derivative thereof, and then, removing the Boc-group in a usual manner.

The compounds represented by the formula (XIV) used as the starting materials in the above process can be prepared by a catalytic hydrogenolysis of a compound represented by the formula:

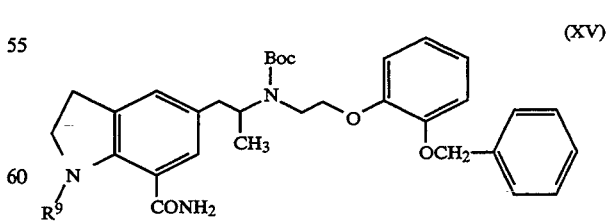 (XV)

wherein $R^9$ and Boc have the same meanings as mentioned above.

The compounds represented by the formulae (V) and (VI) used as the materials in the processes stated above can be prepared by the following process 5.

Process 5
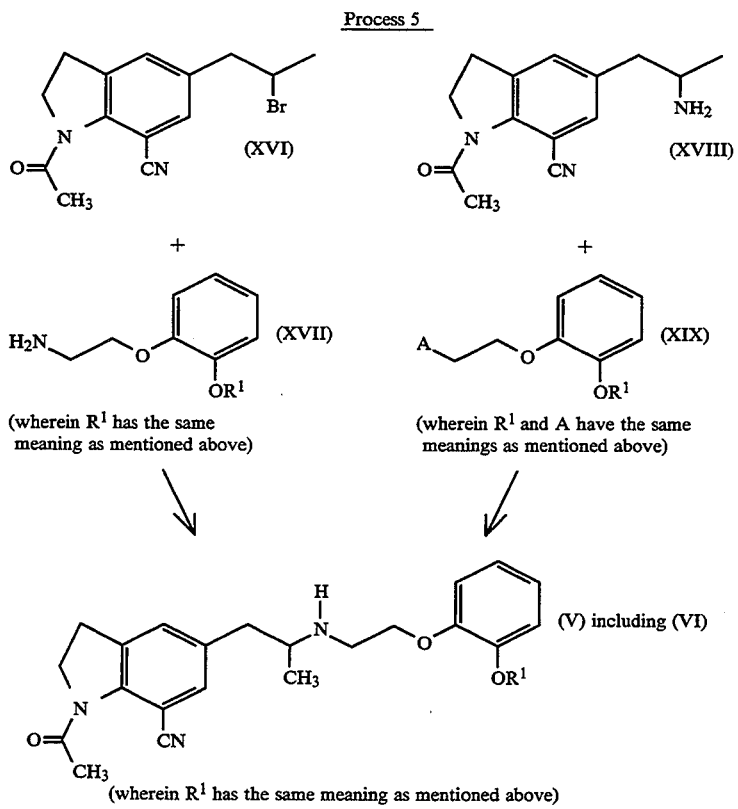
The compounds represented by the formulae (XVI) and (XVIII) used as the materials in the process 5 can be prepared by the following process 6.
Process 6
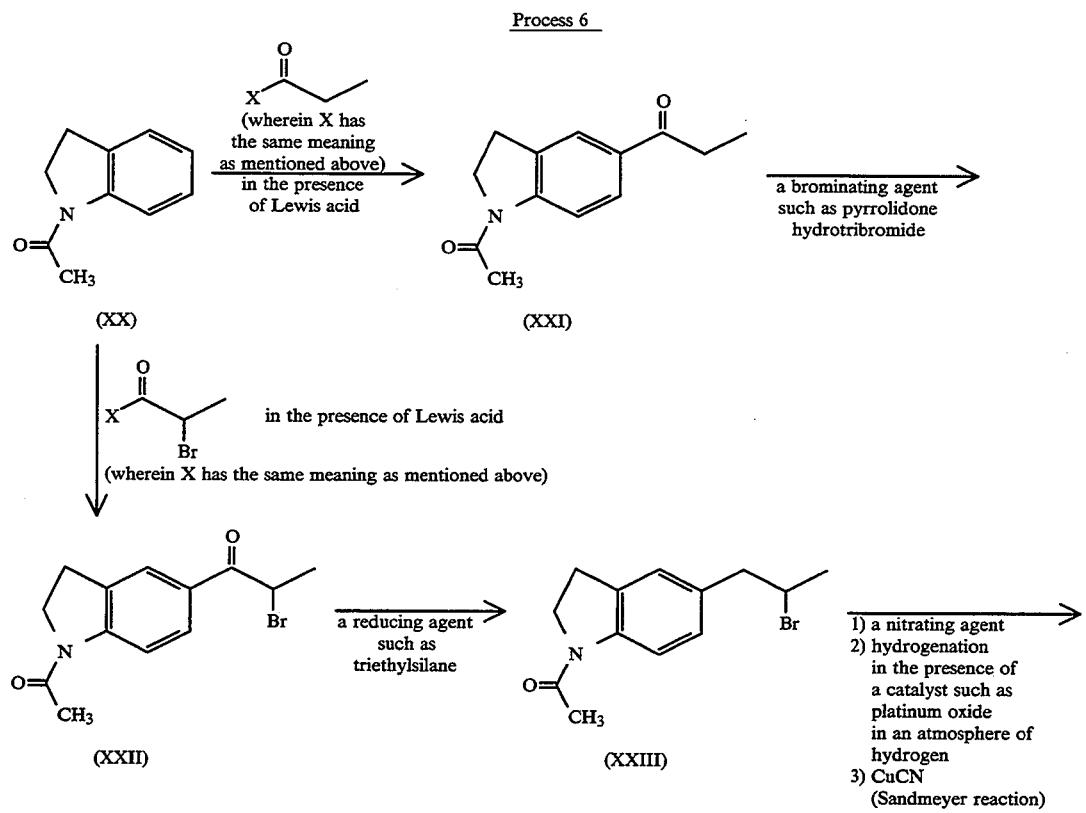

-continued
Process 6

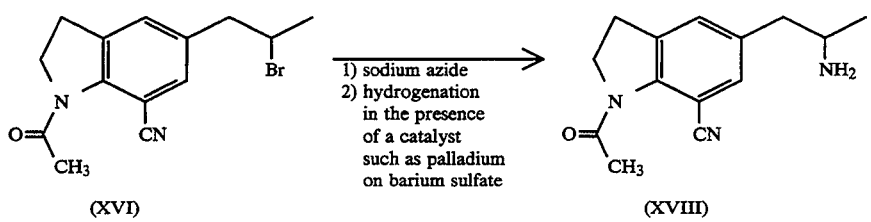

The compounds represented by the formulae (III), (IV), (VIII), (XI), (XIII), (XVII) and (XX) used as the materials in the processes stated above can be commercially available or can be easily prepared according to similar methods to those described in the literature.

The compounds represented by the formula (XIX) used as the materials in the process 5 can be prepared by a reaction of a phenol compound represented by the formula:

(XXIV)

wherein R¹ has the same meaning as mentioned above, with 1,2-dibromoethane, or by a reaction of the phenol compound of formula (XXIV) with ethyl bromoacetate, and reducing with a reducing agent such as lithium aluminum hydride, and then, a reaction of the obtained compound with a 4-nitrobenzenesulfonyl chloride or methanesulfonyl chloride.

The compound represented by the formula (XXIV) used as the materials in the process stated above can be commercially available or can be prepared by a reaction of the corresponding methyl ether derivative of the compound (XXIV) with boron tribromide.

The indoline compounds represented by the formula (I) of the present invention have some asymmetric carbon atoms, and consequently exist in the form of some isomers. The configuration of substituents on the asymmetric carbon atoms is not limited, and (R) configuration, (S) configuration or a mixture of (R) and (S) configurations can be employed in the present invention.

When the indoline compounds of the present invention have one or more unsaturated bonds in the substituent R, there are some geometrical isomers, and all geometrical isomers can be employed in the present invention.

The indoline compounds of the present invention specifically suppress urethral contractions induced by some agents such as phenylephrine not affecting a blood pressure, thus they may not induce hypotension including postural hypotension. Thus, the indoline compounds of the present invention are useful as therapeutic agents with less a postural hypotension and a hypotension.

The indoline compounds of the present invention have two substituents of R and R¹, and preferred examples of R are an aliphatic acyl group which may have a carboxy group as a substituent; a hydroxyalkyl group; an aliphatic acyloxyalkyl group and a lower alkyl group having a lower alkoxy group, a carboxy group, an aryl substituted lower alkoxycarbonyl group or a lower alkoxycarbonyl group as substituents, and preferred examples of R¹ are an alkyl group having 2 to 4 carbon atoms which may have one or more halogen atoms as substituents.

Examples of the preferred compounds are 1-butyryl-5-[2-[2-(2-ethoxyphenoxy)ethylamino]propyl]indoline-7-carboxamide, 1-(3-ethoxycarbonylpropyl)-5-[2-[2-(2-ethoxyphenoxy)ethylamino]propyl]indoline-7-carboxamide, 5-[2-[2-(2-ethoxyphenoxy)ethylamino]propyl]-1-(3-hydroxypropyl)indoline-7-carboxamide, 1-acetyl-5-[2-[2-[2-(2,2,2-trifluoroethoxy)phenoxy]ethylamino]propyl]indoline-7-carboxamide, 1-butyryl-5-[2-[2-[2-(2,2,2-trifluoroethoxy)phenoxy]ethylamino]propyl]indoline-7-carboxamide, 1-(3-ethoxycarbonylpropyl)-5-[2-[2-[2-(2,2,2-trifluoroethoxy)phenoxy]ethylamino]propyl]indoline-7-carboxamide, 1-(3-isopropoxycarbonylpropyl)-5-[2-[2-[2-(2,2,2-trifluoroethoxy)phenoxy]ethylamino]propyl]indoline-7-carboxamide, 1-(2-acetoxyethyl)-5-[2-[2-(2-ethoxyphenoxy)ethylamino]propyl]indoline-7-carboxamide, 4-[5-[2-[2-(2-ethoxyphenoxy)ethylamino]propyl]-7-carbamoylindolin-1-yl]butyric acid, 4-[5-[2-[2-[2-(2,2,2-trifluoroethoxy)phenoxy]ethylamino]propyl]-7-carbamoylindolin-1-yl]butyric acid, 4-[5-[2-[2-(2-ethoxyphenoxy)ethylamino]propyl]-7-carbamoylindolin-1-yl]-4-oxobutyric acid, 1-(3-methoxypropyl)-5-[2-[2-[2-(2,2,2-trifluoroethoxy)phenoxy]ethylamino]propyl]indoline-7-carboxamide, 1-(3-ethoxycarbonylpropyl)-5-[2-[2-(2-butoxyphenoxy)ethylamino]propyl]indoline-7-carboxamide, 1-(3-ethoxycarbonylpropyl)-5-[2-[2-(2-isopropoxyphenoxy)ethylamino] propyl]indoline-7-carboxamide, 4-[5-[2-[2-(2-isopropoxyphenoxy)ethylamino]propyl]-7-carbamoylindolin-1-yl]butyric acid, 1-(4-hydroxybutyl)-5-[2-[2-[2-(2,2,2-trifluoroethoxy)phenoxy]ethylamino]propyl]indoline-7-carboxamide, 1-butyryl-5-[2-[2-(2-butoxyphenoxy)ethylamino]propyl]indoline-7-carboxamide, 1-(3-benzyloxycarbonylpropyl)-5-[2-[2-(2-isopropoxyphenoxy)ethylamino]propyl]indoline-7-carboxamide and 1-(3-hydroxypropyl)-5-[2-[2-[2-(2,2,2-trifluoroethoxy)phenoxy]ethylamino]propyl]indoline-7-carboxamide.

Of the indoline compounds of the present invention, compounds wherein R¹ is a 2,2,2-trifluoroethyl group or an isopropyl group and R is a butyryl group, a 3-hydroxypropyl group, a 3-ethoxycarbonylpropyl group or a 3-methoxypropyl group are more preferable, and as examples of the more preferred compounds, 1-butyryl-5-[2-[2-[2-(2,2,2-trifluoroethoxy)phenoxy]ethylamino]propyl]indoline-7-carboxamide, 1-(3-ethoxycarbonylpropyl)-5-[2-[2-(2-isopropoxyphenoxy)ethylamino]propyl]indoline-7-carboxamide, 1-(3-ethoxycarbonylpropyl)-5-[2-[2-[2-(2,2,2-trifluoroethoxy)phenoxy]ethylamino]propyl]indoline-7-carboxamide, 1-(3-methoxypropyl)-5-[2-[2-[2-(2,2,2-trifluoroethoxy)phenoxy]ethylamino]propyl]indoline-7-carboxamide, 1-(3-hydroxypropyl)-5-[2-[2-[2-(2,2,2-trifluoroethoxy)phenoxy]ethylamino]propyl]indoline-7-carboxamide, (R)-1-butyryl-5-[2-[2-[2-(2,2,2-trifluoroethoxy)phenoxy)ethylamino]propyl]indoline-7-carboxamide, (R)-1-(3-ethoxycarbonylpropyl)-5-[2-[2-(2-isopropoxyphenoxy)ethylamino]propyl]indoline-7-carboxamide, (R)-1-(3-ethoxycarbonylpropyl)-5-[2-[2-[2-(2,2,2-trifluoroethoxy)phenoxy]ethylamino]propyl]indoline-7-carboxamide, (R)-1-(3-methoxypropyl)-5-[2-[2-[2-(2,2,2-trifluoroethoxy)phenoxy]ethylamino]propyl]indoline-7-carboxamide and (R)-1-(3-hydroxypropyl)-5-[2-[2-[2-(2,2,2-trifluoroethoxy)phenoxy]ethylamino]propyl]indoline-7-carboxamide are illustrated.

The pharmacological activity of the indoline compounds of the present invention can be confirmed by a modified method disclosed in literature [J. Smooth Muscle Res., 27(4), 254(1991)]. That is, it can be confirmed that the indoline compounds of the present invention strongly suppress urethral contraction induced by an intravenous administration of phenylephrine (30 µg/kg) in an experiment using anesthetized rats, and produce a 50% suppressive activity for urethral contraction at about 0.5 to 60 µg/kg. For example, (R)-1-(3-hydroxypropyl)-5-[2-[2-[2-(2,2,2-trifluoroethoxy)phenoxy]ethylamino]propyl]indoline-7-carboxamide produce a 50% suppressive activity at about 1.3 µg/kg.

On the other hand, the indoline compounds of the present invention show a little lowering activity for blood pressure at a high dose. That is, in an experiment using anesthetized rats, the indoline compounds of the present invention show a 10% lowering activity for blood pressure at an intravenous administration of about 10 to 100 µg/kg. For example, (R)-1-(3-hydroxypropyl)-5-[2-[2-[2-(2,2,2-trifluoroethoxy)phenoxy]ethylamino]propyl]indoline-7-carboxamide show a 10% lowering activity for blood pressure at an intravenous administration of about 26 µg/kg.

These findings clearly demonstrate that the indoline compounds of the present invention have a strong suppressive activity for urethral contractions, and that they are useful as therapeutic agents for the treatment of dysuria with less hypotension including postural hypotension.

The indoline compounds represented by the formula (I) of the present invention can be converted into pharmaceutically acceptable salts thereof according to conventional methods. In the case that there exist two amino groups in the indoline compounds of the present invention mono- or di-acid addition salt can be prepared, each acid addition salt can be employed in the present invention. Examples of such pharmaceutically acceptable salts wherein compounds having a carboxy group include inorganic salts such as sodium salts, potassium salts and calcium salts, and organic salts which are formed with organic amines such as morpholine and piperidine. Of the indoline compounds of the present invention, compounds wherein R represents a substituted or unsubstituted acyl group or a furoyl group can be converted into mono-acid addition salts formed by hydrochloric acid, hydrobromic acid, benzenesulfonic acid, p-toluenesulfonic acid, acetic acid, citric acid, succinic acid, tartaric acid, 2,4-dimethylbenzenesulfonic acid, 2,5-dimethylbenzenesulfonic acid, 2,4,6-trimethylbenzenesulfonic acid, (+)-camphorsulfonic acid, (−)-camphorsulfonic acid, 4-chlorobenzenesulfonic acid, 2-naphthalenesulfonic acid, 1-butanesulfonic acid, fumaric acid, glutamic acid, aspartic acid and the like. Of the indoline compounds of the present invention, compounds wherein R represents a substituted alkyl group or a pyridylcarbonyl group can be converted into mono- or di-acids addition salts formed by hydrochloric acid, hydrobromic acid, benzenesulfonic acid, p-toluenesulfonic acid, 2,4-dimethylbenzenesulfonic acid, 2,5-dimethylbenzenesulfonic acid, 2,4,6-trimethylbenzenesulfonic acid, (+)-camphorsulfonic acid, (−)-camphorsulfonic acid, 4-chlorobenzenesulfonic acid, 2-naphthalenesulfonic acid, 1-butanesulfonic acid and the like, and mono-acid addition salts formed by acetic acid, citric acid, succinic acid, tartaric acid, fumaric acid, glutamic acid, aspartic acid and the like. These pharmaceutically acceptable salts also possess on a selective suppressive action on urethral contractions as well as the free compound thereof, and thus are useful as a therapeutic agent for the treatment of dysuria with less hypotension including postural hypotension.

When the indoline compounds of the formula (I) of the present invention or the pharmaceutically acceptable salts thereof are employed therapeutically, they can be administered orally or parenterally in appropriate dosage forms, e.g., tablets, powders, capsules and injectable preparations. These pharmaceutical compositions can be formulated in accordance with conventional molding methods.

The dosage of the indoline compounds of the present invention may be in the range from about 0.5 to 500 mg per adult human by an oral administration per day, or about 0.05 to 100 mg per adult human by a parenteral administration per day in multiple dose depending upon the sex, age, weight of the patient and severity of the diseases.

The present invention is further illustrated in more detail by way of the following Reference Examples and Examples. The melting points of the product obtained are uncorrected.

Reference Example 1

1-Acetyl-5-(2-bromopropyl)indoline

To a solution of 1-acetyl-5-propionylindoline (1.65 g) in tetrahydrofuran (150 ml) were added concentrated sulfuric acid (5 drops) and pyrrolidone hydrotribromide (4.14 g), and the mixture was stirred at room temperature for 16 hours. The insoluble materials were filtered off, and the filtrate was concentrated under reduced pressure. The residue was extracted with ethyl acetate, and the extract was washed with water, dried over anhydrous magnesium sulfate. The solvent was evaporated under reduced pressure, and the residue was recrystallized from ethanol to give 1.78 g of 1-acetyl-5-(2-bromopropionyl)indoline melting at 140°–142° C.

IR (KBr): $\nu$C=O 1675, 1660 cm$^{-1}$

NMR (CDCl$_3$)

$\delta$: 1.89(3H, d, J=6.4Hz), 2.27(3H, s), 3.26(2H, t, J=8.4Hz), 4.14(2H, t, J=8.4Hz), 5.27(1H, q, J=6.4Hz), 7.87(1H, s), 7.89(1H, d, J=8.4Hz), 8.26(1H, d, J=8.4Hz)

To a solution of 1-acetyl-5-(2-bromopropionyl)indoline (210 g) in trifluoroacetic acid (700 ml) was added triethylsilane (190 g) over a period of 30 minutes with stirring under ice cooling, the mixture was stirred for 30 minutes under ice cooling, and then for 1 hour at room temperature. After the reaction mixture was concentrated under reduced pressure, the residue was poured into water (2 l), and to the mixture was added hexane (500 ml) and stirred. The precipitates were collected by filtration, washed with hexane, and recrystallized from ethyl acetate-hexane to give 153 g of 1-acetyl-5-(2-bromopropyl)indoline melting at 124°–126° C.

IR (KBr): $\nu$C=O 1652 cm$^{-1}$

NMR (CDCl$_3$)

δ: 1.68(3H, d, J=6.9Hz), 2.22(3H, s), 2.95–3.10(1H, m), 3.10–3.25(3H, m), 4.06(2H, t, J=8.4Hz), 4.20–4.30(1H, m), 6.90–7.05(2H, m), 8.13(1H, d, J=8.9Hz)

Reference Example 2
1-Acetyl-5-(2-bromopropyl)-7-nitroindoline

To a solution of 1-acetyl-5-(2-bromopropyl)indoline (153 g) in acetic acid (240 ml) was added fuming nitric acid (120 ml) with stirring under ice cooling over a period of 1 hour, and the mixture was stirred at room temperature for 30 minutes. After the reaction mixture was poured into ice water slowly, the precipitates were collected by filtration, and dissolved in benzene (1.5 l). The benzene solution was washed with water, and dried over anhydrous magnesium sulfate. The solvent was evaporated under reduced pressure, and the residue was recrystallized from ethyl acetate-isopropyl ether to give 155 g of 1-acetyl-5-(2-bromopropyl)-7-nitroindoline melting at 119°–120° C.

IR (KBr): υC=O 1680 cm$^{-1}$
NMR (CDCl$_3$)

δ: 1.73(3H, d, J=6.6Hz), 2.26(3H, s), 3.10–3.15(2H, m), 3.22 (2H, t, J=8.0Hz), 4.20–4.30(3H, m), 7.29(1H, s), 7.49(1H, s)

Reference Example 3
1-Acetyl-5-(2-bromopropyl)indoline-7-carbonitrile

To a solution of 1-acetyl-5-(2-bromopropyl)-7-nitroindoline (50 g) in ethanol (1.5 l) was added platinum oxide (2.5 g), and the mixture was stirred at room temperature for 4 hours under an atmosphere of hydrogen. After the catalyst was filtered off, the filtrate was evaporated under reduced pressure, to give 45 g of 1-acetyl-7-amino-5-(2-bromopropyl)indoline.

NMR (CDCl$_3$)

δ: 1.66(3H, d, J=6.6Hz), 2.29(3H, s), 2.92(1H, dd, J=13.9, 7.7Hz), 3.02 (2H, t, J=7.8Hz ), 3.13 (1H, dd, J=13.9, 6.6Hz), 4.04(2H, J=7.8Hz), 4.20–4.30(1H, m), 4.81 (2H, br s), 6.40(1H, s), 6.47(1H, s)

1-Acetyl-7-amino-5-(2-bromopropyl)indoline (59.4 g) was dissolved in 28% hydrochloric acid (50 ml) under ice cooling, and then, to the solution was added an aqueous solution (40 ml) of sodium nitrite (16.2 g) at 0°–5° C., the mixture was stirred for 1 hour. To the reaction mixture was added sodium carbonate with stirring under ice cooling, the pH of the reaction mixture was adjusted to pH 7.

On the other hand, to a suspension of copper(I) cyanide (17.9 g) in water (150 ml) was added sodium cyanide (32 g) little by little at room temperature, and then was added toluene (150 ml), and the mixture was stirred at 75° C. for 30 minutes. To the reaction mixture was added diazonium salt which was prepared above, and the mixture was stirred at 75° C. for 2 hours. The reaction mixture was extracted with ethyl acetate. The extract was washed with water, dried over anhydrous magnesium sulfate and evaporated under reduced pressure. The residue was purified by flash column chromatography on silica gel using a mixture of ethyl acetate and hexane (3/2) as eluent to give 29.1 g of 1-acetyl-5-(2-bromopropyl)indoline-7-carbonitrile melting at 115°–117° C.

IR (KBr): υCN 2228 cm$^{-1}$ υC=O 1673 cm$^{-1}$
NMR (CDCl$_3$)

δ: 1.72(3H, d, J=6.7Hz), 2.32(3H, s), 3.05–3.10(2H, m), 3.15(2H, t, J=8.0Hz), 4.15 (2H, t, J=8.0Hz), 4.15–4.25(1H,+m), 7.27(1H, s), 7.31(1H, s)

Reference Example 4
1-Acetyl-5-(2-aminopropyl)indoline-7-carbonitrile

1-Acetyl-5-(2-bromopropyl)indoline-7-carbonitrile (1.42 g) and sodium azide (0.30 g) were dissolved in diethylene glycol monoethyl ether (1.4 ml) and water (3.2 ml), and the mixture was stirred at 90° C. for 9.5 hours.-To the reaction mixture was added water, and the mixture was extracted with methylene chloride. The extract was washed with water, dried over anhydrous magnesium sulfate. The solvent was evaporated under reduced pressure, and the residue was purified by medium pressure liquid column chromatography on silica gel using a mixture of ethyl acetate and hexane (3/1) as eluent to give 1.10 g of 1-acetyl-5-(2-azidopropyl)indoline-7-carbonitrile as an oil.

IR (neat): υCN 2250 cm$^{-1}$ υN$_3$ 2145 cm$^{-1}$ υC=O 1690 cm$^{-1}$
NMR (CDCl$_3$)

δ: 1.29(3H, d, J=6.4Hz), 2.32(3H, s), 2.72(2H, d, J=6.9Hz), 3.15(2H, t, J=7.9Hz), 3.60–3.i75(1H, m), 4.16(2H, t, J=7.9Hz), 7.27(1H, s), 7.30(1H, s)

To a solution of 1-acetyl-5-(2-azidopropyl)indoline-7-carbonitrile (0.20 g) in ethanol (16 ml) was added 5% palladium on barium sulfate (102 mg), and the mixture was stirred at room temperature for 8 hours under an atmosphere of hydrogen. After the catalyst was filtered off, the filtrate was concentrated to dryness to give 0.18 g of 1-acetyl-5-(2-aminopropyl)indoline-7-carbonitrile melting at 94°–96° C.

IR (KBr): υNH 3375 cm$^{-1}$ υCN 2220 cm$^{-1}$ υC=O 1670 cm$^{-1}$
NMR (CDCl$_3$)

δ: 1.11(3H, d, J=6.4Hz), 2.32(3H, s), 2.51(1H, dd, J=13.4, 7.9Hz), 2.67(1H, dd, J=13.4, 5.4Hz), 3.05–3.25(3H, m), 4.15(2H, t, J=7.9Hz), 7.25(1H, s), 7.30(1H, s)

Reference Example 5
1-(2-Bromoethoxy)-2-(2,2,2-trifluoroethoxy)benzene

To dry N,N-dimethylformamide (10 ml) were added 2-methoxyphenol (150 mg), 2,2,2-trifluoroethyl iodide (584 mg) and potassium carbonate (400 mg), and the mixture was stirred vigorously at 130° C. for 6 hours. To the reaction mixture was added water, and the mixture was extracted with diethyl ether. The extract was washed with water, dried over anhydrous magnesium sulfate. The solvent was evaporated under reduced pressure, and the residue was purified by medium pressure liquid column chromatography on silica gel using a mixture of hexane and chloroform (5/2) as eluent to give 179 mg of 1-methoxy-2-(2,2,2-trifluoroethoxy) benzene as an oil.

NMR (CDCl$_3$)

δ: 3.87(3H, s), 4.39(2H, q, J=8.4Hz), 6.85–7.10(4H, m)

To a solution of 1-methoxy-2-(2,2,2-trifluoroethoxy)-benzene (3.83 g) in dry methylene chloride (50 ml) was added boron tribromide (3.1 ml) with stirring under ice cooling, and the mixture was reacted for 30 minutes. The reaction mixture was poured into an aqueous sodium bicarbonate solution (500 ml), and the mixture was extracted with diethyl ether. The extract was washed with water, dried over anhydrous magnesium sulfate. The solvent was evaporated under reduced pressure, and the residue was purified by medium pressure liquid column chromatography on silica gel using a mixture of hexane and diethyl ether (20/1) as eluent to give 2.37 g of 2-(2,2,2-trifluoroethoxy)phenol melting at 49°–50° C.

IR (KBr): υOH 3310 cm$^{-1}$
NMR (CDCl$_3$)

δ: 4.42(2H, q, J=7.9Hz), 5.53(1H, s), 6.80-7.10(4H, m)

To an aqueous solution (15 ml) of sodium hydroxide (0.63 g) were added 2-(2,2,2-trifluoroethoxy)phenol (2.85 g) and 1,2-dibromoethane (1.68 ml), and the mixture was reacted with stirring at 120° C. for 8 hours. To the reaction mixture was added concentrated hydrochloric acid (1.3 ml), and the mixture was extracted with diethyl ether. The extract was washed with water, dried over anhydrous magnesium sulfate. The solvent was evaporated under reduced pressure, and the residue was purified by medium pressure liquid column chromatography on silica gel using a mixture of hexane and diethyl ether (5/1) as eluent to give 1.78 g of 1-(2-bromoethoxy)-2-(2,2,2-trifluoroethoxy)benzene as an oil NMR (CDCl$_3$)

δ: 3.67(2H, t, J=6.0Hz), 4.34(2H, t, J=6.0Hz), 4.43(2H, q, J=8.2Hz), 6.90-7.20(4H, m)

Reference Example 6

2-[2-(2,2,2-Trifluoroethoxy)phenoxy]ethyl methanesulfonate

To a solution of 2-(2,2,2-trifluoroethoxy)phenol (200 mg) in dry N,N-dimethylformamide (2 ml) were added ethyl bromoacetate (138 μl) and potassium carbonate (216 mg), and the mixture was reacted with stirring at room temperature for 1 hour, and then for 1 hour at 60° C. To the reaction mixture was added ethyl acetate, and ethyl acetate solution was washed with water and dried over anhydrous magnesium sulfate. The solvent was evaporated under reduced pressure to give 270 mg of ethyl 2-(2,2,2-trifluoroethoxy)phenoxyacetate as an oil.

IR (neat): υC=O 1760 cm$^{-1}$

NMR (CDCl$_3$)

δ: 1.29(3H, t, J=7.1Hz), 4.26(2H, q, J=7.1Hz), 4.47(2H, q, J=8.4Hz), 4.68(2H, s), 6.85-7.10(4H, m)

To a suspension of lithium aluminum hydride (79 mg) in dry tetrahydrofuran (1 ml) was added dropwise a solution of ethyl 2-(2,2,2-trifluoroethoxy)phenoxyacetate (270 mg) in dry tetrahydrofuran (3 ml) with stirring under ice cooling, and the mixture was reacted at room temperature for 40 minutes. To the reaction mixture were added anhydrous sodium sulfate and water with stirring. The insoluble materials were filtered off, and the filtrate was concentrated under reduced pressure. The residue was purified by medium pressure liquid column chromatography on silica gel using a mixture of hexane and ethyl acetate (2/1) as eluent to give 213 mg of 2-[2-(2,2,2-trifluoroethoxy)phenoxy]ethanol as an oil.

IR (neat): υOH 3400 cm$^{-1}$

NMR (CDCl$_3$)

δ: 2.24(1H, br s), 3.90-4.00(2H, m), 4.10-4.15(2H, m), 4.39(2H, q, J=8.3Hz), 6.90-7.10(4H, m)

To a solution of 2-[2-(2,2,2-trifluoroethoxy)phenoxy]ethanol (210 mg) in methylene chloride (1 ml) were added triethylamine (186 μl) and methanesulfonyl chloride (83 μl) with stirring under ice cooling, and the mixture was reacted at room temperature for 30 minutes. The reaction mixture was concentrated under reduced pressure. To the concentrate was added water, and the mixture was extracted with diethyl ether. The extract was washed with water, dried over anhydrous magnesium sulfate. The solvent was evaporated under reduced pressure, and the residue was purified by medium pressure liquid column chromatography on silica gel using a mixture of hexane and ethyl acetate (2/1) as eluent to give 273 mg of 2-[2-(2,2,2-trifluoroethoxy)phenoxy]ethyl methansulfonate melting at 40.5°-42.0° C.

IR (KBr): υSO$_2$ 1350, 1120 cm$^{-1}$

NMR (CDCl$_3$)

δ: 3.12(3H, s), 4.25-4.30(2H, m), 4.38(2H, q, J=8.3Hz), 4.55-4.65 (2H, m), 6.90-7.10 (4H, m)

Reference Example 7

1-Acetyl-5-[2-[2-(2-ethoxyphenoxy)ethylamino]propyl]indoline-7-carbonitrile

To a solution of 1-acetyl-5-(2-bromopropyl)indoline-7-carbonitrile (300 mg) and 2-(2-ethoxyphenoxy)ethylamine (391 mg) in dioxane (4 ml) were added potassium iodide (17 mg) and 18-crown-6 (26 mg), and the mixture was reacted in a sealed tube at 180° C. for 18 hours. The reaction mixture was concentrated under reduced pressure, and the residue was purified by flash column chromatography on silica gel using a mixture of methylene chloride and methanol (40/1) as eluent to give 111 mg of 1-acetyl-5-[2-[2-(2-ethoxyphenoxy)ethylamino] propyl]indoline-7-carbonitrile as an oil.

IR (neat): υCN 2224cm$^{-1}$ υC=O 1676 cm$^{-1}$

NMR (CDCl$_3$)

δ: 1.14(3H, d, J=6.0Hz), 1.42(3H, t, J=6.9Hz), 2.31(3H, s), 2.55-2.70(1H, m), 2.90-3.20(6H, m), 4.00-4.20(6H, m), 6.85-6.95(4H, m), 7.30(2H, br s)

Reference Example 8

1-Acetyl-5-[2-[2-[2-(2,2,2-trifluoroethoxy)phenoxy]ethylamino]propyl]indoline-7-carbonitrile To a solution of 1-acetyl-5-(2-aminopropyl)indoline-7-carbonitrile (1.37 g) and 1-(2-bromoethoxy)-2-(2,2,2-trifluoroethoxy)benzene (1.50 g) in ethanol (6 ml) was added sodium bicarbonate (0.47 g), and the mixture was reacted in a sealed tube at 95° C. for 12 hours. The reaction mixture was concentrated under reduced pressure, and the residue was purified by medium pressure liquid column chromatography on silica gel using a mixture of methylene chloride, diethyl ether and methanol (5/5/1) as eluent, and recrystallized from diethyl ether-hexane to give 1.30 g of 1-acetyl-5-[2-[2-[2-(2,2,2-trifluoroethoxy)phenoxy]ethylamino]propyl]indoline-7-carbonitrile melting at 64°-65° C.

IR (KBr): υNH 2931 cm$^{-1}$ υCN 2221 cm$^{-1}$ υC=O 1673 cm$^{-1}$

NMR (CDCl$_3$)

δ: 1.06(3H, d, J=6.4Hz), 2.31(3H, s), 2.56(1H, dd, J=13.2, 6.9Hz), 2.75(1H, dd, J=13.2, 6.4Hz), 2.90-3.20(5H, m), 4.00-4.20(4H, m), 4.33(2H, q, J=8.4Hz), 6.80-7.20(4H, m), 7.24(1H, s), 7.30(1H, s)

Reference Example 9

1-Acetyl-5-[2-[2-(2-benzyloxyphenoxy)ethylamino]propyl]indoline-7-carbonitrile

In a similar manner to that described in Reference Example 8, 1-acetyl-5-[2-[2-(2-benzyloxyphenoxy)ethylamino]propyl]indoline-7-carbonitrile was prepared by using 2-(2-benzyloxyphenoxy)ethylbromide.

NMR (CDCl$_3$)

δ: 0.99(3H, d, J=6.4Hz), 2.29(3H, s), 2.47(1H, dd, J=13.4, 7.4Hz), 2.70(1H, dd, J=13.4, 5.9Hz), 2.80-3.15(5H, m), 4.00-4.20(5H, m), 5.07(2H, s), 6.80-7.00(4H, m), 7.19(1H, s), 7.20-7.45(6H, m)

Reference Example 10

1-Acetyl-5-[2-[2-[2-(2,2,2-trifluoroethoxy)phenoxy]ethylamino]propyl]indoline-7-carbonitrile To a solution of 1-acetyl-5-(2-aminopropyl)indoline-7-carbonitrile (18.85 g) and 2-[2-(2,2,2-trifluoroethoxy)phenoxy] ethyl methanesulfonate (24.34 g) in ethanol (155 ml) was added sodium bicarbonate (7.81 g), and the mixture was refluxed for 24 hours. To the reaction mixture was added water (1 l), and the mixture was extracted with diethyl ether. The extract was dried over anhydrous magnesium sulfate. The solvent was evaporated under reduced pressure, and the residue was purified by flash column chromatography on silica gel using a mixture of chloroform and methanol (10/1) as eluent to give 23.48 g of 1-acetyl-5-[2-[2-[2-(2,2,2-trifluoroethoxy)phenoxy]ethylamino]propyl]indoline-7-carbonitrile. The physical properties of this compound were completely identical to those of the compound prepared in Reference Example 8.

Reference Example 11

In a similar manner to that described in Reference Example 10, the following compounds were prepared.

1-Acetyl-5-[2-[2-(2-isopropoxyphenoxy)ethylamino]-propyl]indoline-7-carbonitrile IR (neat): υNH 3320 cm$^{-1}$ υCN 2223 cm$^{-1}$ υC=O 1680 cm$^{-1}$ NMR (CDCl$_3$)

δ: 1.05(3H, d, J=6.3Hz), 1.31(6H, d, J=6.1Hz), 2.31(3H, s), 2.55(1H, dd, J=13.5, 7.1Hz), 2.77(1H, dd, J=13.5, 6.0Hz), 2.90–3.10(5H, m), 4.05–4.20(4H, m), 4.43(1H, sept, J=6.1Hz), 6.85–6.95(4H, m), 7.24(1H, s), 7.29(1H, s)

1-Acetyl-5-[2-[2-(2-butoxyphenoxy)ethylamino]-propyl]indoline-7-carbonitrile

IR (neat): υNH 3330 cm$^{-1}$ υCN 2223 cm$^{-1}$ υC=O 1679 cm$^{-1}$

NMR (CDCl$_3$)

δ: 0.97(3H, t, J=7.4Hz), 1.04(3H, d, J=6.3Hz), 1.45–1.55(2H, m), 1.70–1.85(2H, m), 2.30(3H, s), 2.54(1H, dd, J=13.5, 7.2Hz), 2.78(1H, dd, J=13.5, 5.9Hz), 2.90–3.10(5H, m), 3.98(2H, t, J=6.5Hz), 4.05–4.15(4H, m), 6.85–6.95(4H, m), 7.24(1H, s), 7.29(1H, s)

Reference Example 12

1-Acetyl-5-[2-[N-tert-butoxycarbonyl-2-(2-ethoxyphenoxy)ethylamino]propyl]indoline-7-carbonitrile To a solution of 1-acetyl-5-[2-[2-(2-ethoxyphenoxy)ethylamino]propyl]indoline-7-carbonitrile (200 mg) in dry methylene chloride (2 ml) was added di-tert-butyl dicarbonate (160 mg), and the mixture was reacted at room temperature for 2 hours. The reaction mixture was concentrated under reduced pressure, and the residue was purified by flash column chromatography on silica gel using a mixture of chloroform and ethyl acetate (4/1) as eluent to give 167 mg of 1-acetyl-5-[2-[N-tert-butoxycarbonyl-2-(2-ethoxyphenoxy) ethylamino]-propyl]indoline-7-carbonitrile as an oil.

IR (neat): υCN 2225 cm$^{-1}$ υC=O 1685 cm$^{-1}$

NMR (CDCl$_3$)

δ: 1.26(3H, d, J=6.4Hz), 1.43(12H, br s), 2.31(3H, s), 2.65–2.75(1H, m), 2.90–3.10(3H, m), 3.40–3.55(2H, m), 3.85–4.25(7H, m), 6.75–6.95(4H, m), 7.15–7.30(2H, m)

Reference Example 13

In a similar manner to that described in Reference Example 12, the following Boc-compounds were prepared by using di-tert-butyl dicarbonate.

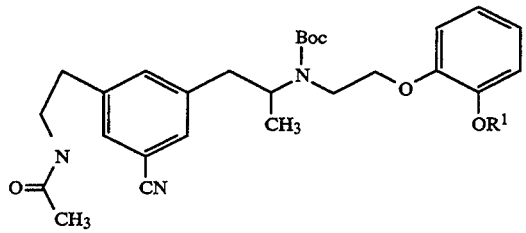

| R$^1$ | IR (cm$^{-1}$) | Specific rotation*) [α]$_D$ | NMR (δ, CDCl$_3$) |
|---|---|---|---|
| benzyl | 2224 (CN) 1685 (C=O) | | 1.18(3H, d, J=6.8Hz), 1.42(9H, s), 2.30(3H, s), 2.60 (1H, dd, J=13.6, 6.8Hz), 2.80–3.10(3H, m), 3.30–3.60 (2H, m), 3.85–4.20(5H, m), 5.10(2H, br s), 6.80–7.00(4H, m), 7.05–7.45(7H, m) |
| 2,2,2-trifluoroethyl | 2228 (CN) 1680 (C=O) | | 1.27(3H, d, J=6.7Hz), 1.43(9H, s), 2.30(3H, s), 2.68 (1H, dd, J=13.8, 6.6Hz), 2.80–3.15(3H, m), 3.30–3.60 (2H, m), 3.85–4.20(5H, m), 4.36(2H, q, J=8.3Hz), 6.80–7.40(6H, m) |
| 2,2,2-trifluoroethyl | similar to that of the racemate | −46.7° (c=1.10, MeOH) | similar to that of the racemate |
| 2,2,2-trifluoroethyl | similar to that of the racemate | +47.3° (c=1.14, MeOH) | similar to that of the racemate |
| ethyl | similar to that of the compound in Reference Example 12 | −51.7° (c=1.88, MeOH) | similar to that of the compound in Reference Example 12 |
| isopropyl | 2224 (CN) 1685 (C=O) | | 1.27(3H, d, J=7.1Hz), 1.33(6H, d, J=6.1Hz), 1.42(9H, s), 2.30(3H, s), 2.60–2.80(1H, m), 2.90–3.10(3H, m), 3.35–3.60(2H, m), 3.85–4.30(5H, m), 4.49(1H, sept, J=6.1Hz), 6.80–6.95(4H, m), 7.10–7.35(2H, m) |
| butyl | 2244 (CN) 1685 (C=O) | | 0.96(3H, t, J=7.4Hz), 1.26(3H, d, J=6.3Hz), 1.40–1.55(11H, m), 1.70–1.85(2H, m), 2.30(3H, s), 2.60–2.75(1H, m), 2.90–3.10(3H, m), 3.35–3.60(2H, m), 3.85–4.30(7H, m), 6.75–6.95(4H, m), 7.10–7.35(2H, m) |

*) blank means a racemate

Reference Example 14

5-[2-[N-tert-butoxycarbonyl-2-(2-ethoxyphenoxy)ethylamino]propyl]indoline-7-carbonitrile To a solution of 1-acetyl-5-[2-[N-tert-butoxycarbonyl-2-(2-ethoxyphenoxy)ethylamino]propyl]indoline-7-carbonitrile (167 mg) in ethanol (2.2 ml) was added a 5N-sodium hydroxide solution (1.1 ml), and the mixture was reacted at room temperature for 2.5 hours. The reaction mixture was neutralized by adding acetic acid, and extracted with methylene chloride. The extract was washed with water and a saturated aqueous sodium bicarbonate solution, dried over anhydrous magnesium sulfate. The solvent was evaporated under reduced pressure to give 133 mg of 5-[2-[N-tert-butoxycarbonyl-2-(2-ethoxyphenoxy)ethylamino]propyl]indoline-7-carbonitrile as an oil.

IR (neat): $\nu$CN 2214 cm$^{-1}$ $\nu$C=O 1686 cm$^{-1}$
NMR (CDCl$_3$)
$\delta$: 1.24(3H, d, J=6.6Hz), 1.42(12H, br s), 2.55–2.65(1H, m), 2.70–2.90(1H, m), 3.02(2H, t, J=8.5Hz), 3.35–3.45(2H, m), 3.66(2H, t, J=8.5Hz), 3.80–4.25(5H, m), 4.32(1H, br s), 6.80–7.10(6H, m)

Reference Example 15

In a similar manner to that described in Reference Example 14, the following compounds were prepared by hydrolyzing the corresponding acetyl compounds.

To a solution of 5-[2-[N-tert-butoxycarbonyl-2-(2-ethoxyphenoxy)ethylamino]propyl]indoline-7-carbonitrile (120 mg) in dimethyl sulfoxide (2.5 ml) was added 30% hydrogen peroxide (0.26 ml), and the mixture was stirred at room temperature for 15 minutes. Then, to the reaction mixture was added a 5N sodium hydroxide solution (0.26 ml), and the mixture was stirred at room temperature for 1.5 hours. To the reaction mixture was added acetic acid. The mixture was diluted with water and extracted with ethyl acetate. The extract was washed with a saturated aqueous sodium bicarbonate solution and water, dried over anhydrous magnesium sulfate. The solvent was evaporated under reduced pressure to give 127 mg of 5-[2-[N-tert-butoxycarbonyl-2-(2-ethoxyphenoxy)ethylamino]propyl]indoline-7-carboxamide as an oil.

IR (neat): $\nu$C=O 1687, 1659 cm$^{-1}$
NMR (CDCl$_3$)
$\delta$: 1.28(3H, t, J=7.1Hz), 1.36(3H, s), 1.41(9H, s), 2.50–2.70(1H, m), 2.80–2.90(1H, m), 2.95–3.00(2H, m), 3.40–3.50(2H, m), 3.65(2H, t, J=8.4Hz), 3.90–4.00(1H, m), 4.05–4.15(4H, m), 5.20–6.10(2H, m), 6.24(1H, br s), 6.80–7.05(6H, m)

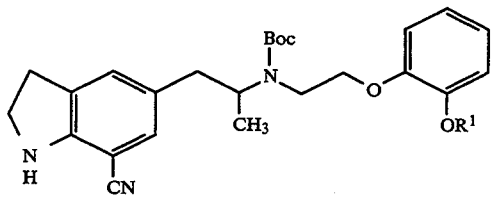

| R$^1$ | IR (cm$^{-1}$) | Specific rotation*) [α]$_D^{25}$ | NMR (δ, CDCl$_3$) |
|---|---|---|---|
| benzyl | 1680 (C=O) | | 1.16(3H, d, J=6.8Hz), 1.42(9H, s), 2.50(1H, dd, J=16.0, 8.0Hz), 2.70–2.90(.1H, m), 2.98(2H, br s), 3.30 – 3.55(2H, m), 3.65(2H, t, J=8.4Hz), 3.85–4.20(3H, m), 4.30(1H, s), 5.11(2H, br s), 6.80–7.10(6H, m), 7.25–7.50(5H, m) |
| 2,2,2-trifluoroethyl | 3360 (NH) 2200 (CN) 1665 (C=O) | | 1.24(3H, d, J=6.8Hz), 1.43(9H, s), 2.57(1H, dd, J=13.8, 6.7Hz), 2.70–2.95(1H, m), 3.01(2H, t, J=8.4 Hz), 3.30–3.55(2H, m), 3.66(2H, t, J=8.4Hz), 3.80–4.15(3H, m), 4.36(2H, q, J=8.4Hz), 6.80–7.15(6H, m) |
| 2,2,2-trifluoroethyl | similar to that of the racemate | −56.6° (c=1.14, MeOH) | similar to that of the racemate |
| 2,2,2-trifluoroethyl | similar to that of the racemate | +55.2° (c=1.09, MeOH) | similar to that of the racemate |
| ethyl | similar to that of the compound in Reference Example 14 | −62.5° (c=1.05, MeOH) | similar to that of the compound in Reference Example 14 |
| isopropyl | 3348 (NH) 2208 (CN) 1672 (C=O) | | 1.24(3H, d, J=6.4Hz), 1.33(6H, d, J=6.0Hz), 1.42(9H, s), 2.57(1H, dd, J=13.7, 7.0Hz), 2.75–2.90(1H, m), 3.01(2H, t, J=8.3Hz), 3.30–3.55(2H, m), 3.66(2H, t, J=8.5Hz), 3.85–4.25(3H, m), 4.48(1H, sept, J=6.0 Hz), 6.80–7.15(6H, m) |
| butyl | 3345 (NH) 2215 (CN) 1673 (C=O) | | 0.96(3H, t, J=7.4Hz), 1.23(3H, d, J=6.8Hz), 1.40–1.60(11H, m), 1.70–1.85(2H, m), 2.57(1H, dd, J=13.7, 7.0Hz), 2.75–2.95(1H, m), 3.01(2H, t, J=8.4Hz), 3.30–3.55(2H, m), 3.66(2H, t, J=8.4Hz), 3.85–4.35 (6H, m), 6.80–7.15(6H, m) |

*)blank means a racemate

Reference Example 16

5-[2-[N-tert-butoxycarbonyl-2-(2-ethoxyphenoxy)ethylamino]propyl]indoline-7-carboxamide Reference Example 17

In a similar manner to that described in Reference Example 16, the following compounds were prepared by converting the cyano group into the carbamoyl group.

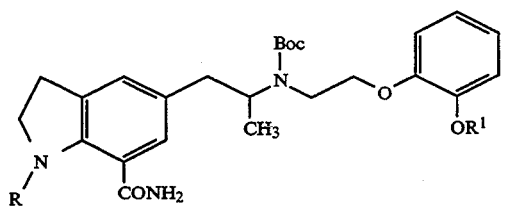

| R | R¹ | IR (cm⁻¹) | Specific rotation*²⁾ $[\alpha]_D^{25}$ | NMR (δ, CDCl₃) |
|---|---|---|---|---|
| hydrogen | 2,2,2-trifluoro-ethyl | 3423 (NH) 1658 (C=O) | | 1.25(3H, br s), 1.41(9H, s), 2.45–3.10(4H, m), 3.30–3.55(2H, m), 3.65(2H, t, J=8.5Hz), 3.80–4.15 (3H, m), 4.36(2H, q, J=8.4Hz), 5.50(1H, br s), 6.20(1H, br s), 6.80–7.30(6H, m) |
| hydrogen | 2,2,2-trifluoro-ethyl | similar to that of the racemate | +38.1° (c=1.15, MeOH) | similar to that of the racemate |
| hydrogen | 2,2,2-trifluoro-ethyl | similar to that of the racemate | +42.9° (c=1.16, MeOH) | similar to that of the racemate |
| hydrogen | benzyl | 1660 (C=O) | | 1.19(3H, d, J=6.7Hz), 1.40(9H, s), 2.45–2.65(1H, m), 2.70–2.85(1H, m), 2.90–3.00(2H, m), 3.30–3.55(2H, m), 3.63(2H, t, J=8.4Hz), 3.85–4.35(3H, m), 5.11(2H, br s), 5.45(1H, br), 6.25(1H, br), 6.75–7.00(6H, m), 7.25–7.45(6H, m) |
| hydrogen | isopropyl | 3417 (NH) 3350 (NH) 1686 (C=O) 1656 (C=O) | | 1.20–1.45(18H, m), 2.50–2.70(1H, m), 2.83(1H, dd, J=14.0, 8.9Hz), 2.90–3.05(2H, m), 3.30–3.55(2H, m), 3.64(2H, t, J=8.5Hz), 3.85–4.40(3H, m), 4.48 (1H, sept, J=6.1Hz), 5.60(1H, br), 6.24(1H, br s), 6.75–7.05(6H, m) |
| hydrogen | butyl | 3414 (NH) 1688 (C=O) 1656 (C=O) | | 0.96(3H, t, J=7.1Hz), 1.20–1.30(3H, m), 1.40(9H, s), 1.45–1.55(2H, m), 1.70–1.85(2H, m), 2.50–2.70(1H, m), 2.84(1H, dd, J=14.0, 8.9Hz), 2.90–3.00(2H, m), 3.30–3.60(2H, m), 3.64(2H, t, J=8.5 Hz), 3.85–4.40(5H, m), 5.60(1H, br), 6.30(1H, br), 6.75–7.05(6H, m) |
| carbamoyl-*¹⁾ methyl | ethyl | 3420 (NH) 3340 (NH) 3200 (NH) 1677 (C=O) | | 1.20–1.30(3H, m), 1.30–1.45(12H, m), 2.50–2.70 (1H, m), 2.75–3.05(3H, m), 3.35–4.40(11H, m), 5.84(1H, br s), 6.02(1H, br s), 6.43(1H, br s), 6.80–7.15(7H, m) |
| hydrogen | ethyl | similar to that of the compound in Reference Example 16 | −44.1° (c=1.04, MeOH) | similar to that of the compound in Reference Example 16 |

*¹⁾prepared from a cyanomethyl group in a similar manner.
*²⁾blank means a racemate Reference Example 18

5-[2-[N-tert-Butoxycarbonyl-2-(2-ethoxyphenoxy)ethylamino]propyl]-1-(3,4-dichlorobenzoyl)indoline-7-carbonitrile To a solution of 5-[2-[N-tert-butoxycarbonyl-2-(2-ethoxyphenoxy)ethylamino]propyl]indoline-7-carboxamide (97 mg) in methylene chloride (1 ml) and pyridine (1 ml) was added 3,4-dichlorobenzoyl chloride (84 mg), and the mixture was stirred at room temperature for 20 hours. The pH of the reaction mixture was adjusted to pH 7 with phosphate buffer solution, and the mixture was extracted with ethyl acetate. The extract was washed with water, and dried over anhydrous magnesium sulfate. The solvent was evaporated under reduced pressure, and the residue was purified by medium pressure liquid column chromatography on silica gel using a mixture of hexane and ethyl acetate (4/1) as eluent to give 98 mg of 5-[2-[N-tert-butoxycarbonyl-2-(2-ethoxyphenoxy)ethylamino]propyl]-1-(3,4-dichlorobenzoyl)indoline-7-carbonitrile as an oil.

IR (neat): υCN 2229 cm⁻¹ υC=O 1680 cm⁻¹
NMR (CDCl₃)
δ: 1.28(3H, d, J=6.5Hz), 1.40–1.50(12H, m), 2.70–2.80(1H, m), 3.00–3.10(3H, m), 3.40–3.60(2H, m), 3.90–4.30(7H, m), 6.80–7.00(4H, m), 7.20–7.40(2H, m), 7.50–7.60(2H, m), 7.82(1H, s)

Reference Example 19

In a similar manner to that described in Reference Example 18, the following compound was prepared by acylating the corresponding compound.

5-[2-[N-tert-Butoxycarbonyl-2-(2-ethoxyphenoxy)ethylamino]propyl]-1-trifluoroacetylindoline-7-carbonitrile.

IR (neat): υCN 2230 cm⁻¹ υC=O 1705, 1687 cm⁻¹
NMR (CDCl₃)
δ: 1.29(3H, d, J=7.1Hz), 1.43(12H, br s), 2.70–2.80(1H, m), 2.95–3.20(3H, m), 3.40–3.60(2H, m), 3.85–4.30(7H, m), 6.75–7.00 (4H, m), 7.30–7.45 (2H, m)

Reference Example 20

1-Acetyl-5-[2-[N-tert-butoxycarbonyl-2-(2-ethoxyphenoxy)ethylamino]propyl]indoline-7-carboxamide To a solution of 5-[2-[N-tert-butoxycarbonyl-2-(2-ethoxyphenoxy)ethylamino]propyl]indoline-7-carboxamide (50 mg) in dry methylene chloride (1 ml) were added triethylamine (21 mg) and acetic anhydride (21 mg), and the mixture was stirred at room temperature for 3.5 hours. To the reaction mixture was added water, and the mixture was extracted with methylene chloride.

The extract was washed with water and dried over anhydrous magnesium sulfate. The solvent was evaporated under reduced pressure to give 40 mg of 1-acetyl-5-[2-[N-tert-butoxycarbonyl-2-(2-ethoxyphenoxy)ethylamino]propyl]indoline-7-carboxamide as an amorphous powder.

IR (KBr): υNH 3340 cm$^{-1}$ υC=O 1678 cm$^{-1}$
NMR (CDCl$_3$)
δ: 1.20–1.30(3H, m), 1.41(12H, br s), 2.22(3H, s), 2.65–2.75(1H, m), 2.90–3.10(3H, m), 3.41(1H, s), 3.51(1H, s), 3.95–4.15(7H, m), 5.40–6.00(2H, m), 6.85–7.25(6H, m)

Reference Example 21

5-[5-[2-[N-tert-Butoxycarbonyl-2-(2-ethoxyphenoxy)ethylamino]propyl]-7-carbamoylindolin-1-yl]-5-oxopentanoic acid To a solution of 5-[2-[N-tert-butoxycarbonyl-2-(2-ethoxyphenoxy)ethylamino]propyl]indoline-7-carboxamide (145 mg) in pyridine (0.5 ml) were added 4-dimethylaminopyridine (4 mg) and glutaric anhydride (51 mg), and the mixture was stirred at room temperature for 72 hours. The pH of the reaction mixture was adjusted to pH 7 with phosphate buffer solution, and the mixture was extracted with ethyl acetate. The extract was washed with water and dried over anhydrous magnesium sulfate. The solvent was evaporated under reduced pressure, and the residue was purified by medium pressure liquid column chromatography on silica gel using a mixture of chloroform and methanol (9/1) as eluent to give 154 mg of 5-[5-[2-[N-tert-butoxycarbonyl-2-(2-ethoxyphenoxy)ethylamino]propyl]-7-carbamoylindolin-1-yl]-5-oxopentanoic acid as an oil.

IR (neat): υC=O 1675 cm$^{-1}$

NMR (CDCl$_3$)
δ: 1.20–1.35(3H, m), 1.41(12H, br s), 1.95–2.10(2H, m), 2.40–2.80(5H, m), 2.90–3.10(3H, m), 3.30–3.60(2H, m), 3.90–4.40(8H, m), 6.10(1H, br), 6.88(4H, br s), 7.05–7.20(2H, m), 7.70(1H, br)

Reference Example 22

1-Benzoyl-5-[2-[N-tert-butoxycarbonyl-2-(2-ethoxyphenoxy)ethylamino]propyl]indoline-7-carboxamide To a solution of 5-[2-[N-tert-butoxycarbonyl-2-(2-ethoxyphenoxy)ethylamino]propyl]indoline-7-carboxamide (113 mg) in dry methylene chloride (1 ml) were added triethylamine (42 μl) and benzoyl chloride (26 μl) with stirring under ice cooling, and the mixture was stirred at room temperature for 2.5 hours. To the reaction mixture was added water, and the mixture was extracted with ethyl acetate. The extract was washed with water, and dried over anhydrous magnesium sulfate. The solvent was evaporated under reduced pressure, and the residue was purified by medium pressure liquid column chromatography on silica gel by using a mixture of chloroform and methanol (20/1) as eluent to give 108 mg of 1-benzoyl-5-[2-[N-tert-butoxycarbonyl-2-(2-ethoxyphenoxy)ethylamino]propyl]indoline-7-carboxamide as an oil.

IR (neat): υC=O 1700, 1670, 1640 cm$^{-1}$
NMR (CDCl$_3$)
δ: 1.15–1.30(3H, m), 1.35–1.50(12H, m), 2.65–2.80 (1H, m), 2.95–3.10(3H, m), 3.35–3.60(3H, m), 3.90–4.20(6H, m), 6.80–6.95(4H, m), 7.12(1H, s), 7.21 (1H, s), 7.40–7.55(3H, m), 7.70(2H, d, J=6.9Hz)

Reference Example 23

In a similar manner to that described in Reference Example 22, the following compounds were prepared by acylating the corresponding compounds.

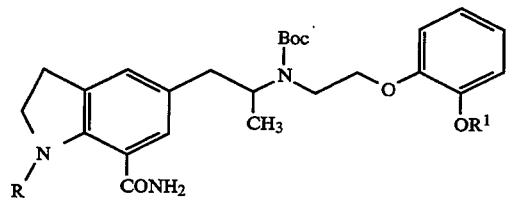

| R | R$^1$ | IR (cm$^{-1}$) | Specific rotation*) [α]$_D^{25}$ | NMR (δ, CDCl$_3$) |
|---|---|---|---|---|
| tert-butyl diphenyl-siloxy-acetyl | ethyl | 1677 (C=O) | | 1.10(9H, s), 1.26(3H, br s), 1.42(12H, br s), 2.60–2.80(1H, m), 2.90–3.10(3H, m), 3.35–3.60(2H, m), 3.90–4.40(7H, m), 4.41(2H, s), 5.20–5.80(2H, m), 6.89(4H, br s), 7.10–7.30(2H, m), 7.35–7.50(6H, m), 7.60–7.75(4H, m) |
| propionyl | ethyl | 3343 (NH) 1676 (C=O) | | 1.10–1.50(18H, m), 2.48(2H, q, J=7.4Hz), 2.60–2.70(1H, m), 2.90–3.10(3H, m), 3.40–3.60(2H, m), 3.90–4.20(7H, m), 5.40–5.80(2H, m), 6.80–6.90 (4H, br s), 7.05–7.20(2H, m) |
| butyryl | ethyl | 3200 (NH) 1676 (C=O) | | 0.99(3H, t, J=7.4Hz), 1.20–1.50(15H, m), 1.70–1.85(2H, m), 2.43(2H, t, J=7.3Hz), 2.60–2.80(1H, m), 2.90–3.10(3H, m), 3.30–3.60(2H, m), 3.90–4.40(7H, m), 5.30–5.90(2H, m), 6.80–6.90(4H, br s), 7.00–7.30(2H, m) |
| nicotinoyl | ethyl | 3320 (NH) 3180 (NH) 1676 (C=O) | | 1.20–1.35(3H, m), 1.43(12H, br s), 2.65–2.80(1H, m), 2.95–3.10(3H, m), 3.40–3.60(2H, m), 3.90–4.40(7H, m), 5.39(1H, br s), 5.48(1H, br s), 6.89 (4H, br s), 7.10–7.30(2H, m), 7.38(1H, t, J=7.3 Hz), 8.02(1H, d, J=7.8Hz), 8.71(1H, br s), 8.92 (1H, br s) |
| phenylacetyl | ethyl | 3350 (NH) 3200 (NH) 1679 (C=O) | | 1.24(3H, br t), 1.41(12H, br s), 2.60–2.75(1H, m), 2.85–3.05(3H, m), 3.30–3.40(2H, m), 3.85(2H, s), 3.90–4.40(7H, m), 5.70(2H, br), 6.87(4H, br s), 7.05–7.40(7H, m) |
| isobutyryl | ethyl | 3340 (NH) 3200 (NH) 1679 (C=O) | | 1.20–1.30(9H, m), 1.40(12H, br s), 2.60–3.10(5H, m), 3.30–3.60(2H, m), 3.90–4.40(7H, m), 5.60 (2H, br), 6.88(4H, br s), 7.15–7.25(2H, m) |

-continued

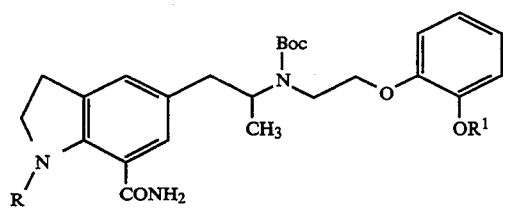

| R | R¹ | IR (cm⁻¹) | Specific rotation*) $[\alpha]_D^{25}$ | NMR (δ, CDCl₃) |
|---|---|---|---|---|
| 2-furoyl | ethyl | 3340 (NH) 1680 (C=O) | | 1.20-1.35(3H, m), 1.42(12H, br s), 2.65-2.80(1H, m), 2.90-3.15(3H, m), 3.40-3.60(2H, m), 3.90-4.50(7H, m), 5.45(1H, br), 5.85(1H, br), 6.52(1H, dd, J=3.5, 2.0Hz), 6.88(4H, br s), 7.10-7.30(3H, m), 7.55(1H, br s) |
| cyclohexyl-acetyl | ethyl | 3320 (NH) 3200 (NH) 1680 (C=O) | | 0.80-1.50(20H, m), 1.60-2.05(6H, m), 2.33(2H, d, J=6.9Hz), 2.50-2.70(1H, m), 2.90-3.10(3H, m), 3.35-3.60(2H, m), 3.90-4.40(7H, m), 5.50(1H, br), 5.80(1H, br), 6.88(4H, br s), 7.05-7.30(2H, m) |
| 3-butenoyl | ethyl | 1680 (C=O) | | 1.26(3H, t, J=7.1Hz), 1.35-1.45(12H, m), 2.65-2.80(1H, m), 2.90-3.10(3H, m), 3.27(2H, d, J=6.5 Hz), 3.35-3.55(3H, m), 3.90-4.25(6H, m), 5.15-5.30(2H, m), 5.60(2H, br), 5.95-6.10(1H, m), 6.80-6.95(4H, m), 7.05-7.25(2H, m) |
| 3-ethoxy-carbonyl-propionyl | ethyl | 1680 (C=O) | | 1.25(3H, t, J=6.9Hz), 1.27(3H, t, J=6.9Hz), 1.35-1.45(12H, m), 2.60-2.80(5H, m), 2.90-3.05(1H, m), 3.06(2H, t, J=7.8Hz), 3.35-3.60(2H, m), 3.90-4.40 (9H, m), 5.65(2H, br), 6.80-7.00(4H, m), 7.05-7.25(2H, m) |
| 3-furoyl | ethyl | 3350 (NH) 1681 (C=O) | | 1.20-1.35(3H, m), 1.45(12H, br s), 2.65-2.80(1H, m), 2.90-3.10(3H, m), 3.40-3.60(2H, m), 3.90-4.40(7H, m), 5.45(1H, br), 5.90(1H, br), 6.75-6.80(1H, m), 6.91(4H, br s), 7.10-7.30(2H, m), 7.47(1H, br s), 7.93(1H, s) |
| valeryl | ethyl | 3340 (NH) 3200 (NH) 1679 (C=O) | | 0.93(3H, t, J=7.4Hz), 1.15-1.30(3H, m), 1.41(13H, br s), 1.60-1.80(3H, m), 2.45(2H, t, J=7.4 Hz), 2.60-2.80(1H, m), 2.85-3.15(3H, m), 3.35-3.60 (2H, m), 3.90-4.40(7H, m), 5.60(2H, br), 6.88 (4H, br s), 7.05-7.20(2H, m) |
| hexanoyl | ethyl | 1675 (C=O) | | 0.85-0.95(3H, m), 1.26(4H, t, J=7.1Hz), 1.34(3H, s), 1.40-1.45(12H, m), 1.65-1.80(2H, m), 2.44 (2H, t, J=7.6Hz), 2.60-2.80(1H, m), 2.90-3.10 (3H, m), 3.41(1H, s), 3.51(1H, s), 3.90-4.20(7H, m), 5.40-5.90(2H, m), 6.87(4H, s), 7.00-7.25(2H, m) |
| ethoxy-acetyl | ethyl | 1678 (C=O) | | 1.20-1.30(6H, m), 1.35-1.45(12H, m), 2.70-2.75 (1H, m), 2.95-3.10(3H, m), 3.42(1H, br s), 3.53 (1H, br s), 3.62(2H, q, J=6.8Hz), 3.95-4.35(9H, m), 5.48(1H, br s), 5.88(1H, br s), 6.80-7.30 (6H, m) |
| butyryl | 2,2,2-trifluoro-ethyl | 3423 (NH) 3353 (NH) 1680 (C=O) | | 0.99(3H, t, J=7.4Hz), 1.26(3H, s), 1.42(9H, s), 1.70-1.85(2H, m), 2.43(2H, t, J=7.3Hz), 2.70(1H, br s), 2.85-3.10(3H, m), 3.30-3.60(3H, m), 3.80-4.20(4H, m), 4.36(2H, q, J=8.4Hz), 5.60(2H, br s), 6.80-7.25(6H, m) |
| buryryl | 2,2,2-trifluoro-ethyl | similar to that of the racemate | −39.8° (c=1.22, MeOH) | similar to that of the racemate |
| butyryl | 2,2,2-trifluoro-ethyl | similar to that of the racemate | +39.9° (c=1.13, MeOH) | similar to that of the racemate |
| acetyl | benzyl | 3340 (NH) 3200 (NH) 1678 (C=O) | | 1.19(3H, d, J=6.7Hz), 1.41(9H, s), 2.22(3H, s), 2.55-2.70(1H, m), 2.85-3.10(3H, m), 3.30-3.55 (2H, m), 3.90-4.35(5H, m), 5.10(2H, s), 5.60(2H, br), 6.80-6.95(4H, m), 7.00-7.20(2H, m), 7.25-7.45(5H, m) |
| acetyl | 2,2,2-trifluoro-ethyl | 3423 (NH) 1672 (C=O) | | 1.20-1.30(3H, m), 1.42(9H, s), 2.22(3H, s), 2.65-2.80(1H, m), 2.90-3.10(3H, m), 3.30-3.60(2H, m), 3.85-4.20(5H, m), 4.36(2H, q, J=8.4Hz), 5.60(2H, br s), 6.80-7.25(6H, m) |
| acetyl | isopropyl | 3435 (NH) 1683 (C=O) 1663 (C=O) | | 1.20-1.35(9H, m), 1.41(9H, s), 2.22(3H, s), 2.65-2.75(1H, m), 2.90-3.10(3H, m), 3.35-3.55(2H, m), 3.85-4.40(5H, m), 4.48(1H, sept, J=6.1Hz), 5.60 (2H, br), 6.80-6.95(4H, m), 7.05-7.25(2H, m) |
| butyryl | isopropyl | 3428 (NH) 1683 (C=O) | | 0.99(3H, t, J=7.4Hz), 1.20-1.35(9H, m), 1.41(9H, s), 1.70-1.80(2H, m), 2.43(2H, t, J=7.2Hz), 2.60-2.75(1H, m), 2.90-3.10(3H, m), 3.35-3.55(2H, m), 3.85-4.40(5H, m), 4.48(1H, sept, J=6.1Hz), 5.65 (2H, br), 6.80-6.95(4H, m), 7.05-7.25(2H, m) |
| butyryl | butyl | 3433 (NH) | | 0.90-1.05(6H, m), 1.20-1.30(3H, m), 1.41(9H, s), |

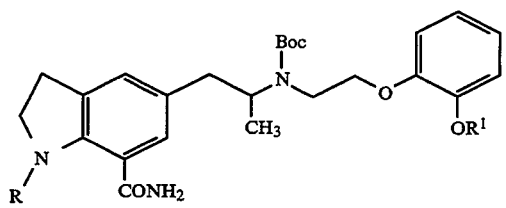

| R | R¹ | IR (cm⁻¹) | Specific rotation*) $[\alpha]_D^{25}$ | NMR (δ, CDCl₃) |
|---|---|---|---|---|
|  |  | 1684 (C=O) |  | 1.45–1.55(2H, m), 1.70–1.85(4H, m), 2.43(2H, t, J=7.3Hz), 2.60–2.85(1H, m), 2.90–3.10(3H, m), 3.35–3.65(2H, m), 3.85–4.40(7H, m), 5.60(2H, br), 6.80–6.95(4H, m), 7.05–7.25(2H, m) |
| acetyl | butyl | 3415 (NH) 1673 (C=O) |  | 0.96(3H, t, J=7.4Hz), 1.20–1.30(3H, m), 1.41(9H, s), 1.45–1.55(2H, m), 1.70–1.85(2H, m), 2.22(3H, s), 2.60–2.75(1H, m), 2.90–3.10(3H, m), 3.35–3.55(2H, m), 3.85–4.40(7H, m), 5.55(1H, br), 5.70(1H, br), 6.80–6.95(4H, m), 7.05–7.25(2H, m) |

*)blank means a racemate

Reference Example 24

Ethyl [5-[2-[N-tert-butoxycarbonyl-2-(2-ethoxyphenoxy)ethylamino]propyl]-7-cyanoindolin-1-yl]acetate To a solution of 5-[2-[N-tert-butoxycarbonyl-2-(2-ethoxyphenoxy)ethylamino]propyl]indoline-7-carbonitrile (300 mg) and cis-dicyclohexano-18-crown-6 (24 mg) in dry tetrahydrofuran (4 ml) were added potassium carbonate (107 mg) and ethyl bromoacetate (129 mg), and the mixture was reacted in a sealed tube at 100° C. for 24 hours. To the reaction mixture was added water, and the mixture was extracted with ethyl acetate. The extract was washed with water, and dried over anhydrous magnesium sulfate. The solvent was evaporated under reduced pressure, and the residue was purified by medium pressure liquid column chromatography on silica gel using a mixture of hexane and ethyl acetate (½) as eluent to give 124 mg of ethyl [5-[2-[N-tert-butoxycarbonyl-2-(2-ethoxyphenoxy)ethylamino]propyl]-7-cyanoindolin-1-yl]acetate as an oil.

IR (neat): νCN 2210 cm⁻¹
νC=O 1750, 1680 cm⁻¹
NMR (CDCl₃)
δ: 1.20–1.35(6H, m), 1.40(12H, br s), 2.50–2.60(1H, m), 2.75–2.90(1H, m), 2.96(2H, t, J=8.6Hz), 3.35–3.55(2H, m), 3.63(2H, t, J=8.6Hz), 3.90–4.30(7H, m), 4.35(2H, s), 6.80–7.10(6H, m)

Reference Example 25

In a similar manner to that described in Reference Example 24, the following compounds were prepared by alkylating the corresponding compounds.

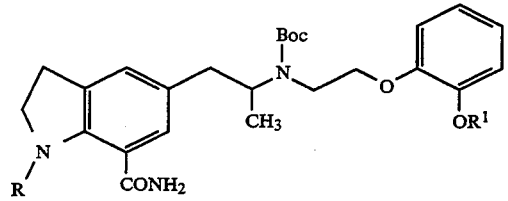

| R | R¹ | IR (cm⁻¹) | Specific rotation*) $[\alpha]_D^{25}$ | NMR (δ, CDCl₃) |
|---|---|---|---|---|
| ethoxycarbonylmethyl | ethyl | 1750 (C=O) 1680 (C=O) |  | 1.26(6H, t, J=7.1Hz), 1.35–1.45(12H, m), 2.55–2.70(1H, m), 2.75–2.95(1H, m), 3.01(2H, t, J=8.2 Hz), 3.35–3.65(4H, m), 3.85–4.15(7H, m), 4.17 (2H, q, J=7.2Hz), 5.50(1H, br), 6.75–7.15(6H, m), 7.20–7.25(1H, m) |
| benzyloxycarbonylmethyl | ethyl | 1750 (C=O) 1678 (C=O) |  | 1.25(3H, t, J=7.0Hz), 1.40(12H, br), 2.55–2.70 (1H, m), 2.75–2.90(1H, m), 3.02(2H, t, J=8.1Hz), 3.35–3.65(4H, m), 3.80–4.35(7H, m), 5.12(2H, s), 5.45(1H, br), 6.75–7.15(6H, m), 7.20–7.40(6H, m) |
| cyanomethyl | ethyl | 1665 (C=O) |  | 1.25–1.30(3H, m), 1.35–1.45(12H, m), 2.55–2.80 (1H, m), 2.85–2.90(1H, m), 2.95–3.00(2H, m), 3.40–3.60(4H, m), 3.90–4.15(4H, m), 4.20–4.35(1H, m), 4.45–4.60(2H, m), 5.50–5.65(1H, m), 6.40–6.60 (1H, m), 6.80–7.30(6H, m) |
| 3-ethoxycarbonylpropyl | ethyl | 3430 (NH) 3360 (NH) 3290 (NH) 1734 (C=O) 1678 (C=O) |  | 1.25(6H, t, J=7.1Hz), 1.40(12H, br s), 1.80–1.95 (2H, m), 2.34(2H, t, J=7.3Hz), 2.55–2.70(1H, m), 2.75–2.90(1H, m), 2.95(2H, t, J=8.3Hz), 3.00–3.10 (2H, m), 3.35–3.60(4H, m), 3.90–4.30(7H, m), 5.52 (1H, br s), 6.88(4H, br s), 6.95–7.15(2H, m), 7.30(1H, s) |
| 3-ethoxycarbonyl- | 2,2,2-trifluoro- | 3447 (NH) 3346 (NH) |  | 1.25(3H, t, J=7.1Hz), 1.39(3H, s), 1.58(9H, s), 1.80–1.95(2H, m), 2.34(2H, t, J=7.4Hz), 2.60–2.70 |

-continued

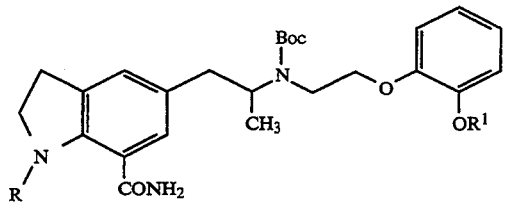

| R | R¹ | IR (cm⁻¹) | Specific rotation*) $[\alpha]_D^{25}$ | NMR (δ, CDCl₃) |
|---|---|---|---|---|
| propyl | ethyl | 1736 (C=O) 1673 (C=O) | | (1H, m), 2.75-2.90(1H, m), 2.95(2H, t, J=8.2 Hz), 3.04(2H, t, J=8.2Hz), 3.30-4.30(9H, m), 4.36(2H, q, J=8.4Hz), 5.53(1H, br s), 6.80-7.20(6H, m), 7.30(1H, s) |
| 3-iso-propoxy-carbonyl-propyl | 2,2,2-trifluoro-ethyl | 3440 (NH) 3390 (NH) 1729 (C=O) 1687 (C=O) | | 1.10-1.35(9H, m), 1.39(9H, s), 1.80-1.95(2H,m), 2.31(2H, t, J=7.4Hz), 2.55-3.20(5H, m), 3.30-4.30 (8H, m), 4.36(2H, q, J=8.5Hz), 4.90-5.10(1H, m), 5.60(1H, br s), 6.80-7.25(6H, m), 7.31(1H, s) |
| 3-methoxy-carbonyl-propyl | 2,2,2-trifluoro-ethyl | 3450 (NH) 3350 (NH) 1750 (C=O) 1670 (C=O) | −16.8° (c=1.45, MeOH) | 1.15-1.50(12H, m), 1.85-1.95(2H, m), 2.35(2H, t, J=7.3Hz), 2.55-3.10(6H, m), 3.30-3.60(4H, m), 3.67(3H, s), 3.75-4.20(3H, m), 4.36(2H, q, J=8.4 Hz), 5.54(1H, br s), 6.80-7.15(6H, m), 7.29(1H, br s) |
| 3-ethoxy-carbonyl-propyl | 2,2,2-trifluoro-ethyl | 3440 (NH) 3346 (NH) 1732 (C=O) 1675 (C=O) | −35.0° (c=1.02, MeOH) | 1.20-1.30(6H, m), 1.40(9H, s), 1.85-1.95(2H, m), 2.34(2H, t, J=7.3Hz), 2.60-2.70(1H, m), 2.75-2.90 (1H, m), 2.95(2H, t, J=8.2Hz), 3.04(2H, t, J=8.4 Hz), 3.35-3.60(4H, m), 3.85-4.30(5H, m), 4.36 (2H, q, J=8.4Hz), 5.51(1H, br s), 6.85-7.15(6H, m), 7.31(1H, s) |
| 3-benzyloxy-carbonyl-propyl | 2,2,2-trifluoro-ethyl | 3450 (NH) 3320 (NH) 1740 (C=O) 1670 (C=O) | −31.3° (c=1.10, MeOH) | 1.15-1.50(12H, m), 1.85-2.00(2H, m), 2.40(2H, t, J=7.3Hz), 2.55-3.10(6H, m), 3.25-3.65(4H, m), 3.80-4.20(3H, m), 4.36(2H, q, J=8.4Hz), 5.11(2H, s), 5.48(1H, br s), 6.80-7.15(6H, m), 7.20-7.40 (6H, m) |
| 3-propoxy-carbonyl-propyl | 2,2,2-trifluoro-ethyl | 3437 (NH) 3351 (NH) 3185 (NH) 1735 (C=O) 1676 (C=O) | −35.0° (c=1.01, MeOH) | 0.93(3H, t, J=7.4Hz), 1.25(3H, d, J=7.1Hz), 1.40 (9H, s), 1.55-1.70(2H, m), 1.85-1.95(2H, m), 2.34 (2H, t, J=7.4Hz), 2.60-2.70(1H, m), 2.75-2.90(1H, m), 2.95(2H, t, J=8.3Hz), 3.00-3.10(2H, m), 3.35-3.60(4H, m), 3.85-4.30(5H, m), 4.36(2H, q, J=8.4 Hz), 5.50(1H, br s), 6.85-7.15(6H, m), 7.30 (1H, s) |
| 3-butoxy-carbonyl-propyl | 2,2,2-trifluoro-ethyl | 3437 (NH) 3339 (NH) 1729 (C=O) 1672 (C=O) | −35.1° (c=1.03, MeOH) | 0.92(3H, t, J=7.4Hz), 1.15-1.65(14H, m), 1.85-1.95(2H, m), 2.34(2H, t, J=7.4Hz), 2.60-4.40(19H, m), 5.48(1H, br s), 6.85-7.35(7H, m) |
| 3-isopentyl-oxy-carbonyl-propyl | 2,2,2-trifluoro-ethyl | 1729 (C=O) 1673 (C=O) | −32.0° (c=1.19, MeOH) | 0.85-0.95(6H, m), 1.20-1.30(3H, m), 1.40(9H, s), 1.45-1.55(2H, m), 1.60-1.75(1H, m), 1.85-1.95 (2H, m), 2.33(2H, t, J=7.3Hz), 2.60-2.70(1H, m), 2.75-3.10(5H, m), 3.30-3.65(5H, m), 3.80-4.20 (4H, m), 4.36(2H, q, J=8.4Hz), 5.50(1H, br s), 6.85-7.20(6H, m), 7.30(1H, s) |
| ethoxy-carbonyl-methyl | 2,2,2-trifluoro-ethyl | 3448 (NH) 3355 (NH) 3195 (NH) 1746 (C=O) 1676 (C=O) | −37.1° (c=1.02, MeOH) | 1.20-1.30(6H, m), 1.41(9H, s), 2.55-2.70(1H, m) 2.80-2.95(1H, m), 3.01(2H, t, J=8.4Hz), 3.35-3.60 (4H, m), 3.85-4.30(7H, m), 4.36(2H, q, J=8.4Hz), 5.45(1H, br s), 6.70-7.10(6H, m), 7.26(1H, s) |
| 4-ethoxy-carbonyl-butyl | 2,2,2-trifluoro-ethyl | 3436 (NH) 1736 (C=O) 1672 (C=O) | −20.3° (c=1.04, MeOH) | 1.20-1.30(6H, m), 1.40(9H, s), 1.55-1.80(4H, m), 2.25-2.40(2H, m), 2.50-3.10(6H, m), 3.35-3.60 (4H, m), 3.80-4.30(5H, m), 4.36(2H, q, J=8.3Hz), 5.57(1H, br s), 6.80-7.20(6H, m), 7.30(1H, s) |
| 5-ethoxy-carbonyl-pentyl | 2,2,2-trifluoro-ethyl | 3425 (NH) 3352 (NH) 1735 (C=O) 1673 (C=O) | −31.8° (c=1.00, MeOH) | 1.15-1.35(6H, m), 1.39(9H, s), 1.45-1.75(6H, m), 2.20-2.40(2H, m), 2.55-3.05(6H, m), 3.35-3.60 (4H, m), 3.85-4.30(5H, m), 4.36(2H, q, J=8.8Hz), 5.53(1H, br s), 6.80-7.30(6H, m), 7.32(1H, s) |
| 3-isobutoxy-carbonyl-propyl | 2,2,2-trifluoro-ethyl | 3438 (NH) 3353 (NH) 1736 (C=O) 1673 (C=O) | −31.1° (c=0.99, MeOH) | 0.80-0.95(6H, m), 1.10-1.60(12H, m), 1.85-1.95 (3H, m), 2.36(2H, t, J=7.3Hz), 2.60-4.40(17H, m), 5.50(1H, br s), 6.85-7.30(7H, m) |
| carbamoyl-methyl | 2,2,2-trifluoro-ethyl | 3444 (NH) 1675 (C=O) | −41.8° (c=1.05, MeOH) | 1.20-1.30(3H, m), 1.37(9H, s), 2.55-3.10(4H, m), 3.30-4.10(9H, m), 4.36(2H, q, J=8.4Hz), 5.52(1H, s), 5.69(1H, br s), 6.35(1H, br s), 6.80-7.20 (7H, m) |
| 5-ethoxy-carbonyl-pentyl | isopropyl | 3451 (NH) 1736 (C=O) 1677 (C=O) | | 1.15-1.70(27H, m), 2.20-3.10(6H, m), 3.40-3.80 (5H, m), 3.90-4.40(6H, m), 4.47(1H, sept, J=6.1 Hz), 5.53(1H, br s), 6.85-7.35(7H, m) |
| 3-ethoxy-carbonyl-propyl | isopropyl | 3420 (NH) 3340 (NH) 1740 (C=O) 1680 (C=O) | | 1.20-1.45(21H, m), 1.85-1.95(2H, m), 2.34(2H, t, J=7.3Hz), 2.55-2.70(1H, m), 2.75-3.10(5H, m), 3.30-3.80(4H, m), 3.85-4.35(5H, m), 4.48(1H, sept, J=6.1Hz), 5.57(1H, br s), 6.80-7.20(6H, m), |

-continued

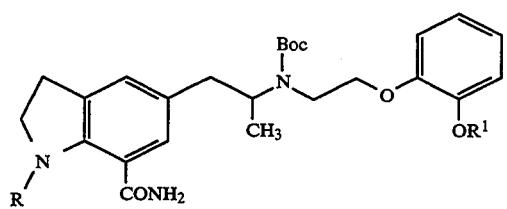

| R | R$^1$ | IR (cm$^{-1}$) | Specific rotation*) [α]$_D^{25}$ | NMR (δ, CDCl$_3$) |
|---|---|---|---|---|
| 3-propoxy-carbonyl-propyl | isopropyl | 3420 (NH)<br>3350 (NH)<br>1740 (C=O)<br>1680 (C=O) | | 7.25–7.35(1H, m)<br>0.93(3H, t, J=7.4Hz), 1.20–1.50(18H, m), 1.55–1.70(2H, m), 1.85–1.95(2H, m), 2.35(2H, t, J=7.4 Hz), 2.55–2.70(1H, m), 2.75–3.10(5H, m), 3.30–3.60(4H, m), 3.85–4.40(5H, m), 4.48(1H, sept, J=6.1Hz), 5.52(1H, br s), 6.80–7.15(6H, m), 7.30 (1H, br s) |
| 4-ethoxy-carbonyl-butyl | isopropyl | 3439 (NH)<br>3352 (NH)<br>1734 (C=O)<br>1675 (C=O) | | 1.20–1.45(21H, m), 1.55–1.75(4H, m), 2.25–2.40 (2H, m) 2.55–2.70(1H, m), 2.75–3.10(5H, m), 3.30–3.60(4H, m), 3.85–4.30(5H, m), 4.48(1H, sept, J=6.1Hz), 5.53(1H, br s), 6.80–7.20(6H, m), 7.31 (1H, br s) |
| 3-iso-pentyloxy-carbonyl-propyl | isopropyl | 3432 (NH)<br>3346 (NH)<br>3188 (NH)<br>1775 (C=O)<br>1733 (C=O)<br>1672 (C=O) | | 0.91(6H, d, J=6.3Hz), 1.10–2.00(23H, m), 2.20–4.60(18H, m), 5.60(1H, br s), 6.80–7.20(6H, m), 7.30(1H, br s) |
| 3-methoxy-carbonyl-propyl | isopropyl | 3430 (NH)<br>3350 (NH)<br>1750 (C=O)<br>1670 (C=O) | | 1.15–1.50(18H, m), 1.80–1.95(2H, m), 2.35(2H, t, J=7.3Hz), 2.55–3.10(6H, m), 3.30–3.60(4H, m), 3.67(3H, s), 3.80–4.20(3H, m), 4.40–4.55(1H, m), 5.53(1H, br s), 6.80–7.20(6H, m), 7.29(1H, br s) |
| 3-butoxy-carbonyl-propyl | isopropyl | 3428 (NH)<br>3345 (NH)<br>3191 (NH)<br>1775 (C=O)<br>1733 (C=O)<br>1672 (C=O) | | 0.92(3H, t, J=7.3Hz), 1.05–2.00(24H, m), 2.20–4.60(18H, m), 5.50(1H, br s), 6.75–7.20(6H, m), 7.31(1H, s) |
| 3-benzyloxy-carbonyl-propyl | isopropyl | 3450 (NH)<br>3350 (NH)<br>1780 (C=O)<br>1750 (C=O)<br>1680 (C=O) | | 1.15–1.50(18H, m), 1.80–2.00(2H, m), 2.40(2H, t, J=7.3Hz), 2.55–3.15(6H, m), 3.30–3.65(4H, m), 3.80–4.25(3H, m), 4.40–4.55(1H, m), 5.11(2H, s), 5.47(1H, br s), 6.75–7.15(6H, m), 7.20–7.40(6H, m) |
| 3-ethoxy-carbonyl-propyl | butyl | 3420 (NH)<br>3350 (NH)<br>1735 (C=O)<br>1680 (C=O) | | 0.96(3H, t, J=7.4Hz), 1.15–1.30(6H, m), 1.39(9H, s), 1.40–1.55(2H, m), 1.70–1.95(4H, m), 2.33(2H, t, J=7.3Hz), 2.55–2.70(1H, m), 2.75–3.10(5H, m), 3.30–3.60(4H, m), 3.85–4.30(7H, m), 5.48(1H, br s), 6.80–7.15(6H, m), 7.30(1H, s) |
| ethoxy-carbonyl-methyl | isopropyl | 3442 (NH)<br>3352 (NH)<br>1746 (C=O)<br>1672 (C=O) | | 1.23–1.30(6H, m), 1.32(6H, d, J=5.9Hz), 1.40(9H, s), 2.55–2.70(1H, m), 2.75–2.95(1H, m), 3.01(2H, t, J=8.4Hz), 3.35–3.50(2H, m), 3.55(2H, t, J=8.4 Hz), 3.85–4.35(8H, m), 4.40–4.55(1H, m), 5.47 (1H, br s), 6.60–7.15(6H, m) |
| 3-isobutoxy-carbonyl-propyl | isopropyl | 3431 (NH)<br>3353 (NH)<br>1736 (C=O)<br>1673 (C=O) | | 0.92(6H, d, J=6.8Hz), 1.20–1.60(20H, m), 1.80–2.00(1H, m), 2.35(2H, t, J=7.3Hz), 2.55–4.60(16H, m), 5.49(1H, br s), 6.85–7.30(7H, m) |

*)blank means a racemate

Reference Example 26

2-[2-[N-tert-Butoxycarbonyl-2-[2-(2,2,2-trifluoroethoxy)phenoxy]ethylamino]propyl-1-[2-(tert-butyldimethylsiloxy)ethyl]indoline-7-carboxamide To a solution of 5-[2-[N-tert-butoxycarbonyl-2-[2-(2,2,2-trifluoroethoxy)phenoxy]ethylamino]propyl]indoline-7-carboxamide (314 mg) and cis-dicyclohexano-18-crown-6 (108 mg) in dioxane (2.9 ml) were added potassium carbonate (400 mg) and 2-(tert-butyldimethylsiloxy) ethyl 4-nitrobenzenesulfonate (764 mg), and the mixture was stirred at 80° C. for 10 hours. To the reaction mixture was added water, and the mixture was extracted with ethyl acetate. The extract was washed with water, and dried over anhydrous magnesium sulfate. The solvent was evaporated under reduced pressure, and the residue was purified by medium pressure liquid column chromatography on silica gel using a mixture of hexane and ethyl acetate (1/1) as eluent to give 174 mg of 5-[2-[N-tert-butoxycarbonyl-2-[2-(2,2,2-trifluoroethoxy)phenoxy]ethylamino]propyl]-1-[2-(tert-butyldimethylsiloxy)ethyl]indoline-7-carboxamide as an oil.

IR (CHCl$_3$): υNH 3340, 3180 cm$^{-1}$ υC=O 1677 cm$^{-1}$

NMR (CDCl$_3$)

δ: 0.07(6H, s), 0.90(9H, s), 1.15–1.30(3H, m), 1.40(9H, s), 2.65(1H, dd, J=13.2, 5.5Hz), 2.75–3.05(3H, m), 3.15(2H, t, J=4.9Hz), 3.30–3.60(4H, m), 3.79(2H, t, J=5.5Hz), 3.85–4.35(3H, m), 4.36(2H, q, J=8.6Hz), 5.51(1H, br s), 6.80–7.20(5H, m), 7.40–7.55(2H, m)

Reference Example 27

In a similar manner to that described in Reference Example 26, the following compounds were prepared by alkylating the corresponding compounds.

5-[2-[N-tert-Butoxycarbonyl-2-(2-ethoxyphenoxy)ethylamino]propyl]-1-hydroxyacetylindoline-7-carbonitrile

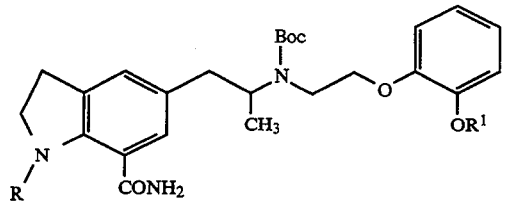

| R | R¹ | IR (cm⁻¹) | Specific rotation*) $[\alpha]_D^{25}$ | NMR (δ, CDCl₃) |
|---|---|---|---|---|
| 2-ethoxyethyl | ethyl | 3410 (NH) 3340 (NH) 3190 (NH) 1676 (C=O) | | 1.05–1.50(18H, m), 2.55–3.75(14H, m), 3.85–4.40(5H, m), 5.52(1H, br s), 6.88(4H, br s), 7.00–7.15(1H, m), 7.39(2H, br s) |
| 2-methoxyethyl | ethyl | 3410 (NH) 3340 (NH) 1676 (C=O) | | 1.10–1.55(15H, m), 2.55–3.10(4H, m), 3.15–3.75 (11H, m), 3.85–4.35(5H, m), 5.51(1H, br s), 6.88(4H, br s), 6.95–7.40(3H, m) |
| 2-(tert-butyldimethylsiloxy)ethyl | ethyl | 3340 (NH) 1675 (C=O) | | 0.06(6H, s), 0.90(9H, s), 1.26(3H, t, J=7.1Hz), 1.35–1.45(12H, m), 2.60–2.70(1H, m), 2.80–2.95 (1H, m), 2.97(2H, t, J=8.2Hz), 3.16(2H, t, J=5.5 Hz), 3.35–3.60(4H, m), 3.79(2H, t, J=5.5Hz), 3.85–4.30(5H, m), 5.47(1H, br s), 6.85–6.95 (4H, m), 7.00–7.15(1H, m), 7.40–7.50(1H, m) |
| 3-(tert-butyldimethylsiloxy)ethyl | ethyl | similar to that of the racemate | −38.6° (c=1.12, MeOH) | similar to that of the racemate |
| 3-(tert-butyldimethylsiloxy)propyl | ethyl | 3340 (NH) 3180 (NH) 1677 (C=O) | | 0.04(6H, s), 0.88(9H, s), 1.15–1.50(15H, m), 1.70–1.80(2H, m), 2.55–2.65(1H, m), 2.75–2.85 (1H, m), 2.95(2H, t, J=8.4Hz), 3.10(2H, t, J=8.0 Hz), 3.45(4H, br), 3.64(2H, t, J=6.2Hz), 3.85–4.35(5H, m), 5.48(1H, br s), 6.88(4H, br s), 6.95–7.35(3H, m) |
| 3-methoxypropyl | 2,2,2-trifluoroethyl | 3350 (NH) 1680 (C=O) | −50.5° (c=1.02, MeOH) | 1.25(3H, d, J=7.0Hz), 1.57(9H, s), 1.75–1.95(2H, m), 2.50–3.15(6H, m), 3.31(3H, s), 3.35–3.65(6H, m), 3.80–4.20(3H, m), 4.36(2H, q, J=8.4Hz), 5.53 (1H, br s), 6.80–7.25(6H, m), 7.33(1H, s) |
| 2-(tert-butyldimethylsiloxy)ethyl | 2,2,2-trifluoroethyl | 3340 (NH) 3180 (NH) 1677 (C=O) | −34.4° (c=1.01, MeOH) | 0.06(6H, s), 0.90(9H, s), 1.25(3H, d, J=7.1Hz), 1.40(9H, s), 2.60–2.70(1H, m), 2.75–2.95(1H, m), 2.97(2H, t, J=8.3Hz), 3.16(2H, t, J=5.4Hz), 3.35–3.60(4H, m), 3.79(2H, t, J=5.5Hz), 3.80–4.30(3H, m), 4.36(2H, q, J=8.4Hz), 5.46(1H, br s), 6.85–7.15(5H, m), 7.35–7.50(2H, m) |
| 2-methoxyethyl | 2,2,2-trifluoroethyl | 3350 (NH) 1680 (C=O) | −45.2° (c=1.09, MeOH) | 1.23(3H, d, J=7.0Hz), 1.40(9H, s), 2.55–3.05(4H, m), 3.15–3.25(2H, m), 3.30–3.60(9H, m), 3.80–4.20(3H, m), 4.36(2H, q, J=8.4Hz), 5.57(1H, br s), 6.80–7.10(6H, m), 7.36(1H, s) |
| 3-(tert-butyldimethylsiloxy)propyl | 2,2,2-trifluoroethyl | 3344 (NH) 3180 (NH) 1677 (C=O) | −37.9° (c=1.02, MeOH) | 0.03(6H, s), 0.88(9H, s), 1.24(3H, d, J=7.3Hz), 1.39(9H, s), 1.70–1.85(2H, m), 2.55–2.90(2H, m), 2.95(2H, t, J=8.3Hz), 3.09(2H, t, J=7.3Hz), 3.35–3.60(4H, m), 3.64(2H, t, J=6.4Hz), 3.80–4.30(3H, m), 4.36(2H, q, J=8.3Hz), 5.51(1H, br s), 6.85–7.30(6H, m), 7.35(1H, s) |
| 3-(tert-butyldimethylsiloxy)propyl | 2,2,2-trifluoroethyl | 3380 (NH) 1676 (C=O) | | 0.03(6H, s), 0.88(9H, s), 1.24(3H, d, J=7.3Hz), 1.39(9H, s), 1.70–1.85(2H, m), 2.55–2.90(2H, m), 2.95(2H, t, J=8.3Hz), 3.09(2H, t, J=7.3Hz), 3.35–3.60(4H, m), 3.64(2H, t, J=6.4Hz), 3.80–4.30(3H, m), 4.36(2H, q, J=8.3Hz), 5.51(1H, br s), 6.85–7.30(6H, m), 7.35(1H, s) |
| 4-methoxybutyl | 2,2,2-trifluoroethyl | 3379 (NH) 1685 (C=O) | −40.8° (c=1.05, MeOH) | 1.25(3H, d, J=7.1Hz), 1.40(9H, s), 1.50–1.70(4H, m), 2.55–2.70(1H, m), 2.75–3.10(5H, m), 3.32(3H, s), 3.35–3.55(6H, m), 3.80–4.30(3H, m), 4.36(2H, q, J=8.4Hz), 5.53(1H, br s), 6.80–7.15(6H, m), 7.34(1H, s) |
| 4-benzyloxybutyl | 2,2,2-trifluoroethyl | 3346 (NH) 1677 (C=O) | −38.6° (c=1.01, MeOH) | 0.90–1.50(12H, m), 1.55–1.70(4H, m), 2.55–3.15 (6H, m), 3.25–3.65(6H, m), 3.75–4.30(3H, m), 4.36 (2H, q, J=8.4Hz), 4.49(2H, s), 5.50(1H, br s), 6.75–7.45(12H, m) |

*)blank means a racemate

Reference Example 28

To a solution of 5-[2-[N-tert-butoxycarbonyl-2-(2-ethoxyphenoxy)ethylamino]propyl]-1-(tert-butyldiphenylsiloxyacetyl)indoline-7-carboxamide (190 mg) in tetrahydrofuran (1 ml) was added a 1M solution of tetrabutylammonium fluoride in tetrahydrofuran (300 μl), and the mixture was stirred at room temperature for 30 minutes. To the reaction mixture was added water, and the mixture was extracted with ethyl acetate. The extract was washed with water, and dried over anhydrous magnesium sulfate. The solvent was evaporated under reduced pressure, and the residue was purified by medium pressure liquid column chromatography on silica gel using a mixture of chloroform and methanol (49/1) as eluent to give 86 mg of 5-[2-[N-tert-butoxycarbonyl-2-(2-ethoxyphenoxy)ethylamino]propyl]-1-hydroxyacetylindoline-7-carbonitrile as an amorphous powder.

IR (film): υOH 3230 cm$^{-1}$ υCN 2247 cm$^{-1}$ υC=O 1687, 1648 cm$^{-1}$

NMR (CDCl$_3$)

δ: 1.25–1.35(3H, m), 1.42(12H, br s), 2.65–3.60(6H, m), 3.85–4.35(7H, m), 4.55(2H, s), 6.70–6.90(4H, m), 7.30–7.80 (2H, m)

Reference Example 29

5-[2-[N-tert-Butoxycarbonyl-2-(2-ethoxyphenoxy)ethylamino]propyl]-1-(2-hydroxyethyl)indoline-7-carboxamide To a solution of 5-[2-[N-tert-butoxycarbonyl-2-(2-ethoxyphenoxy)ethylamino]propyl]-1-[2-(tert-butyldimethylsiloxy)ethyl]indoline-7-carboxamide (170 mg) in tetrahydrofuran (2 ml) was added a 1M solution of tetrabutylammonium fluoride in tetrahydrofuran (270 μl), and the mixture was stirred at room temperature for 1 hour. The reaction mixture was concentrated under reduced pressure. To the residue was added water, and the mixture was extracted with ethyl acetate. The extract was washed with water, and dried over anhydrous magnesium sulfate. The solvent was evaporated under reduced pressure, and the residue was purified by medium pressure liquid column chromatography on silica gel using ethyl acetate as eluent to give 114 mg of 5-[2-[N-tert-butoxycarbonyl-2-(2-ethoxyphenoxy)ethylamino]propyl]-1-(2-hydroxyethyl)indoline-7-carboxamide as an oil.

IR (neat): υOH 3420 cm$^{-1}$ υC=O 1665 cm$^{-1}$

NMR (CDCl$_3$)

δ: 1.15–1.30 (3H, m), 1.35–1.40(12H, m), 2.55–2.70(1H, m), 2.75–2.90(1H, m), 2.98 (2H, t, J=8.5Hz), 3.10–3.70(6H, m), 3.81(2H, t, J=5.1Hz), 3.85–4.15(5H, m), 4.35(1H, br), 5.58(1H, br s), 6.74–7.20 (7H,m)

Reference Example 30

In a similar manner to that described in Reference Example 29, the following compounds were prepared.

(R)-(−)-5-[2-[N-tert-butoxycarbonyl-2-[2-(2,2,2-trifluoroethoxy)phenoxy]ethylamino]propyl]-1-(3-hydroxypropyl)indoline-7-carboxamide IR (KBr): υNH, OH 3439 cm$^{-1}$ υC=O 1666 cm$^{-1}$ Specific rotation: [α]$_D^{25}$ −40.6° (c=1.00, MeOH)

NMR (CDCl$_3$)

δ: 1.20–1.30(3H, m), 1.38(9H, s), 1.75–1.85(2H, m), 2.55–2.90(2H, m), 2.95(2H, t, J=8.4Hz), 3.00–3.60(6H, m), 3.65–4.15(5H, m), 4.36(2H, q, J=8.4Hz), 5.67(1H, br s), 6.62(1H, br s), 6.85–7.20(6H, m)

(R)-(−)-5-[2-[N-tert-Butoxycarbonyl-2-[2-(2,2,2-trifluoroethoxy)phenoxy]ethylamino]propyl]-1-(2-hydroxyethyl)indoline-7-carboxamide IR (KBr): υNH, OH 3422 cm$^{-1}$ υC=O 1666 cm$^{-1}$ Specific rotation: [α]$_D^{25}$ −43.1° (c=1.01, MeOH)

NMR (CDCl$_3$)

δ: 1.15–1.30(3H, m), 1.38(9H, s), 2.55–3.05(5H, m), 3.10–3.65(6H, m), 3.75–4.10(4H, m), 4.36(2H, q, J=8.4Hz), 5.61(1H, br s), 6.65–7.20(7H, m)

5-[2-[N-tert-butoxycarbonyl-2-[2-(2,2,2-trifluoroethoxy)phenoxy]ethylamino]propyl]-1-(3-hydroxypropyl)indoline-7-carboxamide IR (KBr): υNH, OH 3427 cm$^{-1}$ υNH 3310 cm$^{-1}$ υC=O 1694 cm$^{-1}$ NMR (CDCl$_3$)

δ: 1.20–1.35(3H, m), 1.37(9H, s), 1.75–1.85(2H, m), 2.55–2.90(2H, m), 2.95(2H, t, J=8.3Hz), 3.00–3.60(7H, m), 3.65–4.30(5H, m), 4.36(2H, q, J=8.4Hz), 5.73(1H, s), 6.64(1H, br s), 6.85–7.20(6H, m)

Reference Example 31

1-Acetyl-5-[2-[N-tert-butoxycarbonyl-2-(2-hydroxyphenoxy)ethylamino]propyl]indoline-7-carboxamide To a solution of 1-acetyl-5-[2-[N-tert-butoxycarbonyl-2-(2-benzyloxyphenoxy)ethylamino]propyl]indoline-7-carboxamide (358 mg) in methanol (6 ml) was added 10% palladium on carbon (35 mg), and the mixture was stirred under an atmosphere of hydrogen at room temperature for 5 hours. After the catalyst was filtered off, and the filtrate was concentrated to dryness to give 273 mg of 1-acetyl-5-[2-[N-tert-butoxycarbonyl-2-(2-hydroxyphenoxy)ethylamino]propyl]indoline-7-carboxamide as an amorphous powder.

NMR (CDCl$_3$)

δ: 1.27(3H, d, J=6.9Hz), 1.45(9H, s), 2.22(3H, s), 2.55–2.80(1H, m), 2.85–3.10(3H, m), 3.25–3.45(1H, m), 3.50–3.70(1H, m), 3.80–4.20(5H, m), 5.45–5.95(2H, m), 6.65–6.95 (4H, m), 7.00–7.30(2H, m)

Reference Example 32

(R)-(−)-4-[5-[2-[N-tert-butoxycarbonyl-2-[2-(2,2,2-trifluoroethoxy)phenoxy]ethylamino]propyl]-7-carbamoylindolin-1-yl]butyramide To a solution of methyl (R)-(−)-4-[5-[2-[N-tert-butoxycarbonyl-2-[2-(2,2,2-trifluoroethoxy)phenoxy]ethylamino]propyl]-7-carbamoylindolin-1-yl]butyrate (187 mg) in a saturated ammonia in methanol (2 ml) was added sodium cyanide (2 mg), and the mixture was stirred in a sealed tube at 50° C. for 71 hours. The reaction mixture was concentrated under reduced pressure, and the residue was purified by medium pressure liquid column chromatography on silica gel using a mixture of methylene chloride, diethyl ether and methanol (5/5/1) as eluent to give 145 mg of (R)-(−)-4-[5-[2-[N-tert-butoxycarbonyl-2-[2-(2,2,2-trifluoroethoxy)phenoxy]ethylamino]propyl]-7-carbamoylindolin-1-yl]butyramide as an oil.

IR (neat): υNH 3430 cm$^{-1}$ υC=O 1670 cm$^{-1}$

NMR (CDCl$_3$)

δ: 1.10–1.50(12H, m), 1.80–2.00(2H, m), 2.28(2H, t, J=7.2Hz), 2.50–3.70(10H, m), 3.–80–4.20(3H, m), 4.36(2H, q,J=8.4Hz), 5.30(1H, br), 5.67(1H, br s), 6.03(1H, br s), 6.70–7.30(7H, m)

Specific rotation: [α]$_D^{25}$ −39.7° (c=1.01, MeOH)

Reference Example 33

In a similar manner to that descried in Reference Example 32, the following compounds were prepared.

4-[5-[2-[N-tert-butoxycarbonyl-2-(2-isopropoxyphenoxy)ethylamino]propyl]-7-carbamoylindolin-1-yl]butyramide IR (neat): υNH 3400 cm$^{-1}$ υC=O 1670 cm$^{-1}$ NMR (CDCl$_3$)

δ: 1.10–1.50(18H, m), 1.80–2.00(2H, m), 2.28(2H, t, J=7.1Hz), 2.50–3.65(10H, m), 3.80–4.20(3H, m), 4.35–4.60(1H, m), 5.30(1H, br s), 5.67(1H, br s), 6.08(1H, br s), 6.70–7.30(7H, m)

(R)-(−)-4-[5-[2-[N-tert-Butoxycarbonyl-2-[2-(2,2,2-trifluoroethoxy)phenoxy]ethylamino]propyl]-7-carbamoylindolin-1-yl]-N-methylbutyramide IR (neat): υNH 3450 cm⁻¹ υC=O 1660 cm⁻¹
NMR (CDCl₃)
δ: 1.10–1.50(12H, m), 1.80–2.00(2H, m), 2.22(2H, t, J=7.1Hz), 2.50–3.70(14H, m), 3.80–4.20(2H, m), 4.36(2H, q, J=8.4Hz), 5.60(1H, br), 6.08(1H, br s), 6.70–7.10(7H, m)

Specific rotation: [α]$_D^{25}$ −36.4° (c=1.03, MeOH)

4-[5-[2-[N-tert-butoxycarbonyl-2-(2-isopropoxyphenoxy)ethylamino]propyl]-7-carbamoylindolin-1-yl]-N-methylbutyramide IR (neat): υNH 3320 cm⁻¹ υC=O 1660 cm⁻¹
NMR (CDCl₃)
δ: 1.10–1.50(18H, m), 1.80–2.00(2H, m), 2.22(2H, t, J=7.1Hz), 2.50–3.70(13H, m), 3.80–4.20(3H, m), 4.40–4.60(1H, m), 5.59(1H, br s), 6.13(1H, br s), 6.70–7.30(7H, m)

Reference Example 34

(R)-(−)-1-Acetyl-5-[2-[2-[2-(2,2,2-trifluoroethoxy)phenoxy]ethylamino]propyl]indoline-7-carbonitrile To a solution of (±)-1-acetyl-5-[2-[2-[2-(2,2,2-trifluoroethoxy)phenoxy]ethylamino]propyl]indoline-7-carbonitrile (4.46 g) in ethanol (20 ml) was added (+)-mandelic acid (1.52 g), and the mixture was allowed to stand at room temperature. The precipitated crystals were collected by filtration. The obtained crystals were successively recrystallized a mixture of methanol and ethanol (35 ml/35 ml), a mixture of methanol and ethanol (28 ml/14 ml), methanol (15 ml) and methanol (13 ml) to give 740 mg of a salt of (R)-(−)-1-acetyl-5-[2-[2-[2-(2,2,2-trifluoroethoxy)phenoxy]ethylamino]propyl]indoline-7-carbonitrile with (+)-mandelic acid. To a mixture of ethyl acetate (50 ml) and a 10% aqueous sodium carbonate solution (50 ml) was added this salt, and the mixture was stirred at room temperature for 2 hours. The reaction mixture was extracted with ethyl acetate. The extract was sequentially washed with a 10% aqueous sodium carbonate solution, water, and dried over anhydrous magnesium sulfate. The solvent was evaporated under reduced pressure to give 494 mg of (R)-(−)-1-acetyl-5-[2-[2-[2-(2,2,2-trifluoroethoxy)phenoxy]ethylamino]propyl]indoline-7-carbonitrile melting at 57°–59° C.

Specific rotation: [α]$_D^{25}$ −21.3° (c=1.02, MeOH)
NMR: in agreement with Reference Example 8.

Reference Example 35

(S)-(+)-1-Acetyl-5-[2-[2-[2-(2,2,2-trifluoroethoxy)phenoxy]ethylamino]propyl]indoline-7-carbonitrile In a similar manner to that described in Example 34, 681 mg of (S)-(+)-1-acetyl-5-[2-[2-[2-(2,2,2-trifluoroethoxy)phenoxy]ethylamino]propyl]indoline-7-carbonitrile as an oil was prepared from 3.86 g of (±)-1-acetyl-5-[2-[2-[2-(2,2,2-trifluoroethoxy)phenoxy]ethylamino]propyl]indoline-7-carbonitrile and 1.27 g of (−)-mandelic acid.

Specific rotation: [α]$_D^{25}$ +21.3° (c=1.03, MeOH)
NMR: in agreement with Reference Example 34.

Reference Example 36

(−)-1-Acetyl-5-[2-[2-(2-ethoxyphenoxy)ethylamino]propyl]indoline-7-carbonitrile

In a similar manner to that described in Reference Example 34, 534 mg of (−)-1-acetyl-5-[2-[2-(2-ethoxyphenoxy)ethylamino]propyl]indoline-7-carbonitrile as an oil was prepared from 5.32 g of (±)-1-acetyl-5-[2-[2-(2-ethoxyphenoxy)ethylamino]propyl]indoline-7-carbonitrile and 1.99 g of (+)-mandelic acid.

Specific rotation: [α]$_D^{25}$ −15.9° (c=1.07, MeOH)
IR and NMR: in agreement with Reference Example 7.

Example 1

1-Acetyl-5-[2-[2-(2-ethoxyphenoxy)ethylamino]propyl]indoline-7-carboxamide (Compound 1)

To a mixture of trifluoroacetic acid (0.2 ml) and methylene chloride (0.2! ml) was added a solution of 1-acetyl-5-[2-[N-tert-butoxycarbonyl-2-(2-ethoxyphenoxy)ethylamino]propyl]indoline-7-carboxamide (40 mg) in methylene chloride (0.2 ml) with stirring under ice cooling, and the mixture was stirred at room temperature for 1.5 hours. To the reaction mixture was added a saturated aqueous sodium bicarbonate solution, and the mixture was extracted with methylene chloride. The extract was dried over anhydrous magnesium sulfate. The solvent was concentrated under reduced pressure, and the residue was purified by medium pressure liquid column chromatography on silica gel using a mixture of methylene chloride and methanol (10/1) as eluent to give 33 mg of 1-acetyl-5-[2-[2-(2-ethoxyphenoxy)ethylamino]propyl]indoline-7-carboxamide as an amorphous powder.

IR (KBr): υC=O1659, 1652 cm⁻¹
NMR (CDCl₃)
δ: 1.06(3H, d, J=6.3Hz), 1.38(3H, t, J=7.0Hz), 2.23(3H, s), 2.58(1H, dd, J=13.4, 7.0Hz), 2.78(1H, dd, J=13.4, 6.2Hz), 2.95–3.10(5H, m), 4.04(2H, q, J=7.0Hz), 4.05–4.20(4H, m), 5.35–6.00(2H, m), 6.80–6.95(4H, m), 7.13(1H, s), 7.21 (1H, s)

Example 2

In a similar manner to that described in Example 1, the following compounds were prepared by deprotecting Boc group from the corresponding compounds.

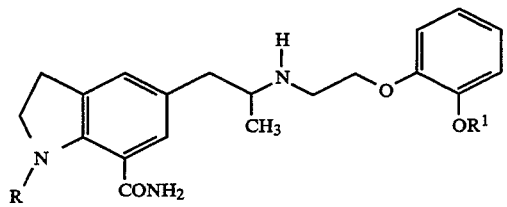

| Com. | R | R¹ | IR (cm⁻¹) | Specific rotation*) [α]$_D^{25}$ | NMR (δ, CDCl₃) |
|---|---|---|---|---|---|
| 2 | benzoyl | ethyl | 3350(NH) 1670(C=O) | | 1.26(3H, d, J=6.5Hz), 1.31(3H, t, J=7.0Hz), 2.79 (1H, dd, J=13.5, 8.7Hz), 2.92(2H, t, J=7.8Hz), 3.20 (1H, dd, J=13.5, 5.0Hz), 3.30–3.45(2H, m), 3.60– 3.65(1H, m), 3.98(2H, q, J=7.0Hz), 4.08(2H, t, J= |

-continued

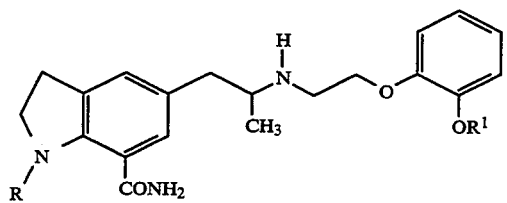

| Com. | R | R¹ | IR (cm⁻¹) | Specific rotation*) $[\alpha]_D^{25}$ | NMR (δ, CDCl₃) |
|---|---|---|---|---|---|
| | | | | | 7.8Hz), 4.24(2H, t, J=5.2Hz), 5.70–5.85(1H, m), 6.50–6.60(1H, m), 6.75–6.95(4H, m), 7.13(1H, s), 7.27(1H, s), 7.30–7.45(3H, m), 7.61(2H, d, J=7.1 Hz), 9.50–9.90(2H, m) |
| 3 | propionyl | ethyl | 3400(NH) 1655(C=O) | | 1.00–1.50(9H, m), 2.30–4.50(15H, m), 6.70–7.00 (4H, m), 7.20–7.50(2H, m), 9.30–9.80(2H, m) |
| 4 | butyryl | ethyl | 3341(NH) 1674(C=O) | | 0.99(3H, t, J=7.4Hz), 1.09(3H, d, J=6.3Hz), 1.38 (3H, t, J=7.0Hz), 1.70–1.90(2H, m), 2.44(2H, t, J= 7.3Hz), 2.60(1H, dd, J=13.4, 7.2Hz), 2.83(1H, dd, J=13.4, 6.2Hz), 3.00–3.20(5H, m), 4.00–4.20(6H, m), 5.40–5.90(2H, m), 6.80–7.00(4H, m), 7.13(1H, s), 7.21(1H, s) |
| 5 | nicotinoyl | ethyl | 3360(NH) 1666(C=O) | | 1.10(3H, d, J=6.2Hz), 1.40(3H, t, J=7.0Hz), 2.64 (1H, dd, J=13.5, 7.0Hz), 2.87(1H, dd, J=13.5, 6.6 Hz), 3.00–3.20(5H, m), 4.00–4.30(6H, m), 5.49 (1H, s), 5.99(1H, br s), 6.80–7.00(4H, m), 7.20 (1H, s), 7.26(1H, s), 7.38(1H, dd, J=7.8, 4.9Hz), 8.02(1H, d, J=7.8Hz), 8.71(1H, dd, J=4.9, 1.5Hz), 8.91(1H, br s) |
| 6 | phenyl-acetyl | ethyl | 3340(NH) 3190(NH) 1666(C=O) | | 1.07(3H, d, J=5.9Hz), 1.37(3H, t, J=7.4Hz), 2.59 (1H, dd, J=13.4, 6.9Hz), 2.82(1H, dd, J=13.4, 5.9 Hz), 2.90–3.15(5H, m), 3.85(2H, s), 3.95–4.20 (6H, m), 5.50–5.90(2H, m), 6.80–7.00(4H, m), 7.10 (1H, s), 7.20–7.40(6H, m) |
| 7 | isobutyryl | ethyl | 3310(NH) 3200(NH) 1666(C=O) | | 1.08(3H, d, J=5.9Hz), 1.21(6H, d, J=6.9Hz), 1.39 (3H, t, J=6.9Hz), 2.59(1H, dd, J=13.4, 7.4Hz), 2.75–2.90(2H, m), 2.95–3.20(5H, m), 4.00–4.30(6H, m), 5.70(2H, br), 6.80–7.00(4H, m), 7.14(1H, s), 7.22 (1H, s) |
| 8 | 2-furoyl | ethyl | 3377(NH) 3142(NH) 1679, 1638(C=O) | | 1.07(3H, d, J=5.9Hz), 1.39(3H, t, J=6.9Hz), 2.59 (1H, dd, J=13.4, 6.9Hz), 2.82(1H, dd, J=13.4, 5.9 Hz), 2.90–3.20(5H, m), 4.00–4.20(4H, m), 4.44 (2H, t, J=7.9Hz), 5.45(1H, br), 5.85(1H, br), 6.45–6.60(1H, m), 6.89(4H, br s), 7.15–7.20(2H, m), 7.26(1H, s), 7.55(1H, s) |
| 9 | cyclo-hexyl-acetyl | ethyl | 3370(NH) 3170(NH) 1670, 1655(C=O) | | 0.90–1.40(1H, m), 1.50–2.00(6H, m), 2.34(2H, d, J= 6.9Hz), 2.59(1H, dd, J=13.4, 7.4Hz), 2.84(1H, dd, J=13.4, 5.9Hz), 2.90–3.15(5H, m), 4.00–4.20(6H, m), 5.60(2H, br), 6.80–7.00(4H, m), 7.13(1H, s), 7.21(1H, s) |
| 10 | 3-butenoyl | ethyl | 3400(NH) 1670(C=O) | | 1.35(3H, t, J=7.1Hz), 1.39(3H, d, J=6.0Hz), 2.85–3.05(3H, m), 3.10–3.20(3H, m), 3.30–3.55(2H, m), 3.60–3.80(1H, m), 4.03(2H, q, J=7.1Hz), 4.11(2H, t, J=7.7Hz), 4.25(2H, t, J=4.4Hz), 5.10–5.25(2H, m), 5.85–6.25(3H, m), 6.80–7.05(4H, m), 7.16(1H, s), 7.26(1H, s), 8.80(2H, br s) |
| 11 | ethoxy-carbonyl-methyl | ethyl | 3420(NH) 1750, 1680(C=O) | | 1.23(3H, t, J=7.1Hz), 1.39(3H, t, J=7.0Hz), 1.43 (3H, d, J=6.5Hz), 2.85–3.05(4H, m), 3.35–3.45(2H, m), 3.50–3.60(2H, m), 3.65–3.70(1H, m), 3.90–4.30(8H, m), 5.64(1H, br s), 6.85–6.90(3H, m), 6.95–7.05 (3H, m), 7.25(1H, s) |
| 12 | ethoxy-carbonyl-propionyl | ethyl | 3350(NH) 1740, 1680(C=O) | | 1.06(3H, d, J=6.2Hz), 1.25(3H, t, J=7.1Hz), 1.39 (3H, t, J=7.0Hz), 2.57(1H, dd, J=13.3, 7.0Hz), 2.70–2.85(5H, m), 2.95–3.15(5H, m), 4.04(2H, q, J=7.0 Hz), 4.05–4.15(4H, m), 4.24(2H, t, J=7.9Hz), 5.45 (1H, br), 5.85(1H, br), 6.85–6.95(4H, m), 7.14 (1H, s), 7.24(1H, s) |
| 13 | 3-furoyl | ethyl | 3380(NH) 1679, 1630(C=O) | | 1.07(3H, d, J=6.4Hz), 1.40(3H, t, J=6.9Hz), 2.59 (1H, dd, J=13.4, 6.9Hz), 2.83(1H, dd, J=13.4, 5.9 Hz), 2.95–3.20(5H, m), 4.00–4.20(4H, m), 4.33 (2H, t, J=7.9Hz), 5.48(1H, br s), 5.93(1H, br s), 6.74(1H, br s), 6.85–7.00(4H, m), 7.17(1H, s), 7.25(1H, s), 7.45(1H, br s), 7.91(1H, s) |
| 14 | valeryl | ethyl | 1682, 1667(C=O) | | 0.93(3H, t, J=7.3Hz), 1.06(3H, d, J=6.3Hz), 1.35–1.50(5H, m), 1.65–1.75(2H, m), 2.45(2H, t, J=7.4 Hz), 2.50–2.65(1H, m), 2.75–2.90(1H, m), 3.00–3.10(5H, m), 4.00–4.20(6H, m), 5.30–5.95 (2H, m), 6.85–6.90(4H, m), 7.13(1H, s), 7.21(1H, s) |

-continued

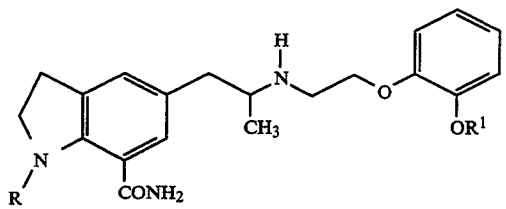

| Com. | R | R¹ | IR (cm⁻¹) | Specific rotation*) $[\alpha]_D^{25}$ | NMR (δ, CDCl₃) |
|---|---|---|---|---|---|
| 15 | benzyloxy-carbonyl-methyl | ethyl | 3390(NH) 1740, 1630(C=O) | | 1.11(3H, d, J=6.2Hz), 1.40(3H, t, J=7.0Hz), 2.56 (1H, dd, J=13.5, 7.2Hz), 2.79(1H, dd, J=13.5, 6.1 Hz), 2.95-3.15(5H, m), 3.57(2H, t, J=8.5Hz), 4.00-4.15(6H, m), 5.13(2H, s), 5.30(1H, br s), 6.54 (1H, br s), 6.85-6.95(4H, m), 7.04(1H, s), 7.22 (1H, s), 7.30-7.40(5H, m) |
| 16 | hexanoyl | ethyl | 1687, 1652(C=O) | | 0.85-0.95(3H, m), 1.07(3H, d, J=6.3Hz), 1.35(4H, br s), 1.40(3H, t, J=7.0Hz), 1.65-1.80(2H, m), 2.40-2.50(2H, m), 2.61(1H, dd, J=13.5, 5.8Hz), 2.79(1H, dd, J=13.5, 6.8Hz), 2.95-3.10(5H, m), 3.95-4.30(6H, m), 5.40-6.00(2H, m), 6.85-6.95 (4H, m), 7.13(1H, s), 7.21(1H, s) |
| 17 | ethoxy-acetyl | ethyl | 1650(C=O) | | 1.15(3H, d, J=6.3Hz), 1.21(3H, t, J=7.0Hz), 1.37 (3H, t, J=7.0Hz), 2.67(1H, dd, J=13.6, 7.3Hz), 2.91 (1H, dd, J=13.6, 6.0Hz), 3.04(2H, t, J=7.7Hz), 3.10-3.25(3H, m), 3.61(2H, q, J=7.0Hz), 4.03(2H, q, J= 7.0Hz), 4.10-4.15(4H, m), 4.22(2H, s), 5.95-6.50 (2H, m), 6.85-6.95(4H, m), 7.14(1H, s), 7.23(1H, s) |
| 18 | 2-ethoxy-ethyl | ethyl | 3316(NH) 1646(C=O) | | 1.08(3H, d, J=6.3Hz), 1.18(3H, t, J=7.0Hz), 1.40 (3H, t, J=7.0Hz), 2.53(1H, dd, J=16.0, 8.0Hz), 2.79 (1H, dd, J=16.0, 7.0Hz), 2.95-3.15(5H, m), 3.22 (2H, t, J=5.4Hz), 3.49(2H, q, J=7.0Hz), 3.53(2H, t, J=8.8Hz), 3.58(2H, t, J=5.4Hz), 4.00-4.20(4H, m), 5.51(1H, br s), 6.80-7.00(4H, m), 7.07(1H, s), 7.43(2H, br s) |
| 19 | 3-ethoxy-carbonyl-propyl | ethyl | 3420(NH) 3360(NH) 3190(NH) 1731, 1670(C=O) | | 1.08(3H, d, J=6.6Hz), 1.25(3H, t, J=7.2Hz), 1.40 (3H, t, J=7.1Hz), 1.75-2.00(2H, m), 2.33(2H, t, J= 7.7Hz), 2.53(1H, dd, J=12.8, 8.1Hz), 2.78(1H, dd, 12.8, 6.2Hz), 2.90-3.15(7H, m), 3.44(2H, t, J=8.8 Hz), 4.00-4.20(6H, m), 5.58(1H, br s), 6.80-7.00 (4H, m), 7.07(1H, s), 7.25(1H, br s), 7.36(1H, br s) |
| 20 | 2-methoxy-ethyl | ethyl | 3310(NH) 1645(C=O) | | 1.08(3H, d, J=6.0Hz), 1.40(3H, t, J=7.1Hz), 2.10 (1H, br), 2.54(1H, dd, J=13.1, 8.5Hz), 2.80(1H, dd, J=13.1, 6.5Hz), 2.90-3.10(5H, m), 3.22(2H, t, J=5.5Hz), 3.36(3H, s), 3.45-3.60(4H, m), 4.00-4.20(4H, m), 5.50(1H, br s), 6.80-7.00(4H, m), 7.08(1H, d, J=1.7Hz), 7.38(1H, br s), 7.42(1H, d, J=1.6Hz) |
| 21 | 2-hydroxy-ethyl | ethyl | 3400(NH) 1650(C=O) | | 1.13(3H, d, J=6.3Hz), 1.37(3H, t, J=7.0Hz), 2.60 (1H, dd, J=13.6, 6.6Hz), 2.73(1H, dd, J=13.6, 6.7 Hz), 2.98(2H, t, J=8.5Hz), 3.00-3.15(3H, m), 3.27 (2H, t, J=5.4Hz), 3.51(2H, t, J=8.5Hz), 3.80(2H, t, J=5.4Hz), 4.03(2H, q, J=7.0Hz), 4.05-4.20(2H, m), 5.73(1H, br s), 6.80-6.95(5H, m), 7.00(1H, s), 7.20(1H, s) |
| 22 | 3-hydroxy-propyl | ethyl | 3350(NH) 1656(C=O) | | 1.21(3H, d, J=6.4Hz), 1.38(3H, t, J=6.9Hz), 1.70-1.85(2H, m), 2.60-3.00(4H, m), 3.10-3.45(7H, m), 3.74(2H, t, J=5.4Hz), 4.03(2H, q, J=6.9Hz), 4.10-4.30(2H, m), 5.88(1H, br s), 6.80-7.00(6H, m), 7.18(1H, s) |
| 23 | acetyl | 2,2,2-tri-fluoro-ethyl | 3383(NH) 1644(C=O) | | 1.07(3H, d, J=6.2Hz), 2.23(3H, s), 2.58(1H, dd, J= 13.5, 6.8Hz), 2.75(1H, dd, J=13.5, 6.5Hz), 2.90-3.20(5H, m), 4.00-4.25(4H, m), 4.32(2H, q, J=8.4 Hz), 5.60(2H, br s), 6.85-6.95(2H, m), 6.97(1H, d, J=8.3Hz), 7.03(1H, t, J=7.7Hz), 7.12(1H, s), 7.21(1H, s) |
| 24 | butyryl | 2,2,2-tri-fluoro-ethyl | 3339(NH) 1672(C=O) | | 1.00(3H, t, J=7.5Hz), 1.07(3H, d, J=6.2Hz), 1.70-1.85(2H, m), 2.44(2H, t, J=7.3Hz), 2.58(1H, dd, J= 13.5, 6.9Hz), 2.76(1H, dd, J=13.5, 6.5Hz), 2.90-3.15(5H, m), 4.00-4.20(4H, m), 4.33(2H, q, J=8.4 Hz), 5.55(1H, br s), 5.85(1H, br s), 6.85-6.95 (2H, m), 6.97(1H, d, J=8.3Hz), 7.03(1H, t, J=7.7 Hz), 7.12(1H, s), 7.22(1H, s) |
| 25 | 2-hydroxy-ethyl | 2,2,2-tri-fluoro- | 3340(NH) 1655(C=O) | | 1.10(3H, d, J=6.4Hz), 2.35(1H, br s), 2.56(1H, dd, J=13.4, 6.4Hz), 2.70(1H, dd, J=13.4, 6.4Hz), 2.90-3.65(11H, m), 3.80(2H, t, J=5.4Hz), 4.00-4.20(2H, |

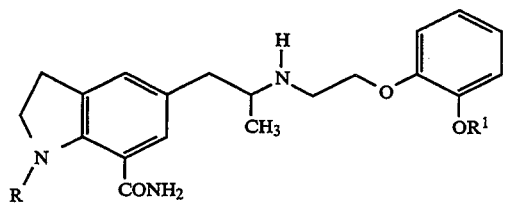

| Com. | R | R¹ | IR (cm⁻¹) | Specific rotation*) [α]$_D^{25}$ | NMR (δ, CDCl₃) |
|---|---|---|---|---|---|
| | | ethyl | | | m), 4.29(2H, q, J=8.4Hz), 5.90(1H, br s), 6.80–7.10(6H, m), 7.20(1H, s) |
| 26 | acetyl | benzyl | 3395(NH) 1668, 1655(C=O) | | 1.02(3H, d, J=6.2Hz), 2.20(3H, s), 2.53(1H, dd, J=13.6, 6.9Hz), 2.71(1H, dd, J=13.6, 6.4Hz), 2.90–3.10(5H, m), 4.05–4.20(4H, m), 5.06(2H, s), 5.60 (2H, br), 6.85–6.95(4H, m), 7.08(1H, s), 7.17(1H, br s), 7.25–7.40(5H, m) |
| 27 | cyano-methyl | ethyl | 1665(C=O) | | 1.08(3H, d, J=6.2Hz), 1.37(3H, t, J=7.0Hz), 2.57 (1H, dd, J=13.8, 6.8Hz), 2.75(1H, dd, J=13.8, 6.2 Hz), 2.95–3.10(5H, m), 3.57(2H, t, J=8.3Hz), 4.00–4.30(4H, m), 4.37(2H, s), 5.84(1H, br s), 6.61 (1H, br s), 6.85–6.95(4H, m), 7.10(1H, s), 7.23 (1H, s) |
| 28 | carbamoyl-methyl | ethyl | 3340(NH) 3200(NH) 1662(C=O) | | 1.15(3H, d, J=5.9Hz), 1.37(3H, t, J=7.4Hz), 2.63 (1H, dd, J=13.9, 6.4Hz), 2.77(1H, dd, J=13.9, 6.4 Hz), 2.96(2H, t, J=8.4Hz), 3.05–3.25(3H, m), 3.47 (2H, t, J=7.9Hz), 3.69(2H, br s), 4.02(2H, q, J=7.4 Hz), 4.05–4.25(2H, m), 6.15(1H, br), 6.30(1H, br), 6.75–7.20(8H, m) |
| 29 | 3-ethoxy-carbonyl-propyl | 2,2,2-tri-fluoro-ethyl | 3430(NH) 1673(C=O) | | 1.07(3H, d, J=6.2Hz), 1.25(3H, t, J=7.1Hz), 1.80–1.95(2H, m), 2.34(2H, t, J=7.4Hz), 2.52(1H, dd, J=13.5, 7.1Hz), 2.73(1H, dd, J=13.5, 6.3Hz), 2.90–3.15(7H, m), 3.44(2H, t, J=8.2Hz), 4.00–4.20(4H, m), 4.31(2H, q, J=8.4Hz), 5.69(1H, br s), 6.80–7.10(5H, m), 7.21(1H, br s), 7.36(1H, d, J=1.4Hz) |
| 30 | 3-isopropoxy-carbonyl-propyl | 2,2,2-tri-fluoro-ethyl | 3340(NH) 1721, 1665(C=O) | | 1.15(3H, d, J=6.3Hz), 1.22(6H, d, J=6.3Hz), 1.88 (2H, t, J=7.6Hz), 2.30(2H, t, J=7.4Hz), 2.61(1H, dd, J=13.7, 7.3Hz), 2.80(1H, dd, J=13.7, 6.3Hz), 2.90–3.60(9H, m), 4.05–4.20(2H, m), 4.34(2H, q, J=8.4Hz), 4.95–5.05(1H, m), 5.65(1H, br s), 6.80–7.10(6H, m), 7.34(1H, s) |
| 31 | butyryl | 2,2,2-tri-fluoro-ethyl | 3352(NH) 3132(NH) 1674, 1628(C=O) | −12.7° (c=0.99, MeOH) | similar to that of compound 24 |
| 32 | butyryl | 2,2,2-tri-fluoro-ethyl | similar to that of compound 31 | +13.0° (c=1.05, MeOH) | similar to that of compound 24 |
| 33 | 2-hydroxy-ethyl | ethyl | similar to that of compound 21 | −15.0° (c=1.10, MeOH) | similar to that of compound 21 |
| 34 | 3-methoxy-carbonyl-propyl | 2,2,2-tri-fluoro-ethyl | 3330(NH) 1740(C=O) 1650(C=O) | −16.8° (c=1.02, MeOH) | 1.06(3H, d, J=6.2Hz), 1.85–2.00(2H, m), 2.35(2H, t, J=7.3Hz), 2.52(1H, dd, J=13.5, 7.0Hz), 2.72(1H, dd, J=13.5, 6.3Hz), 2.90–3.15(7H, m), 3.44(2H, t, J=8.3Hz), 3.67(3H, s), 4.00–4.15(2H, m), 4.22 (2H, q, J=8.4Hz), 5.57(1H, br s), 6.80–7.20(6H, m), 7.35(1H, s) |
| 35 | 3-ethoxy-carbonyl-propyl | 2,2,2-tri-fluoro-ethyl | 3360(NH) 3110(NH) 1732(C=O) 1626(C=O) | −17.2° (c=1.00, MeOH) | 1.09(3H, d, J=6.3Hz), 1.25(3H, t, J=7.3Hz), 1.80–2.00(2H, m), 2.34(2H, t, J=7.3Hz), 2.54(1H, dd, J=13.6, 7.3Hz), 2.75(1H, dd, J=13.6, 5.9Hz), 2.90–3.15(7H, m), 3.44(2H, t, J=8.3Hz), 4.05–4.20(4H, m), 4.31(2H, q, J=8.3Hz), 5.58(1H, br s), 6.85–7.10(5H, m), 7.20–7.30(1H, m), 7.30(1H, s) |
| 36 | 2-hydroxy-ethyl | 2,2,2-tri-fluoro-ethyl | 3395(OH) 3200(NH) 1655(C=O) | −9.5° (c=0.99, MeOH) | 1.15(3H, d, J=6.3Hz), 2.55–2.80(2H, m), 2.96(2H, t, J=8.8Hz), 3.00–3.35(5H, m), 3.40–3.55(2H, m), 3.79(2H, t, J=5.4Hz), 4.10–4.20(2H, m), 4.30(2H, q, J=8.3Hz), 5.94(1H, br s), 6.85–7.05(6H, m), 7.19(1H, s) |
| 37 | 3-benzyloxy-carbonyl-propyl | 2,2,2-tri-fluoro-ethyl | 3350(NH) 1740(C=O) 1640(C=O) | −13.6° (c=1.07, MeOH) | 1.06(3H, d, J=6.2Hz), 1.85–2.00(2H, m), 2.40(2H, t, J=7.2Hz), 2.51(1H, dd, J=13.5, 7.0Hz), 2.72(1H, dd, J=13.5, 6.2Hz), 2.85–3.15(7H, m), 3.41 (2H, t, J=8.3Hz), 4.00–4.20(2H, m), 4.31(2H, q, J=8.4Hz), 5.11(2H, s), 5.51(1H, br s), 6.80–7.15(6H, m), 7.25–7.40(6H, m) |
| 38 | 3-propoxy-carbonyl- | 2,2,2-tri- | 3356(NH) 3076(NH) | −12.5° (c=1.00, MeOH) | 0.93(3H, t, J=7.4Hz), 1.06(3H, d, J=6.2Hz), 1.55–1.70(2H, m), 1.85–1.95(2H, m), 2.34(2H, t, J=7.4 |

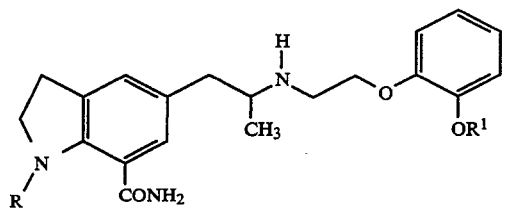

| Com. | R | R¹ | IR (cm⁻¹) | Specific rotation*) [α]$_D^{25}$ | NMR (δ, CDCl₃) |
|---|---|---|---|---|---|
|  | propyl | fluoro-ethyl | 1731(C=O) 1640(C=O) |  | Hz), 2.51(1H, dd, J=13.5, 7.0Hz), 2.72(1H, dd, J=13.5, 6.3Hz), 2.90–3.10(7H, m), 3.45(2H, t, J=8.3 Hz), 4.03(2H, t, J=6.7Hz), 4.05–4.15(2H, m), 4.31 (2H, q, J=8.4Hz), 5.54(1H, br s), 6.85–7.10(5H, m), 7.11(1H, br s), 7.35(1H, s) |
| 39 | 3-butoxy-carbonyl-propyl | 2,2,2-tri-fluoro-ethyl | 3346(NH) 3184(NH) 1729(C=O) 1666(C=O) | −11.7° (c=1.01, MeOH) | 0.92(3H, t, J=7.4Hz), 1.07(3H, d, J=6.2Hz), 1.30–1.45(2H, m), 1.55–1.70(2H, m), 1.85–2.00(2H, m), 2.34(2H, t, J=7.3Hz), 2.53(1H, dd, J=13.5, 7.0Hz), 2.73(1H, dd, J=13.5, 6.4Hz), 2.90–3.15(7H, m), 3.44(2H, t, J=8.2Hz), 4.00–4.15(4H, m), 4.31(2H, q, J=8.5Hz), 5.53(1H, br s), 6.85–7.20(6H, m), 7.36(1H, s) |
| 40 | 3-hydroxy-propyl | 2,2,2-tri-fluoro-ethyl | 3388(NH, OH) 3202(NH) 1637(C=O) | −14.0° (c=1.01, MeOH) | 1.08(3H, d, J=6.2Hz), 1.75–1.85(2H, m), 2.53(1H, dd, J=13.6, 6.7Hz), 2.68(1H, dd, J=13.6, 6.6Hz), 2.90–3.10(5H, m), 3.19(2H, t, J=6.7Hz), 3.41(2H, t, J=8.5Hz), 3.75(2H, t, J=5.6Hz), 4.05–4.15(2H, m), 4.30(2H, q, J=8.4Hz), 5.79(1H, br s), 6.65 (1H, br s), 6.85–7.05(5H, m), 7.16(1H, s) |
| 41 | 3-isopentyl-oxy-carbonyl-propyl | 2,2,2-tri-fluoro-ethyl | 3360(NH) 1729(C=O) 1638(C=O) | −13.1° (c=1.05, MeOH) | 0.91(6H, d, J=6.6Hz), 1.07(3H, d, J=6.2Hz), 1.51 (2H, q, J=6.9Hz), 1.60–1.75(1H, m), 1.85–1.95(2H, m), 2.33(2H, t, J=7.3Hz), 2.53(1H, dd, J=13.5, 7.0 Hz), 2.72(1H, dd, J=13.5, 6.3Hz), 2.90–3.10(7H, m), 3.44(2H, t, J=8.3Hz), 4.05–4.15(4H, m), 4.31 (2H, q, J=8.4Hz), 4.65–4.70(1H, m), 6.85–7.10(5H, m), 7.26(1H, s), 7.35(1H, s) |
| 42 | ethoxy-carbonyl-methyl | 2,2,2-tri-fluoro-ethyl | 3364(NH) 3189(NH) 1732(C=O) 1651(C=O) | −14.2° (c=1.03, MeOH) | 1.07(3H, d, J=6.2Hz), 1.26(3H, t, J=7.1Hz), 2.52 (1H, dd, J=13.5, 7.0Hz), 2.71(1H, dd, J=13.5, 6.3 Hz), 2.90–3.10(5H, m), 3.56(2H, t, J=8.5Hz), 3.94 (2H, s), 4.05–4.15(2H, m), 4.17(2H, q, J=7.1Hz), 4.32(2H, q, J=8.4Hz), 5.51(1H, br s), 6.75–7.10 (6H, m), 7.30(1H, s) |
| 43 | 4-ethoxy-carbonyl-butyl | 2,2,2-tri-fluoro-ethyl | 3345(NH) 3167(NH) 1736(C=O) 1657(C=O) | −12.2° (c=1.01, MeOH) | 1.07(3H, d, J=6.2Hz), 1.25(3H, t, J=7.1Hz), 1.55–1.70(4H, m), 2.32(2H, t, J=7.0Hz), 2.52(1H, dd, J=13.5, 7.0Hz), 2.73(1H, dd, J=13.5, 6.3Hz), 2.90–3.15(7H, m), 3.43(2H, t, J=8.2Hz), 4.05–4.15(4H, m), 4.31(2H, q, J=8.4Hz), 5.59(1H, br s), 6.85–7.10(5H, m), 7.20(1H, br s), 7.37(1H, s) |
| 44 | 3-carbamoyl-propyl | 2,2,2-tri-fluoro-ethyl | 3450(NH) 3330(NH) 1680(C=O) 1650(C=O) | −13.3° (c=1.01, MeOH) | 0.92(3H, d, J=6.2Hz) 1.60–1.80(2H, m), 2.05(2H, t, J=7.5HZ), 2.28(1H, dd, J=13.3, 7.8Hz), 2.64(1H, dd, J=13.3, 5.2Hz), 2.75–3.00(7H, m), 3.35(2H, t, J=8.5Hz), 4.03(2H, t, J=5.7Hz) 4.76(2H, q, J=9.0 Hz), 6.66(1H, br s), 6.80–7.30(8H, m), 7.59(1H, br s) |
| 45 | 3-(N-methyl-carbamoyl)-propyl | 2,2,2-tri-fluoro-ethyl | 3330(NH) 1670(C=O) 1650(C=O) | −13.0° (c=1.12, MeOH) | 1.06(3H, d, J=6.2Hz), 1.85–2.00(2H, m), 2.21(2H, t, J=7.1Hz), 2.52(1H, dd, J=13.5, 6.7Hz), 2.60–3.20(11H, m), 3.35–3.55(2H, m), 4.00–4.20(2H, m), 4.25–4.40(2H, m), 5.66(1H, br s), 5.97(1H, br s), 6.75–7.15(6H, m), 7.22(1H, br s) |
| 46 | 5-ethoxy-carbonyl-pentyl | 2,2,2-tri-fluoro-ethyl | 3407(NH) 3207(NH) 1732(C=O) 1639(=O) | −12.4° (c=1.01, MeOH) | 1.09(3H, d, J=6.2Hz), 1.25(3H, t, J=7.1Hz), 1.30–1.45(2H, m), 1.50–1.80(4H, m), 2.29(2H, t, J=7.4 Hz), 2.55(1H, dd J=13.5, 7.1Hz), 2.76(1H, dd, J=13.5, 6.4Hz), 2.90–3.15(7H, m), 3.43(2H, t, J=8.3 Hz), 4.05–4.20(4H, m), 4.32(2H, q, J=8.3Hz), 5.55 (1H, br s), 6.85–7.10(5H, m), 7.26(1H, br s), 7.38(1H, s) |
| 47 | 3-isobutoxy-carbonyl-propyl | 2,2,2-tri-fluoro-ethyl | 3346(NH) 3184(NH) 1729(C=O) 1666(C=O) | −11.4° (c=0.77, MeOH) | 0.92(6H, d, J=6.7Hz), 1.12(3H, d, J=6.3Hz), 1.85–1.95(2H, m), 2.35(2H, t, J=7.3Hz), 2.58(1H, dd, J=13.6, 6.8Hz), 2.80(1H, dd, J=13.6, 7.0Hz), 2.96 (2H, t, J=8.1Hz), 3.00–3.15(6H, m), 3.44(2H, t, J=8.7Hz), 3.85(2H, d, J=6.7Hz), 4.10–4.15(2H, m), 4.30–4.35(2H, m), 5.54(1H, br s), 6.90–7.10(5H, m), 7.16(1H, br s), 7.35(1H, s) |
| 48 | carbamoyl-methyl | 2,2,2-tri-fluoro-ethyl | 3432(NH) 3201(NH) 1677(C=O) 1643(C=O) | −15.0° (c=1.01, MeOH) | 1.08(3H, d, J=6.2Hz), 2.56(1H, dd, J=13.6, 6.5Hz), 2.66(1H, dd, J=13.6, 6.8Hz), 2.90–3.10(5H, m), 3.45–3.60(2H, m), 3.72(2H, s), 4.00–4.15(2H, m), 4.28(2H, q, J=8.4Hz), 5.59(1H, s), 5.80(1H, br s), 6.30(1H, br s), 6.80–7.10(7H, m) |
| 49 | 3-methoxy- | 2,2,2- | 3350(NH) | −15.7° | 1.06(3H, d, J=6.2Hz), 1.80–1.90(2H, m), 2.52(1H, |

-continued

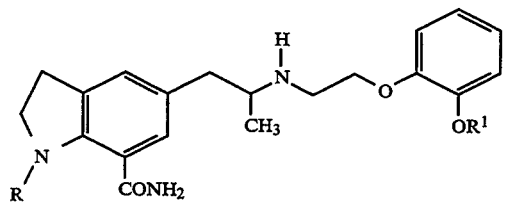

| Com. | R | R¹ | IR (cm⁻¹) | Specific rotation*) $[\alpha]_D^{25}$ | NMR (δ, CDCl₃) |
|---|---|---|---|---|---|
|  | propyl | tri-fluoro-ethyl | 1660(C=O) | (c=1.02, MeOH) | dd, J=13.5, 7.0Hz), 2.72(1H, dd, J=13.5, 6.3Hz), 2.85-3.20(7H, m), 3.31(3H, s), 3.41(2H, t, J=6.3 Hz), 3.45(2H, t, J=8.2Hz), 4.00-4.20(2H, m), 4.32 (2H, q, J=8.4Hz), 5.57(1H, br s), 6.80-7.10(5H, m), 7.20-7.35(1H, m), 7.39(1H, br s) |
| 50 | 3-hydroxy-propyl | 2,2,2-tri-fluoro-ethyl | 3350(NH) 3191(NH) 1656(C=O) |  | 1.09(3H, d, J=6.3Hz), 1.75-1.85(2H, m), 2.55(1H, dd, J=13.6, 6.6Hz), 2.69(1H, dd, J=13.6, 6.6Hz), 2.90-3.15(5H, m), 3.19(2H, t, J=6.7Hz), 3.41(2H, t, J=8.5Hz), 3.74(2H, t, J=5.7Hz), 4.05-4.20(2H, m), 4.30(2H, q, J=8.4Hz), 5.88(1H, br s), 6.71 (1H, br s), 6.85-7.10(5H, m), 7.16(1H, s) |
| 51 | 2-methoxy-ethyl | 2,2,2-tri-fluoro-ethyl | 3350(NH) 1660(C=O) | −16.6° (c=0.98, MeOH) | 1.07(3H, d, J=6.2Hz), 2.53(1H, dd, J=13.5, 7.1Hz), 2.74(1H, dd, J=13.5, 6.3Hz), 2.90-3.15(5H, m), 3.22(2H, t, J=5.4Hz), 3.36(3H, s), 3.52(2H, t, J=8.2Hz), 3.55(2H, t, J=5.4Hz), 4.05-4.20(2H, m), 4.32(2H, q, J=8.4Hz), 5.58(1H, br S), 6.85-7.10 (5H, m), 7.36(1H, br s), 7.42(1H, br s) |
| 52 | 4-methoxy-butyl | 2,2,2-tri-fluoro-ethyl | 3392(NH) 3205(NH) 1631(C=O) | −15.5° (c=1.01, MeOH) | 1.07(3H, d, J=6.2Hz), 1.50-1.70(4H, m), 2.53(1H, dd, J=13.5, 7.0Hz), 2.74(1H, dd, J=13.5, 6.4Hz), 2.90-3.15(7H, m), 3.32(3H, s), 3.38(2H, t, J=6.2 Hz), 3.44(2H, t, J=8.2Hz), 4.05-4.15(2H, m), 4.31(2H, q, J=8.6Hz), 5.56(1H, br s), 6.85-7.10 (5H, m), 7.30(1H, br s), 7.39(1H, s) |
| 53 | acetyl | iso-propyl | 3402(NH) 1664(C=O) |  | 1.06(3H, d, J=6.2Hz), 1.30(6H, d, J=6.1Hz), 2.24 (3H, s), 2.57(1H, dd, J=13.5, 7.2Hz), 2.79(1H, dd, J=13.5, 6.1Hz), 2.95-3.10(5H, m), 4.00-4.20(4H, m), 4.43(1H, sept, J=6.1Hz), 5.50(1H, br s), 5.86 (1H, br s), 6.85-6.95(4H, m), 7.13(1H, s), 7.20 (1H, br s) |
| 54 | butyryl | iso-propyl | 3416(NH) 1663(C=O) |  | 0.99(3H, t, J=7.3Hz), 1.09(3H, d, J=6.3Hz), 1.30 (6H, d, J=6.1Hz), 1.65-1.80(2H, m), 2.44(2H, t, J=7.3Hz), 2.59(1H, dd, J=13.4, 7.4Hz), 2.85(1H, dd, J=13.4, 5.9Hz), 3.00-3.15(5H, m), 4.05-4.20(4H, m), 4.44(1H, sept, J=6.1Hz), 5.65(1H, br), 5.90 (1H, br), 6.85-6.95(4H, m), 7.13(1H, s), 7.21(1H, s) |
| 55 | 3-ethoxy-carbonyl-propyl | iso-propyl | 3315(NH) 1737(C=O) 1645(C=O) |  | 1.06(3H, d, J=6.2Hz), 1.24(3H, t, J=7.1Hz), 1.30 (6H, d, J=6.1Hz), 1.85-1.95(2H, m), 2.33(2H, t, J=7.3Hz), 2.50(1H, dd, J=13.5, 7.3Hz), 2.75(1H, dd, J=13.5, 6.0Hz), 2.90-3.10(7H, m), 3.44(2H, t, J=8.3Hz), 4.00-4.15(4H, m), 4.41(1H, br s), 5.68 (1H, br s), 6.80-6.95(4H, m), 7.06 (1H, s), 7.20 (1H, br s), 7.35(1H, s) |
| 56 | butyryl | butyl | 3360(NH) 1673(C=O) |  | 0.94(3H, t, J=7.4Hz), 0.99(3H, t, J=7.4Hz), 1.05 (3H, d, J=6.3Hz), 1.40-1.55(2H, m), 1.70-1.85(4H, m), 2.44(2H, t, J=7.2Hz), 2.56(1H, dd, J=13.5, 7.2 Hz), 2.79(1H, dd, J=13.5, 5.9Hz), 2.95-3.10(5H, m), 3.97(2H, t, J=6.6Hz), 4.00-4.20(4H, m), 5.65 (2H, br), 6.80-6.95(4H, m), 7.12(1H, s), 7.21(1H, s) |
| 57 | 3-isopentyl-oxy-carbonyl-propyl | iso-propyl | 3386(NH) 1734(C=O) 1635(C=O) |  | 0.91(6H, d, J=6.6Hz), 1.06(3H, d, J=6.2Hz), 1.30 (6H, d, J=6.1Hz), 1.45-1.55(2H, m), 1.60-1.95(4H, m), 2.33(2H, t, J=7.2Hz), 2.51(1H, dd, J=13.5, 7.3 Hz), 2.75(1H, dd, J=13.5, 5.9Hz), 2.90-3.10(7H, m), 3.44(2H, t, J=8.2Hz), 4.00-4.15(4H, m), 4.35-4.45(1H, m), 5.53(1H, br s), 6.80-6.95(4H, m), 7.05(1H, s), 7.17(1H, br s), 7.35(1H, s) |
| 58 | 3-butoxy-carbonyl-propyl | iso-propyl | 3326(NH) 1735(C=O) 1642(C=O) |  | 0.92(3H, t, J=7.4Hz), 1.05(3H, d, J=6.2Hz), 1.30 (6H, d, J=6.1Hz), 1.30-1.45(2H, m), 1.55-1.70(3H, m), 1.85-1.95(2H, m), 2.34(2H, t, J=7.3Hz), 2.50 (1H, dd, J=13.6, 7.4Hz), 2.74(1H, dd, J=13.6, 5.9 Hz), 2.90-3.10(7H, m), 3.44(2H, t, J=8.3Hz), 4.00-4.15(4H, m), 4.35-4.45(1H, m), 5.51(1H, br s), 6.80-6.95(4H, m), 7.05(1H, s), 7.20(1H, br), 7.35 (1H, s) |
| 59 | 3-propoxy-carbonyl-propyl | iso-propyl | 3351(NH) 1732(C=O) 1635(C=O) |  | 0.93(3H, t, J=7.4Hz), 1.06(3H, d, J=6.2Hz), 1.30 (6H, d, J=6.1Hz), 1.55-1.70(2H, m), 1.85-1.95(2H, m), 2.35(2H, t, J=7.3Hz), 2.51(1H, dd, J=13.5, 7.3 |

-continued

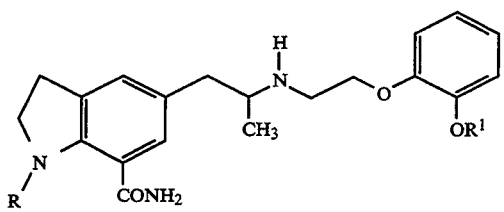

| Com. | R | R$^1$ | IR (cm$^{-1}$) | Specific rotation*) [α]$_D^{25}$ | NMR (δ, CDCl$_3$) |
|---|---|---|---|---|---|
| | | | | | Hz), 2.75(1H, dd, J=13.5, 6.0Hz), 2.90–3.10(7H, m), 3.44(2H, t, J=8.3Hz), 4.00–4.15(4H, m), 4.42 (1H, sept, J=6.1Hz), 5.53(1H, br s), 6.85–6.95 (4H, m), 7.06(1H, s), 7.18(1H, br s), 7.35(1H, s) |
| 60 | 3-ethoxy-carbonyl-propyl | butyl | 3391(NH) 3191(NH) 1726(C=O) 1635(C=O) | | 0.96(3H, t, J=7.4Hz), 1.09(3H, d, J=6.3Hz), 1.24 (3H, t, J=7.1Hz), 1.40–1.55(2H, m), 1.70–1.95(4H, m), 2.33(2H, t, J=7.3Hz), 2.50–2.60(1H, m), 2.70–2.85(1H, m), 2.90–3.15(7H, m), 3.44(2H, t, J=8.3 Hz), 3.97(2H, t, J=6.6Hz), 4.05–4.20(4H, m), 5.53 (1H, br s), 6.85–6.95(4H, m), 7.06(1H, s), 7.17 (1H, br s), 7.35(1H, s) |
| 61 | 3-methoxy-carbonyl-propyl | iso-propyl | 3350(NH) 1750(C=O) 1650(C=O) | | 1.06(3H, d, J=6.3Hz), 1.30(6H, d, J=6.1Hz), 1.85–2.00(2H, m), 2.35(2H, t, J=7.3Hz), 2.51(1H, dd, J=13.5, 7.2Hz), 2.74(1H, dd, J=13.5, 6.1Hz), 2.90–3.15(7H, m), 3.44(2H, t, J=8.3Hz), 3.67(3H, s), 4.00–4.20(2H, m), 4.35–4.50(1H, m), 5.55(1H, br-s), 6.80–6.95(4H, m), 7.00–7.25(2H, m), 7.34(1H, br s) |
| 62 | 3-benzyloxy-carbonyl-propyl | iso-propyl | 3350(NH) 1730(C=O) 1640(C=O) | | 1.05(3H, d, J=6.2Hz), 1.30(6H, d, J=6.1Hz), 1.85–2.00(2H, m), 2.40(2H, t, J=7.2Hz), 2.50(1H, dd, J=13.5, 7.2Hz), 2.74(1H, dd, J=13.5, 6.0Hz), 2.85–3.10(7H, m), 3.41(2H, t, J=8.3Hz), 4.00–4.15(2H, m), 4.35–4.50(1H, m), 5.11(2H, s), 5.53(1H, br s), 6.80–6.95(4H, m), 7.00–7.40(8H, m) |
| 63 | acetyl | butyl | 3392(NH) 3208(NH) 1663(C=O) | | 0.94(3H, t, J=7.4Hz), 1.07(3H, d, J=6.3Hz), 1.40–1.50(2H, m), 1.70–1.80(2H, m), 2.23(3H, s), 2.58 (1H, dd, J=13.5, 7.1Hz), 2.81(1H, dd, J=13.5, 6.0 Hz), 2.95–3.10(5H, m), 3.97(2H, t, J=6.6Hz), 4.05–4.20(4H, m), 5.50(1H, br), 5.80(1H, br), 6.85–6.95(4H, m), 7.13(1H, s), 7.22(1H, s) |
| 64 | 5-ethoxy-carbonyl-pentyl | iso-propyl | 3416(NH) 1725(C=O) 1648(C=O) | | 1.20–1.40(14H, m), 1.50–1.70(4H, m), 2.28(2H, t, J=7.4Hz), 2.70–2.80(1H, m), 2.90–3.05(5H, m), 3.20–3.50(5H, m), 4.12(2H, q, J=6.9Hz), 4.20–4.30 (2H, m), 4.40–4.55(1H, m), 5.66(1H, br s), 6.85–7.00(5H, m), 7.06(1H, s), 7.33(1H, s) |
| 65 | 4-ethoxy-carbonyl-butyl | iso-propyl | 3341(NH) 3182(NH) 1733(C=O) 1671(C=O) | | 1.07(3H, d, J=6.3Hz), 1.25(3H, t, J=7.1Hz), 1.30 (6H, d, J=6.1Hz), 1.55–1.70(4H, m), 2.31(2H, t, J=7.0Hz), 2.53(1H, dd, J=13.5, 7.3Hz), 2.76(1H, dd, J=13.5, 6.1Hz), 2.90–3.10(7H, m), 3.43(2H, t, J=8.3Hz), 4.05–4.20(4H, m), 4.42(1H, sept, J=6.1 Hz), 5.57(1H, br s), 6.80–6.95(4H, m), 7.05(1H, s), 7.20(1H, br s), 7.35(1H, s) |
| 66 | 3-(N-methyl-carbamoyl)-propyl | iso-propyl | 3320(NH) 1660(C=O) | | 1.06(3H, d, J=6.2Hz), 1.28(6H, d, J=6.1Hz), 1.80–2.00(2H, m), 2.21(2H, t, J=7.1Hz), 2.53(1H, dd, J=13.6, 6.7Hz), 2.60–2.80(4H, m) 2.90–3.15(7H, m), 3.43(2H, t, J=8.3Hz), 4.00–4.15(2H, m), 4.41(1H, sept, J=6.1Hz), 5.71(1H, br s), 6.09(1H, br s), 6.80–7.10(6H, m), 7.20(1H, br s) |
| 67 | 3-carbamoyl-propyl | iso-propyl | 3390(NH) 1670(C=O) | | 1.07(3H, d, J=6.2Hz), 1.29(6H, d, J=6.1Hz), 1.85–2.00(2H, m), 2.27(2H, t, J=7.1Hz), 2.54(1H, dd, J=13.6, 6.7Hz), 2.69(1H, dd, J=13.6, 6.4Hz), 2.90–3.20(7H, m), 3.44(2H, t, J=8.4Hz), 4.00–4.20(2H, m), 4.35–4.50(1H, m), 5.41(1H, br s), 5.83(1H, br s), 6.04(1H, br s), 6.80–7.10(6H, m), 7.21(1H, br s) |
| 68 | ethoxy-carbonyl-methyl | iso-propyl | 3399(NH) 1736(C=O) 1644(C=O) | | 1.07(3H, d, J=6.3Hz), 1.25(3H, t, J=7.3Hz), 1.31 (6H, d, J=6.3Hz), 2.51(1H, dd, J=13.2, 7.3Hz), 2.76 (1H, dd, J=13.2, 5.9Hz), 2.95–3.10(5H, m), 3.56 (2H, t, J=8.3Hz), 3.95(2H, s), 4.05–4.25(4H, m), 4.40–4.45(1H, m), 5.50(1H, br s), 6.80–6.95(5H, m), 7.06(1H, s), 7.30(1H, s) |
| 69 | 3-iso-butoxy-carbonyl-propyl | iso-propyl | 3339(NH) 3184(NH) 1729(C=O) 1673(C=O) | | 0.92(6H, d, J=6.7Hz), 1.08(3H, d, J=6.3Hz), 1.30 (6H, d, J=6.1Hz), 1.85–1.95(3H, m), 2.36(2H, t, J=7.3Hz), 2.53(1H, dd, J=13.7, 7.2Hz), 2.77(1H, dd, J=13.7, 5.9Hz), 2.95–3.10(7H, m), 3.45(2H, t, J=8.3Hz), 3.85(2H, d, J=6.7Hz), 4.05–4.15(2H, m), 4.43(1H, sept, J=6.1Hz), 5.51(1H, br s), 6.85–7.00(4H, m), 7.06(1H, s), 7.15–7.20(1H, m), 7.35 |

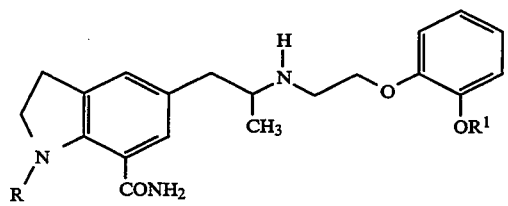

| Com. | R | R[1] | IR (cm[−1]) | Specific rotation*) [α]$_D^{25}$ | NMR (δ, CDCl$_3$) |
|---|---|---|---|---|---|
| | | | | | (1H, s) |

*blank means a racemate

Example 3

1-(2-Acetoxyethyl)-5-[2-[2-(2-ethoxyphenoxy)ethylamino]propyl]indoline-7-carboxamide (Compound 70)

To a solution of 5-[2-[N-tert-butoxycarbonyl-2-(2-ethoxyphenoxy)ethylamino]propyl]-1-(2-hydroxyethyl)indoline-7-carboxamide (60 mg) in methylene chloride (3 ml) were added triethylamine (24 μl) and acetic anhydride (13 μl) with stirring under ice cooling, and the mixture was stirred at room temperature for 16 hours. The reaction mixture was concentrated under reduced pressure and to the concentrate was added water. The mixture was extracted with ethyl acetate. The extract was washed with a saturated aqueous sodium bicarbonate solution and water, and dried over anhydrous magnesium sulfate. The solvent was evaporated under reduced pressure and the residue was dissolved in methylene chloride (2 ml). To the solution was added trifluoroacetic acid (0.5 ml), the mixture was stirred at room temperature for 30 minutes, and the reaction mixture was concentrated under reduced pressure. To the concentrate was added a saturated aqueous sodium bicarbonate solution, and the mixture was extracted with ethyl acetate. The extract was washed with water, and dried over anhydrous magnesium sulfate. The solvent was evaporated under reduced pressure, and the residue was purified by medium pressure liquid column chromatography on silica gel using a mixture of chloroform and methanol (7/1) as eluent to give 41 mg of 1-(2-acetoxyethyl)-5-[2-[2-(2-ethoxyphenoxy)ethylamino]propyl]indoline-7-carboxamide as an oil.

IR (neat): υNH 3350 cm$^{-1}$ υC=O 1740, 1670 cm$^{-1}$
NMR (CDCl$_3$)
δ: 1.07(3H, d, J=6.3Hz), 1.39(3H, t, J=7.0Hz), 2.05(3H, s), 2.53(1H, dd, J=13.5, 7.1Hz), 2.75(1H, dd, J=13.5, 6.1Hz), 2.90–3.10(5H, m), 3.32(2H, t, J=5.8Hz), 3.52 (2H, t, J=8.3Hz), 4.04 (2H, q, J=7.0Hz), 4.05–4.15(2H, m), 4.26(2H, t, J=5.8Hz), 5.57(1H, br s), 6.85–6.95 (4H, m), 7.07 (2H, br s), 7.36 (1H, s)

Example 4

In a similar manner to that described in Example 3, the following compounds were prepared.

(R)-(−)-1-(2-Acetoxyethyl)-5-[2-[2-(2,2,2-trifluoroethoxy)phenoxy]ethylamino]propyl]indoline-7-carboxamide (Compound 71)

IR (neat): υNH 3371, 3208 cm$^{-1}$ υC=O 1744, 1632 cm$^{-1}$

Specific rotation: [α]$_D^{25}$ −16.2° (c=1.01, MeOH)
NMR (CDCl$_3$)
δ: 1.09(3H, d, J=6.4Hz), 2.05(3H, s), 2.55(1H, dd, J=13.5, 7.0Hz), 2.75(1H, dd, J=13.5, 6.4Hz), 2.95–3.15(5H, m), 3.31(2H, t, J=5.8Hz), 3.52(2H, t, J=8.3Hz), 4.05–4.15(2H, m), 4.26(2H, t, J=5.8Hz), 4.31(2H, q, J=8.4Hz), 5.64(1H, br s), 6.85–7.10 (6H, m), 7.35(1H, s)

(R)-(−)-1-(3-Acetoxypropyl)-5-[2-[2-[2-(2,2,2-trifluoroethoxy)phenoxy]ethylamino]propyl]indoline-7-carboxamide (Compound 72)

IR (neat): υNH 3392, 3195 cm$^{-1}$ υC=O 1740, 1633 cm$^{-1}$

Specific rotation: [α]$_D^{25}$ −13.2° (c=1.00, MeOH)
NMR (CDCl$_3$)
δ: 1.08(3H, d, J=6.2Hz), 1.85–2.00(2H, m), 2.04(3H, s), 2.54(1H, dd, J=13.5, 7.0Hz), 2.73(1H, dd, J=13.5, 6.4Hz), 2.90–3.15(7H, m), 3.45(2H, t, J=8.3Hz), 4.05–4.15(4H, m), 4.31(2H, q, J=8.4Hz), 5.58(1H, br s), 6.85–7.15(6H, m), 7.35(1H, s)

Example 5

Sodium 5-[5-[2-[2-(2-ethoxyphenoxy)ethylamino]propyl]-7-carbamoylindolin-1-yl]-5-oxopentanoate (Compound 73)

In a similar manner to that described in Example 1, sodium 5-[5-[2-[2-(2-ethoxyphenoxy)ethylamino]propyl]-7-carbamoylindolin-1-yl]-5-oxopentanoate was prepared by removing a protective group by trifluoroacetic acid, and then treating with phosphate buffer solution.

IR (KBr): υNH 3400 cm$^{-1}$ υC=O 1687 cm$^{-1}$
NMR (DMSO-d$_6$)
δ: 1.14(3H, d, J=6.5Hz), 1.28(3H, t, J=7.0Hz), 1.70–1.85(2H, m), 2.29(2H, t, J=7.4Hz), 2.44(2H, t, J=7.2Hz), 2.55–2.70(1H, m), 3.02(2H, t, J=7.4Hz), 3.10–3.60 (4H, m), 4.03 (2H, q, J=7.0Hz), 4.08 (2H, t, J=8.0Hz), 4.23 (2H, t, J=5.3Hz), 6.85–7.10 (4H, m), 7.14(1H, s), 7.19(1H, s), 9.00(2H, br)

Example 6

Sodium 4-[5-[2-[2-(2-ethoxyphenoxy)ethylamino]propyl]-7-carbamoylindolin-1-yl]butyrate (Compound 74)

To a solution of ethyl 4-[5-[2-[2-(2-ethoxyphenoxy)ethylamino]propyl]-7-carbamoylindolin-1-yl]butyrate (88 mg) in ethanol (1 ml) was added a 1N aqueous sodium hydroxide solution (180 μl), and the mixture was stirred at room temperature for 6 hours. The reaction mixture was purified by medium pressure liquid column chromatography on ODS using a mixture of methanol and water (1/1) as eluent to give 51 mg of sodium 4-[5-[2-[2-(2-ethoxyphenoxy)ethylamino]propyl]-7-carbamoylindolin-1-yl]butyrate as an oil.

IR (neat): υNH 3423 cm$^{-1}$ υC=O 1662 cm$^{-1}$
NMR (CDCl$_3$)
δ: 0.99(3H, d, J=5.9Hz), 1.36(3H, t, J=6.9Hz), 1.70(2H, br s), 2.14(2H, br s), 2.37(1H, dd, J=13.4, 6.9Hz), 2.63(1H, dd, j=13.4, 5.9Hz), 2.70-3.10(7H, m), 3.15-3.35(2H, m), 3.90-4.15(4H, m), 6.84(6H, m), 7.01(1H, s), 7.90(1H, s)

Example 7

In a similar manner to that described in Example 6, the following compounds were prepared by hydrolyzing the corresponding ester compounds.

NMR: in agreement with Example 8.

Example 10

(R)-(−)-1-(4-Hydroxybutyl)-5-[2-[2-[2-(2,2,2-trifluoroethoxy)phenoxy]ethylamino]propyl]indoline-7-carboxamide (Compound 80)

To a solution of (R)-(−)-1-(4-benzyloxybutyl)-5-[2-[N-tert-butoxycarbonyl-2-[2-(2,2,2-trifluoroethoxy)-

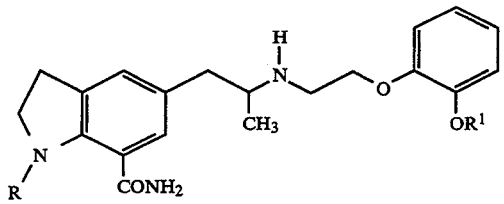

| Com. | R | R¹ | IR (cm⁻¹) | NMR(δ, DMSO-d₆) |
|------|---|-----|-----------|------------------|
| 75 | 3-carboxy-propionyl | ethyl | 3380(NH) 1670(C=O) | 0.94(3H, d, J=6.2Hz), 1.29(3H, t, J=7.0Hz), 2.35-2.55(3H, m), 2.63(2H, t, J=6.7Hz), 2.75(1H, dd, J=13.3, 5.5 Hz), 2.85-2.95(3H, m), 2.98(2H, t, J=8.0 Hz), 3.99(2H, q, J=7.0Hz), 4.00(2H, t, J=7.0Hz), 4.12(2H, t, J=7.8Hz), 6.85-7.00(5H, m), 7.08(1H, s), 7.15(1H, s), 7.22(1H, br s) |
| 76 | 3-sodium-carboxylato-propyl | 2,2,2-trifluoro-ethyl | 3423(NH) 1637, 1595(C=O) | 0.91(3H, d, J=6.2Hz), 1.60-1.75(2H, m), 1.85(2H, t, J=7.4Hz), 2.26(1H, dd, J=13.3, 7.9Hz), 2.63(1H, dd, J=13.3, 5.2Hz), 2.70-3.00(5H, m), 3.03(2H, t, J=7.7Hz), 3.35(2H, t, J=8.6Hz), 4.03(2H, t, J=5.7 Hz), 4.68(2H, q, J=9.0Hz), 6.80-7.10(6H, m), 7.30 (1H, s), 7.61(1H, s) |
| 77 | 3-carboxy-propyl | iso-propyl | 3420(NH) 1660(C=O) | 0.93(3H, d, J=6.2Hz), 1.22(6H, d, J=6.1Hz), 1.60-1.70(2H, m), 1.98(2H, t, J=7.4Hz), 2.30(1H, dd, J=13.3, 7.6Hz), 2.62(1H, dd, J=13.3, 5.4Hz), 2.75-2.95(5H, m), 3.05(2H, t, J=7.5Hz), 3.35(2H, t, J=8.5Hz), 3.95-4.05(2H, m), 4.44(1H, sept, J=6.1 Hz), 6.80-7.00(6H, m), 7.22(1H, s), 7.56(1H, s) |

Example 8

(R)-(−)-1-Acetyl-5-[2-[2-[2-(2,2,2-trifluoroethoxy)-phenoxyethylamino]propyl]indoline-7-carboxamide (Compound 78)

To a solution of (R)-(−)-1-acetyl-5-[2-[2-[2-(2,2,2-trifluoroethoxy)phenoxy]ethylamino]propyl]indoline-7-carbonitrile (2.00 g) in isopropanol (4.2 ml) was added concentrated hydrochloric acid (4.2 ml) slowly with stirring under ice cooling, and the mixture was stirred for 40 minutes. The reaction mixture was neutralized by a saturated aqueous sodium bicarbonate solution, and extracted with methylene chloride. The extract was washed with water, and dried over anhydrous magnesium sulfate. The solvent was evaporated under reduced pressure to give 1.70 g of (R)-(−)-1-acetyl-5-[2-[2-[2-(2,2,2-trifluoroethoxy)phenoxy]ethylamino]-propyl]indoline-7-carboxamide melting at 144°-146° C.

IR (KBr): υNH 3198 cm⁻¹ υC=O 1652 cm⁻¹

Specific rotation: [α]$_D^{25}$ −16.1° (c=1.20, MeOH)

NMR (CDCl₃)

δ: 1.07(3H, d, J=6.2Hz), 2.22(3H, s), 2.58(1H, dd, J=13.5, 6.8Hz), 2.75(1H, dd, J=13.5, 6.5Hz), 2.90-3.10(5H, m), 4.00-4.20(4H, m), 4.32(2H, q, J=8.4Hz), 5.60(2H, br s), 6.85-7.05(4H, m), 7.12(1H, s), 7.21(1H, s)

Example 9

In a similar manner to that described in Example 8, the following compound was prepared.

(S)-(+)-1-Acetyl-5-[2-[2-[2-(2,2,2-trifluoroethoxy)-phenoxy]ethylamino]propyl]indoline-7-carboxamide (Compound 79)

IR (KBr): υNH 3191 cm⁻¹ υC=O 1673, 1652 cm⁻¹

Specific rotation: [α]$_D^{25}$ +16.1° (c=1.19, MeOH)

phenoxy]ethylamino]propyl]indoline-7-carboxamide (523 mg) in methylene chloride (7.5 ml) was added dropwise trifluoroacetic acid (1.5 ml) with stirring under ice cooling, and the mixture was stirred at room temperature for 4 hours. To the reaction mixture was added a saturated aqueous sodium bicarbonate solution, and the mixture was extracted with ethyl acetate. The extract was dried over anhydrous magnesium sulfate. The solvent was evaporated under reduced pressure, and the residue was purified by medium pressure liquid column chromatography on silica gel using a mixture of chloroform and methanol (10/1) as eluent to give 388 mg of (R)-(−)-1-(4-benzyloxybutyl)-5-[2-[2-[2-(2,2,2-trifluoroethoxy)phenoxy]ethylamino]propyl]indoline-7-carboxamide melting at 101°-102° C.

IR (KBr): υNH 3343 cm⁻¹ υC=O 1627 cm⁻¹

Specific rotation: [α]$_D^{25}$ −12.3° (c=1.00, MeOH)

NMR (CDCl₃)

δ: 1.06(3H, d, J=6.2Hz), 1.55-1.80(4H, m), 2.52(1H, dd, J=13.5, 7.2Hz), 2.73(1H, dd, J=13.5, 6.2Hz), 2.90-3.10(7H, m), 3.43(2H, t, J=8.4Hz), 3.48(2H, t, J=6.1Hz), 4.05-4.15(2H, m), 4.31(2H, q, J=8.4Hz), 4.50(2H, s), 5.48(1H, br s), 6.85-7.10(5H, m), 7.20-7.40(7H, m)

To a solution of (R)-(−)-1-(4-benzyloxybutyl)-5-[2-[2-[2-(2,2,2-trifluoroethoxy)phenoxy]ethylamino]-propyl]indoline-7-carboxamide (200 mg) in ethanol (3.3 ml) were added a 1N hydrochloric acid (0.8 ml) and 10% palladium on carbon (20 mg), and the mixture was stirred at room temperature for 4 hours under an atmosphere of hydrogen. After the catalyst was filtered off, the filtrate was concentrated under reduced pressure.

To the concentrate were added water (12 ml) and sodium carbonate (106 mg), and the mixture was stirred for overnight at room temperature. The precipitated crystals were collected, washed with water, and dried at 50° C. under reduced pressure to give 160 mg of (R)-(−)-1-(4-hydroxybutyl)-5-[2-[2-[2-(2,2,2-trifluoroethoxy)phenoxy]ethylamino]propyl]indoline-7-carboxamide melting at 116°–118° C.

IR (KBr): υNH 3419, 3323 cm$^{-1}$ υC=O 1649 cm$^{-1}$
Specific rotation: $[\alpha]_D^{25}$ −14.4° (c=1.01, MeOH)
NMR (CDCl$_3$)

δ: 1.06(3H, d, J=6.2Hz), 1.50–1.80(4H, m), 2.52(1H, dd, J=13.5, 6.9Hz), 2.70(1H, dd, J=13.5, 6.4Hz), 2.85–3.10(7H, m), 3.45(2H, t, J=8.4Hz), 3.65(2H, t, J=6.1Hz), 4.00–4.15(2H, m), 4.31(2H, q, J=8.4Hz), 5.72(1H, br s), 6.85–7.t5(6H, m), 7.31(1H, s)

What is claimed is:

1. A compound represented by the formula:

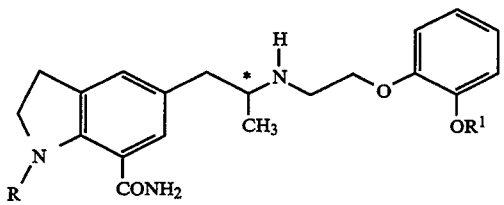

wherein R represents a saturated or unsaturated aliphatic acyl group which may be optionally substituted by a halogen atom, a hydroxy group, a lower alkoxy group, a carboxy group, a lower alkoxycarbonyl group, a cycloalkyl group or an aryl group; a hydroxyalkyl group; an aliphatic acyloxyalkyl group; a lower alkyl group which may be optionally substituted by a lower alkoxy group, a carboxy group, a lower alkoxycarbonyl group, an aryl substituted lower alkoxycarbonyl group, a carbamoyl group, a mono- or dialkyl substituted carbamoyl group or a cyano group; an aromatic acyl group which may be optionally substituted by a halogen atom; a furoyl group or a pyridylcarbonyl group; $R^1$ represents a lower alkyl group which may be optionally substituted by a halogen atom or an aryl group; the carbon atom marked with * represents a carbon atom in (R) configuration, (S) configuration or a mixture thereof; or a salt thereof.

2. A compound as claimed in claim 1, represented by the formula:

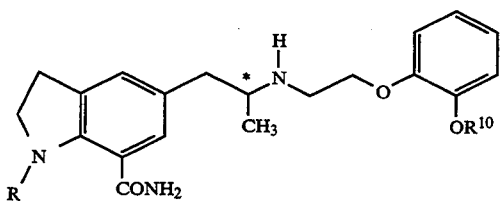

wherein R represents a saturated or unsaturated aliphatic acyl group which may be optionally substituted with a halogen atom, a hydroxy group, a lower alkoxy group, a carboxy group, a lower alkoxycarbonyl group, a cycloalkyl group or an aryl group; a hydroxyalkyl group; an aliphatic acyloxyalkyl group; a lower alkyl group which may be optionally substituted by a lower alkoxy group, a carboxy group, a lower alkoxycarbonyl group, an aryl substituted lower alkoxycarbonyl group, a carbamoyl group, a mono- or dialkyl substituted carbamoyl group or a cyano group; an aromatic acyl group which may be optionally substituted by a halogen atom; a furoyl group or a pyridylcarbonyl group; $R^{10}$ represents a lower alkyl group which may be optionally substituted by a halogen atom; the carbon atom marked with * represents a carbon atom in (R) configuration, (S) configuration or a mixture thereof; or a salt thereof.

3. A compound as claimed in claim 2, represented by the formula:

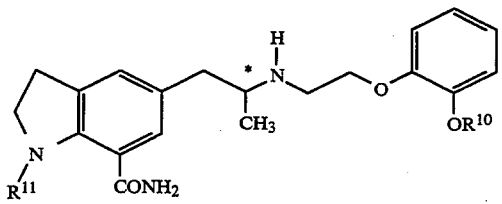

wherein $R^{11}$ represents a saturated or unsaturated aliphatic acyl group which may be optionally substituted by a carboxy group; a hydroxyalkyl group; an aliphatic acyloxyalkyl group or a lower alkyl group which may be optionally substituted by a lower alkoxy group, a carboxy group or a lower alkoxycarbonyl group; $R^{10}$ represents a lower alkyl group which may be optionally substituted by a halogen atom; the carbon atom marked with * represents a carbon atom in (R) configuration, (S) configuration or a mixture thereof; or a salt thereof.

4. A compound as claimed in claim 3, represented by the formula:

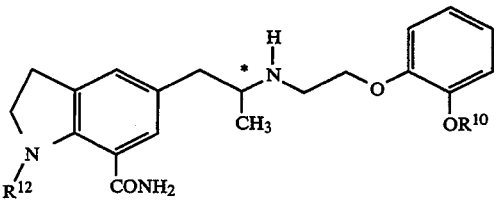

wherein $R^{12}$ represents a butyryl group, a 3-hydroxypropyl group, a 3-ethyoxycarbonylpropyl group or a 3-methoxypropyl group; $R^{10}$ represents a lower alkyl group which may be optionally substituted by a halogen atom; the carbon atom marked with * represents a carbon atom in (R) configuration, (S) configuration or a mixture thereof; or a salt thereof.

5. A compound as claimed in claim 4, represented by the formula:

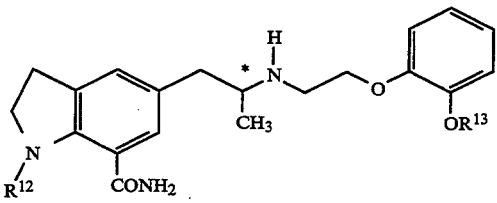

wherein $R^{12}$ represents a butyryl group, a 3-hydroxypropyl group, a 3-ethyoxycarbonylpropyl group or a 3-methoxypropyl group; $R^{13}$ represents a 2,2,2-trifluoroethyl group or an isopropyl group; the carbon atom marked with * represents a carbon atom in (R)

configuration, (S) configuration or a mixture thereof; or a salt thereof.

6. The compound as claimed in claim 5, represented by the formula:

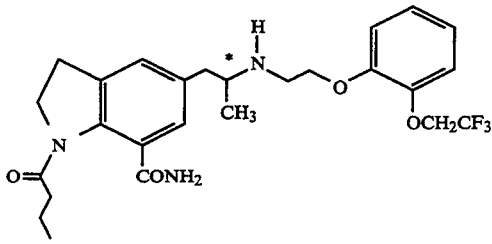

wherein the carbon atom marked with * represents a carbon atom in (R) configuration, (S) configuration or a mixture thereof; or a salt thereof.

7. The compound as claimed in claim 5, represented by the formula:

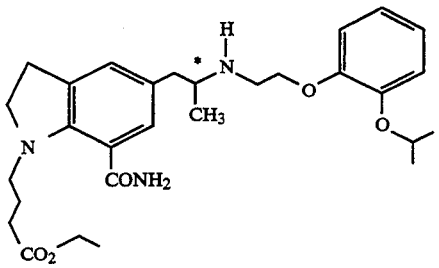

wherein the carbon atom marked with * represents a carbon atom in (R) configuration, (S) configuration or a mixture thereof; or a salt thereof.

8. The compound as claimed in claim 5, represented by the formula:

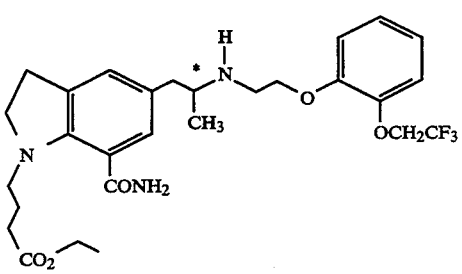

wherein the carbon atom marked with * represents a carbon atom in (R) configuration, (S) configuration or a mixture thereof; or a salt thereof.

9. The compound as claimed in claim 5, represented by the formula:

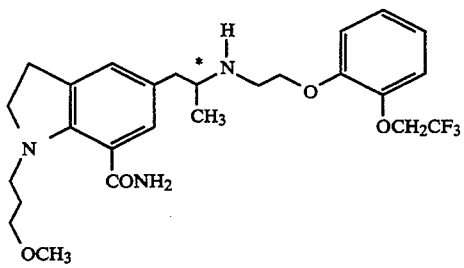

wherein the carbon atom marked with * represents a carbon atom in (R) configuration, (S) configuration or a mixture thereof; or a salt thereof.

10. The compound as claimed in claim 5, represented by the formula:

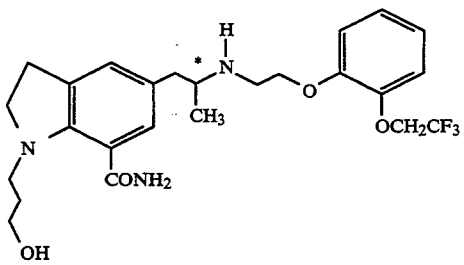

wherein the carbon atom marked with * represents a carbon atom in (R) configuration, (S) configuration or a mixture thereof; or a salt thereof.

11. The compound as claimed in claim 5, represented by the formula:

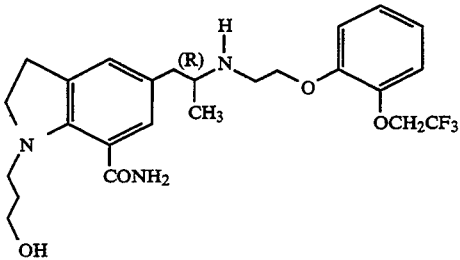

wherein the carbon atom marked with (R) represents a carbon atom in (R) configuration; or a salt thereof.

12. A pharmaceutical composition for the treatment of dysuria containing, as an active ingredient, a compound represented by the formula:

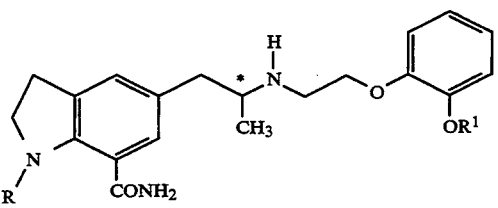

wherein R represents a saturated or unsaturated aliphatic acyl group which may be optionally substituted by a halogen atom, a hydroxy group, a lower alkoxy group, a carboxy group, a lower alkoxycarbonyl group, a cycloalkyl group or an aryl group; a hydroxyalkyl group; an aliphatic acyloxyalkyl group; a lower alkyl group which may be optionally substituted by a lower alkoxy group, a carboxy group, a lower alkoxycarbonyl group, an aryl substituted lower alkoxycarbonyl group, a carbamoyl group, a mono- or dialkyl substituted carbamoyl group or a cyano group; an aromatic acyl group which may be optionally substituted by a halogen atom; a furoyl group or a pyridylcarbonyl group; R¹ represents a lower alkyl group which may be optionally substituted by a halogen atom or an aryl group; the carbon atom marked with * represents a carbon atom in (R) configuration, (S) configuration or a mixture thereof; or a salt thereof.

13. A pharmaceutical composition as claimed in claim 12, wherein said active ingredient is represented by the formula:

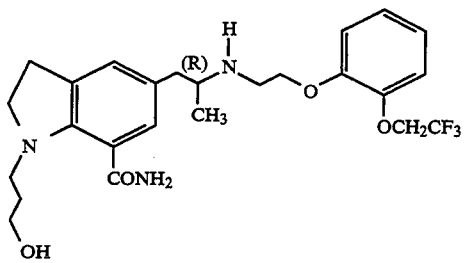

wherein the carbon atom marked with (R) represents a carbon atom in (R) configuration; or a salt thereof.

14. A method for the treatment of dysuria which comprises administering to a mammal or a human afflicted with dysuria a therapeutically effective amount of a compound of claim 1.

15. The method as claimed in claim 14, wherein said compound is represented by the formula:

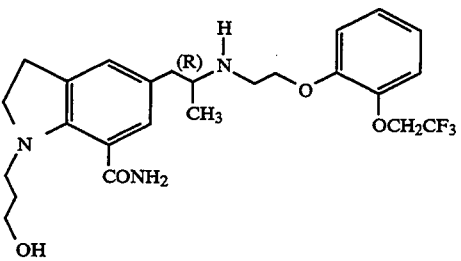

wherein the carbon atom marked with (R) represents a carbon atom in (R) configuration; or a salt thereof.

* * * * *